(12) United States Patent
Gottschling et al.

(10) Patent No.: US 10,307,402 B2
(45) Date of Patent: Jun. 4, 2019

(54) AZABENZIMIDAZOLE DERIVATIVES AS AGONISTS OF THE AMP-ACTIVATED PROTEIN KINASE

(71) Applicant: Boehringer Ingelheim International GmbH, Ingelheim am Rhein (DE)

(72) Inventors: Dirk Gottschling, Mittelbiberach (DE); Joerg P. Hehn, Biberach an der Riss (DE); Christoph Hoenke, Biberach an der Riss (DE); Elke Langkopf, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 15/543,244

(22) PCT Filed: Jan. 13, 2016

(86) PCT No.: PCT/EP2016/050558
§ 371 (c)(1),
(2) Date: Jul. 13, 2017

(87) PCT Pub. No.: WO2016/113300
PCT Pub. Date: Jul. 21, 2016

(65) Prior Publication Data
US 2018/0028500 A1 Feb. 1, 2018

(30) Foreign Application Priority Data
Jan. 16, 2015 (EP) .................................. 15151503

(51) Int. Cl.
| C07D 493/04 | (2006.01) |
| A61K 31/4188 | (2006.01) |
| A61K 31/34 | (2006.01) |
| A61K 31/437 | (2006.01) |
| C12N 9/12 | (2006.01) |

(52) U.S. Cl.
CPC .......... *A61K 31/4188* (2013.01); *A61K 31/34* (2013.01); *A61K 31/437* (2013.01); *C07D 493/04* (2013.01); *C12N 9/12* (2013.01)

(58) Field of Classification Search
CPC ..................................................... C07D 493/04
USPC .......................................... 546/118; 514/303
See application file for complete search history.

(56) References Cited

FOREIGN PATENT DOCUMENTS

| WO | 2010051206 A1 | 5/2010 |
| WO | 2012116145 A1 | 8/2012 |
| WO | 2014031515 A1 | 2/2014 |
| WO | 2014175330 A1 | 10/2014 |

OTHER PUBLICATIONS

Written Opinion of the International Searching Authority, for PCT/EP/2016/050558, Form PCT/ISA/220, dated 2016.
International Search report, for PCT/EP2016/050558, Form PCT/ISA/210, dated Aug. 3, 2016.
Abstract for WO2014175330, Feb. 23, 2017.

*Primary Examiner* — Patricia L Morris
(74) *Attorney, Agent, or Firm* — David L. Kershner

(57) ABSTRACT

The present invention relates to compounds of general formula I, wherein the group $R^1$, X and Y are defined as in claim 1, which have valuable pharmacological properties, in particular bind to the AMP-activated protein kinase (AMPK) and modulate its activity. The compounds are suitable for treatment and prevention of diseases which can be influenced by this receptor, such as metabolic diseases, in particular diabetes type 2.

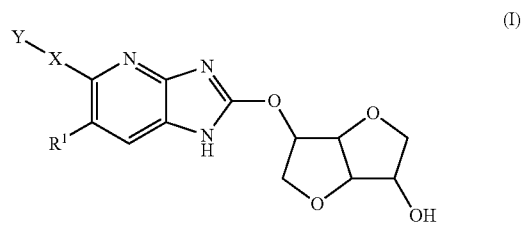

(I)

3 Claims, No Drawings

AZABENZIMIDAZOLE DERIVATIVES AS AGONISTS OF THE AMP-ACTIVATED PROTEIN KINASE

FIELD OF THE INVENTION

The present invention relates to novel azabenzimidazole derivatives that are agonists of the AMP-activated protein kinase (AMPK), to processes for their preparation, to pharmaceutical compositions containing these compounds and to their medical use for the prophylaxis and/or treatment of diseases which can be influenced by the modulation of the function of AMPK. Particularly, the pharmaceutical compositions of the invention are suitable for the prophylaxis and/or therapy of metabolic diseases, such as diabetes, more specifically type 2 diabetes mellitus, and conditions associated with the disease, including insulin resistance, obesity, cardiovascular disease and dyslipidemia.

BACKGROUND OF THE INVENTION

Metabolic diseases are diseases caused by an abnormal metabolic process and may either be congenital due to an inherited enzyme abnormality or acquired due to a disease of an endocrine organ or failure of a metabolically important organ such as the liver or the pancreas.

Diabetes mellitus is a disease state or process derived from multiple causative factors and is defined as a chronic hyperglycemia associated with resulting damages to organs and dysfunctions of metabolic processes. Depending on its etiology, one differentiates between several forms of diabetes, which are either due to an absolute (lacking or decreased insulin secretion) or to a relative lack of insulin. Diabetes mellitus Type I (IDDM, insulin-dependent diabetes mellitus) generally occurs in adolescents under 20 years of age. It is assumed to be of auto-immune etiology, leading to an insulitis with the subsequent destruction of the beta cells of the islets of Langerhans which are responsible for the insulin synthesis. In addition, in latent autoimmune diabetes in adults (LADA; Diabetes Care. 8: 1460-1467, 2001) beta cells are being destroyed due to autoimmune attack. The amount of insulin produced by the remaining pancreatic islet cells is too low, resulting in elevated blood glucose levels (hyperglycemia). Diabetes mellitus Type II generally occurs at an older age. It is above all associated with a resistance to insulin in the liver and the skeletal muscles, but also with a defect of the islets of Langerhans. High blood glucose levels (and also high blood lipid levels) in turn lead to an impairment of beta cell function and to an increase in beta cell apoptosis.

Persistent or inadequately controlled hyperglycemia is associated with a wide range of pathologies. Diabetes is a very disabling disease, because today's common antidiabetic drugs do not control blood sugar levels well enough to completely prevent the occurrence of high and low blood sugar levels. Out of range blood sugar levels are toxic and cause long-term complications for example retinopathy, nephropathy, neuropathy and peripheral vascular disease. There is also a host of related conditions, such as obesity, hypertension, stroke, heart disease and hyperlipidemia, for which persons with diabetes are substantially at risk.

Obesity is associated with an increased risk of follow-up diseases such as cardiovascular diseases, hypertension, diabetes, hyperlipidemia and an increased mortality. Diabetes (insulin resistance) and obesity are part of the "metabolic syndrome" which is defined as the linkage between several diseases (also referred to as syndrome X, insulin-resistance syndrome, or deadly quartet). These often occur in the same patients and are major risk factors for development of diabetes type II and cardiovascular disease. It has been suggested that the control of lipid levels and glucose levels is required to treat diabetes type II, heart disease, and other occurrences of metabolic syndrome (see e.g., Diabetes 48: 1836-1841, 1999; JAMA 288: 2209-2716, 2002).

Sensing and regulating cellular the energy status in response to environmental and/or nutritional stress is highly important and AMP-activated protein kinase (AMPK) is a major contributor for this task (Hardie et al. (2001) Bioessays 23: 1112; Kemp et al. (2003) Biochem. Soc. Transactions 31: 162). Cellular energy depletion leads to the activation of AMP-activated protein kinase (AMPK) thereby inhibiting ATP consuming and upregulating ATP generating pathways. On a cellular level several substrates are regulated by AMP-activated protein kinase (AMPK) such as acetyl-CoA-carboxylase (ACC) and HMG-CoA-reductase (Carling et al. (1987) FEBS Letters 223: 217), hormone-sensitive lipase (Garton et al. (1989) Eur. J. Biochem. 179: 249), malonyl-CoA-decarboxylase (Saha et al. (2000) J. Biol. Chem. 275: 24279) and glycerol-3-phosphate acyltransferase (Muoio et al. (1999) Biochem. J. 338: 783).

AMP-activated protein kinase (AMPK) mediated phosphorylation of ACC leads to inhibition of ACC, which then results in a decrease of fatty acid synthesis while fatty acid oxidation is increased. AMP-activated protein kinase (AMPK) mediated phosphorylation and inhibition of HMG-CoA-reductase leads to a decrease in cholesterol synthesis. Triacylglycerol synthesis and fatty acid oxidation is regulated by AMP-activated protein kinase (AMPK) via glycerol-3-phosphate acyltransferase. In addition AMP-activated protein kinase (AMPK) stimulates glucose transport in skeletal muscle and regulates the expression of genes involved in fatty acid and glucose metabolism (Hardie et al. (2001) Bioessays 23: 1112; Kemp et al. (2003) Biochem. Soc. Transactions 31: 162). Glucose homeostasis is mediated in liver and muscle by AMP-activated protein kinase (AMPK), wherein activation of AMP-activated protein kinase (AMPK) leads to an increase in GLUT 4-dependent glucose uptake (Sakamoto et al. (2008) Am. J. Physiol. Endocrinol. Metab. 295: E29-E37; Karagounis et al. (2009) Int. J. Biochem. Cell Biol. 41: 2360-2363; Pehmoller et al. (2009) Am. J. Physiol. Endocrinol. Metab. 297: E665-E675).

Besides energy regulation on a cellular level AMP-activated protein kinase (AMPK) also regulates whole body energy metabolism. Independently of the cellular AMP level AMP-activated protein kinase (AMPK) can be activated by the adipocyte derived hormones leptin (Minokoski et al. (2002) Nature 415: 339) and adiponectin (Yamauchi et al. (2002) Nature Medicine 8: 1288).

From the points discussed above activation of AMP-activated protein kinase (AMPK) in vivo is expected to result in hepatic stimulation of fatty acid oxidation; inhibition of cholesterol synthesis, lipogenesis and triglyceride synthesis; stimulation of skeletal muscle fatty acid oxidation and glucose uptake; improved insulin action; increase in energy expenditure and hence a decrease in body weight.

OBJECT OF THE PRESENT INVENTION

The object of the present invention is to provide new compounds, hereinafter described as compounds of formula I, in particular new azabenzimidazole derivatives, which are active with regard to the AMP-activated protein kinase (AMPK), notably are agonists of the AMP-activated protein kinase (AMPK).

A further object of the present invention is to provide new compounds, in particular new azabenzimidazole derivatives, which have an activating effect on the AMP-activated protein kinase (AMPK) in vitro and/or in vivo and possess suitable pharmacological and pharmacokinetic properties to use them as medicaments.

A further object of the present invention is to provide effective agonists of AMP-activated protein kinase (AMPK), in particular for the treatment of metabolic disorders, for example diabetes, dyslipidemia and/or obesity.

A further object of the present invention is to provide methods for treating a disease or condition mediated by the activation the AMP-activated protein kinase (AMPK) in a patient.

A further object of the present invention is to provide a pharmaceutical composition comprising at least one compound according to the invention.

A further object of the present invention is to provide a combination of at least one compound according to the invention with one or more additional therapeutic agents.

Further objects of the present invention become apparent to the one skilled in the art by the description hereinbefore and in the following and by the examples.

AMP-activated protein kinase (AMPK) modulators are known in the art, for example, the compounds disclosed in WO 2012033149, WO 2012116145 and WO 2014175330. The azabenzimidazole derivatives of the present invention may provide several advantages, such as enhanced potency, high metabolic and/or chemical stability, high selectivity and/or tolerability and in consequence low toxicity, reduced risk to cause adverse events or undesirable side effects, and enhanced solubility.

SUMMARY OF THE INVENTION

In a first aspect the invention relates to compounds of formula I

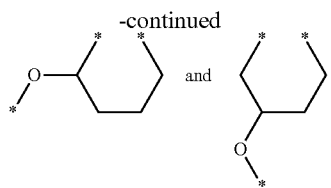

wherein $R^1$ is selected from the group $R^1$-G1 consisting of F and Cl;

X is selected from the group X-G1 consisting of a divalent straight-chained or branched —$C_{1-3}$-alkyl-O— linker attached via the O-atom to the imidazopyridine core and a trivalent linker selected from

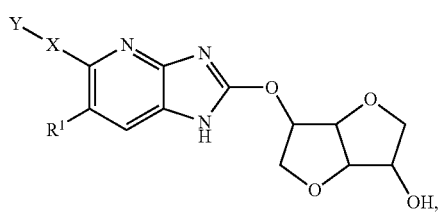

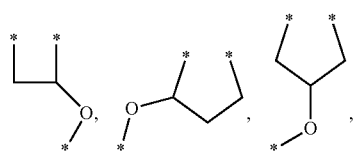

attached via the O-atom to the imidazopyridine core and attached via the remaining two binding positions to vicinal carbon atoms of group Y; and Y is selected from the group Y-G1 consisting of phenyl and pyridinyl, which both are optionally substituted with 1 to 2 groups independently selected from F, Cl, NC—, $H_3C$—, $F_3C$—, and $H_3C$—O—, but which both are mandatorily substituted with a group selected from $R^S R^{S'}(O=)S=N$—, $R^S R^{S'}(O=)S=N$—$C_{1-3}$-alkyl-, $R^S R^{S'}(O=)S=N$—$C(=O)$—, $(R^N)N=S(=O)(R^S)$—, $(R^N)N=S(=O)(R^S)$—$CH_2$—, $R^S R^{S'}(R^{N'}—N=)S=N$—$C(=O)$—, $R^S R^{S'}(O=)S=N$—$C(=O)$—$C_{1-3}$-alkyl-, $R^S R^{S'}(O=)S=N$—$C(=O)$—$C_{2-3}$-alkenyl-, and $R^S R^{S'}(R^{N'}—N=)S=N$—, wherein $R^N$ is selected from H, NC— and $C_{1-4}$-alkyl, and $R^{N'}$ is selected from H and NC—, wherein $R^S$ is selected from $H_3C$—, $H_5C_2$— and cyclopropyl, and $R^{S'}$ is independently selected from $C_{1-4}$-alkyl- and $C_{3-6}$-cycloalkyl, from a heterocyclyl group selected from tetrahydrofuranyl, tetrahydropyranyl, pyrrolidinyl, piperidinyl and piperidinyl-$H_2C$—, from an aryl group selected from phenyl and benzyl, and from the heteroaryl group pyridinyl, wherein any alkyl and cycloalkyl group mentioned hereinbefore under $R^N$, $R^S$ and $R^{S'}$ is optionally substituted with F, $(C_{1-3}\text{-alkyl})_2 N$—, $(C_{1-3}\text{-alkyl})HN$—, $H_2N$—, NC—, HO—, $H_3C$—, and $H_3C$—O—, wherein any heterocyclyl group mentioned hereinbefore under $R^{S'}$ is optionally substituted with F, $C_{1-3}$-alkyl-$C(=O)$—, and $H_3C$—, and wherein any aryl and heteroaryl group mentioned hereinbefore under $R^{S'}$ is optionally substituted with 1 to 3 groups independently selected from halogen, NC—, HO—, $C_{1-3}$-alkyl, and $C_{1-3}$-alkyl-O—, or $R^S$ and $R^{S'}$ together with the S-atom these groups are attached to form a 4-8 membered saturated monocyclic or bicyclic fused, bridged or spiro ring system, wherein one —$CH_2$— group optionally is replaced by —$NR^{N''}$— or —O—, and which is optionally substituted with 1 to 2 groups independently selected from F—, $(C_{1-3}\text{-alkyl})_2 N$—, $(C_{1-3}\text{-alkyl})HN$—, $H_2N$—, NC—, HO—, $H_3C$—, and $H_3C$—O—, wherein $R^{N''}$ is selected from H, $H_3C$—, $H_5C_2$—, $H_3C$—$C(=O)$—, $(H_3c)_3C$—O—$C(=O)$— and cyclopropyl;

wherein in any definition mentioned hereinbefore and if not specified otherwise, any alkyl group or sub-group may be straight-chained or branched, the isoforms, tautomers, stereoisomers, metabolites, prodrugs, solvates, hydrates, and the salts thereof, particularly the physiologically acceptable salts thereof with inorganic or organic acids or bases, or the combinations thereof.

The extension -Gn used within the definitions is meant to identify genus n of the respective substituent. For example, $R^1$-G1 defines genus 1 of the substituent $R^1$.

In a further aspect this invention relates to a pharmaceutical composition, comprising one or more compounds of general formula I or one or more pharmaceutically acceptable salts thereof according to the invention, optionally together with one or more inert carriers and/or diluents.

In a further aspect this invention relates to a method for treating diseases or conditions which are mediated by activating the AMP-activated protein kinase (AMPK) in a patient in need thereof characterized in that a compound of general formula I or a pharmaceutically acceptable salt thereof is administered to the patient.

According to another aspect of the invention, there is provided a method for treating a metabolic disease or disorder, such as diabetes, dyslipidemia and/or obesity, in a patient in need thereof characterized in that a therapeutically effective amount of a compound of general formula I or a pharmaceutically acceptable salt thereof is administered to the patient.

According to another aspect of the invention, there is provided a method for treating a cardiovascular disease or disorder, such as myocardial infarction, stroke, heart failure, coronary artery disease, hypertension, in a patient in need thereof characterized in that a therapeutically effective amount of a compound of general formula I or a pharmaceutically acceptable salt thereof is administered to the patient.

According to another aspect of the invention, there is provided a method for treating a kidney disease or disorder, such as diabetic nephropathy, chronic kidney disease, acute kidney injury and/or polycystic kidney disease in a patient in need thereof characterized in that a therapeutically effective amount of a compound of general formula I or a pharmaceutically acceptable salt thereof is administered to the patient.

According to another aspect of the invention, there is provided the use of a compound of the general formula I or a pharmaceutically acceptable salt thereof for the manufacture of a medicament for a therapeutic method as described hereinbefore and hereinafter.

According to another aspect of the invention, there is provided a compound of the general formula I or a pharmaceutically acceptable salt thereof for use in a therapeutic method as described hereinbefore and hereinafter.

In a further aspect this invention relates to a method for treating a disease or condition mediated by the activation of the AMP-activated protein kinase (AMPK) in a patient that includes the step of administering to the patient in need of such treatment a therapeutically effective amount of a compound of the general formula I or a pharmaceutically acceptable salt thereof in combination with a therapeutically effective amount of one or more additional therapeutic agents.

In a further aspect this invention relates to the use of a compound of the general formula I or a pharmaceutically acceptable salt thereof in combination with one or more additional therapeutic agents for the treatment of diseases or conditions which are mediated by the activation of the AMP-activated protein kinase (AMPK).

In a further aspect this invention relates to a pharmaceutical composition which comprises a compound according to general formula I or a pharmaceutically acceptable salt thereof and one or more additional therapeutic agents, optionally together with one or more inert carriers and/or diluents.

Other aspects of the invention become apparent to the one skilled in the art from the specification and the experimental part as described hereinbefore and hereinafter.

DETAILED DESCRIPTION

Unless otherwise stated, the groups, residues, and substituents, particularly $R^1$, X, and Y are defined as above and hereinafter. If residues, substituents, or groups occur several times in a compound, they may have the same or different meanings.

Some preferred meanings of individual groups and substituents of the compounds according to the invention will be given hereinafter. Any and each of these definitions may be combined with each other.

$R^1$:

$R^1$-G1:

The group $R^1$ is preferably selected from the group $R^1$-G1 as defined hereinbefore.

$R^1$-G2:

In another embodiment the group $R^1$ is Cl.

X:

X-G1:

The group X is preferably selected from the group X-G1 as defined hereinbefore.

X-G2:

In another embodiment the group X is selected from the group X-G2 consisting of a divalent straight-chained or branched —$C_{1-3}$-alkyl-O— linker attached via the O-atom to the imidazopyridine core.

X-G3:

In another embodiment X-G3 the group X is —$CH_2$—O— attached via the O-atom to the imidazopyridine core.

Y:

Y-G1:

The group Y is preferably selected from the group Y-G1 as defined hereinbefore.

Y-G2:

In another embodiment the group Y is selected from the group Y-G2 consisting of monofluoro-phenyl and difluoro-phenyl, which both are mandatorily substituted with a group selected from $R^S R^{S'}(O=)S=N—$, $R^S R^{S'}(O=)S=N—C_{1-3}$-alkyl-, $R^S R^{S'}(O=)S=N—C(=O)—$, $(R^N)N=S(=O)(R^S)—$, $(R^N)N=S(=O)(R^S)—CH_2—$, $R^S R^{S'}(R^{N'}—N=)S=N—C(=O)—$, $R^S R^{S'}(O=)S=N—C(=O)—C_{1-3}$-alkyl-, $R^S R^{S'}(O=)S=N—C(=O)—C_{2-3}$-alkenyl- and $R^S R^{S'}(R^{N'}—N=)S=N—$, wherein $R^N$ is selected from H, NC— and $H_3C—$, and $R^{N'}$ is H or —CN, wherein $R^S$ is selected from $H_3C—$, $H_5C_2—$ and cyclopropyl, and $R^{S'}$ is independently selected from $H_3C—$, $H_5C_2—$, $(H_3C)_2CH—$, $(H_3C)_3—$, cyclopropyl, cyclopentyl, cyclohexyl, tetrahydropyranyl, piperidinyl, piperidinyl-$CH_2—$, HO—$C_{2-4}$-alkyl-, $H_3C—O—C_2$-alkyl-, phenyl, benzyl and pyridinyl, or $R^S$ and $R^{S'}$ linked together are selected from —$(CH_2)_3—$, —$(CH_2)_4—$, —$(CH_2)_5—$, —$(CH_2)_2—N(R^{N''})—(CH_2)_2—$ and —$(CH_2)_2—O—(CH_2)_2—$, together with the S-atom these groups are attached to forming a 4-6 membered saturated monocyclic ring system optionally substituted with F—, HO—, $H_3C—$, or $H_3C—O—$, wherein any cyclopropyl, cyclopentyl, cyclohexyl, piperidinyl, piperidinyl-$CH_2—$, phenyl, benzyl and pyridinyl groups mentioned under $R^{S'}$ are optionally substituted at a ring-carbon atom with F, OH—, $H_3C—$, or $H_3C—O—$, wherein the piperidinyl and piperdinyl-$CH_2—$ group mentioned under $R^{S'}$ is optionally substituted at the N-atom with $H_3C—$, and wherein $R^{N''}$ is selected from H, H₃C—, H₅C₂—, H₃C—C(=O)—, (H₃C)₃C—O—C(=O)— and cyclopropyl.

Y-G3:

In another embodiment the group Y is selected from the group Y-G3 consisting of

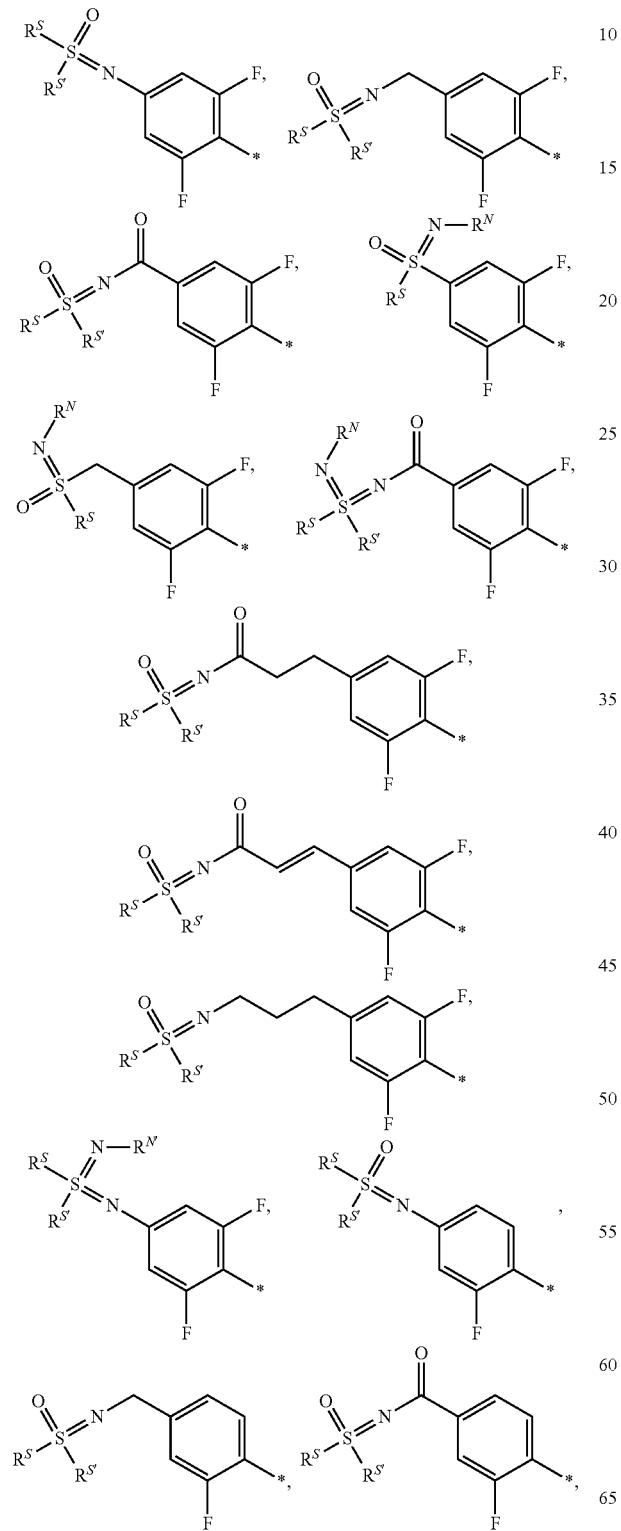

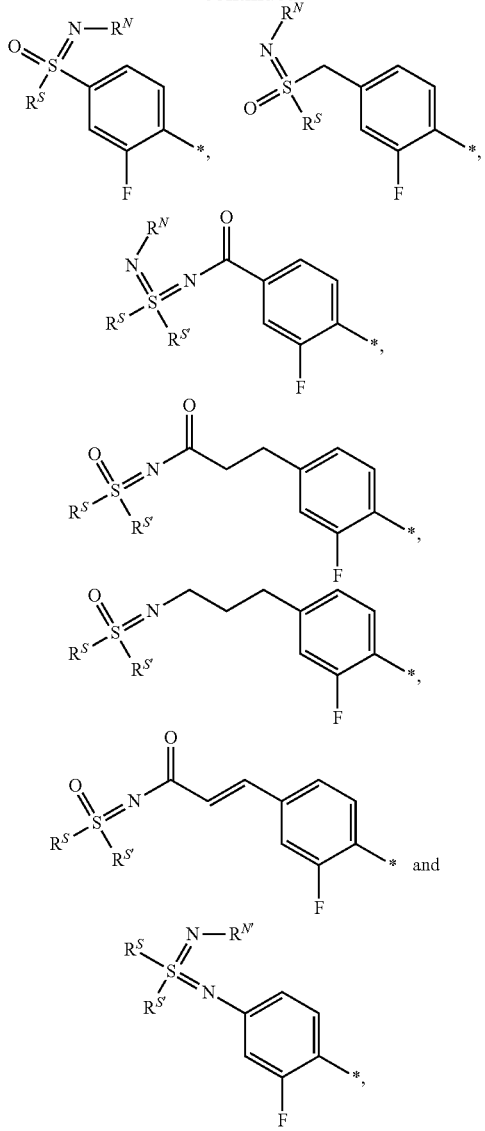

wherein $R^N$ is selected from H, NC—, H₃C—, and $R^{N'}$ is H or —CN, wherein $R^S$ is selected from H₃C— H₅C₂— and cyclopropyl, and $R^{S'}$ is independently selected from H₃C—, H₅C₂—, (H₃C)₂CH—, (H₃C)₃C—, cyclopropyl, cyclopentyl, cyclohexyl, tetrahydropyranyl, piperidinyl, piperidinyl-CH₂—, HO—C₂₋₄-alkyl-, H₃C—O—C₂-alkyl-, phenyl, benzyl and pyridinyl, or $R^S$ and $R^{S'}$ linked together are selected from —(CH₂)₃—, —(CH₂)₄—, —(CH₂)₅—, —(CH₂)₂—N($R^{N''}$)—(CH₂)₂— and —(CH₂)₂—O—(CH₂)₂—, together with the S-atom these groups are attached to forming a 4-6 membered saturated monocyclic ring system optionally substituted with HO—, H₃C—, or H₃C—O—, wherein any cyclopropyl, cyclopentyl, cyclohexyl, piperidinyl, piperidinyl-CH₂—, phenyl, benzyl and pyridinyl groups mentioned under $R^{S'}$ are optionally substituted at a ring-carbon atom with OH—, H₃C—, or H₃C—O—, wherein the piperidinyl and piperdinyl-CH₂— group mentioned under $R^{S'}$ is optionally substituted at the N-atom with H₃C—, and wherein $R^{N'''}$ is selected from H, $H_3C$— and $H_3C$—C(=O)—.

Y-G4:
In another embodiment the group Y is selected from the group Y-G4 consisting of

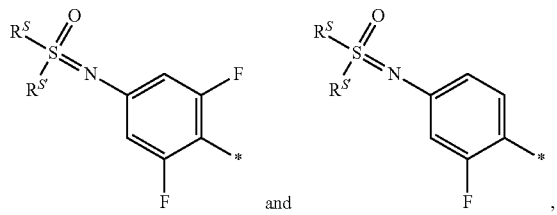

and wherein $R^S$ is selected from $H_3C$—, $H_5C_2$— and cyclopropyl, and $R^{S'}$ is independently selected from $H_3C$—, $H_5C_2$—, $(H_3C)_2CH$—, $(H_3C)_3C$—, cyclopropyl, cyclopentyl, cyclohexyl, tetrahydropyranyl, piperidinyl, piperidinyl-$CH_2$—, HO—$C_{2-4}$-alkyl-, $H_3C$—O—$C_2$-alkyl-, phenyl, benzyl and pyridinyl, or $R^S$ and $R^{S'}$ linked together are selected from —$(CH_2)_3$—, —$(CH_2)_4$—, —$(CH_2)_5$—, —$(CH_2)_2$—N($R^{N'''}$)—$(CH_2)_2$—, and —$(CH_2)_2$—O—$(CH_2)_2$—, together with the S-atom these groups are attached to forming a 4-6 membered saturated monocyclic ring system optionally substituted with HO—, $H_3C$—, or $H_3C$—O—,
  wherein any cyclopropyl, cyclopentyl, cyclohexyl, piperidinyl, piperidinyl-$CH_2$—, phenyl, benzyl and pyridinyl groups mentioned under $R^{S'}$ are optionally substituted at a ring-carbon atom with OH—, $H_3C$—, or $H_3C$—O—,
  wherein the piperidinyl and piperidinyl-$CH_2$— group mentioned under $R^{S'}$ is optionally substituted at the N-atom with $H_3C$—, and
  wherein $R^{N'''}$ is selected from H, $H_3C$— and $H_3C$—C(=O)—.

Y-G5:
In another embodiment the group Y is selected from the group Y-G5 consisting of

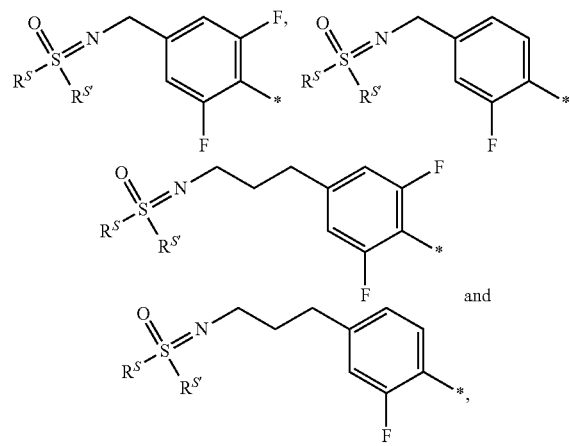

wherein $R^S$ is selected from $H_3C$— and $R^{S'}$ is independently selected from $H_3C$—, and cyclopropyl or $R^S$ and $R^{S'}$ linked together are selected from —$(CH_2)_3$ and —$(CH_2)_2$—O—$(CH_2)_2$—, together with the S-atom these groups are attached to forming a 4-6 membered saturated monocyclic ring system.

Y-G6:
In another embodiment the group Y is selected from the group Y-G6 consisting of

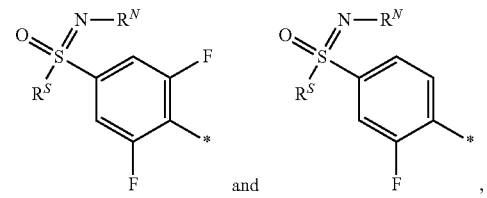

and wherein $R^N$ is selected from H and $H_3C$— and $R^S$ is $H_3C$—.

Y-G7:
In another embodiment the group Y is selected from the group Y-G7 consisting of

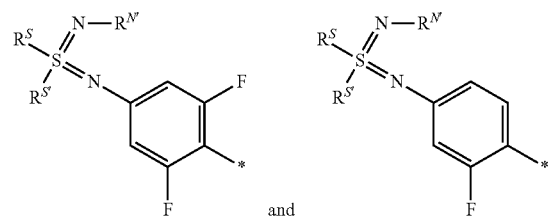

and wherein $R^{N'}$ is —CN,
$R^S$ is $H_3C$— and $R^{S'}$ is independently selected from $H_3C$—, and cyclopropyl or $R^S$ and $R^{S'}$ linked together are selected from —$(CH_2)_3$— and —$(CH_2)_2$—O—$(CH_2)_2$—, together with the S-atom these groups are attached to forming a 4-6 membered saturated monocyclic ring system.

Y-G8:
In another embodiment the group Y is selected from the group Y-G8 consisting of

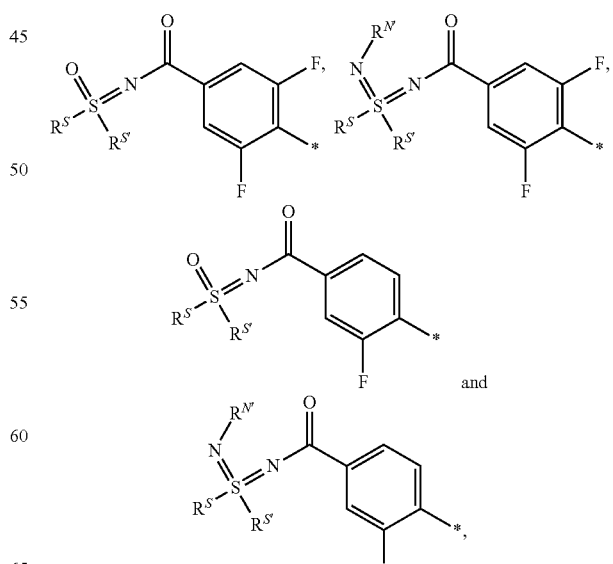

and wherein $R^{N'}$ is H, $R^S$ is selected from $H_3C-$, $H_5C_2-$ and cyclopropyl, and $R^{S'}$ is independently selected from $H_3C-$, $H_5C_2-$, $(H_3C)_2CH-$, $(H_3C)_3C-$, cyclopropyl, cyclopentyl, cyclohexyl, tetrahydropyranyl, piperidinyl, piperdininyl-$CH_2-$, HO—$C_{2-4}$-alkyl-, $H_3C-O-C_2$-alkyl-, phenyl, benzyl and pyridinyl, or $R^S$ and $R^{S'}$ linked together are selected from —$(CH_2)_3$—, —$(CH_2)_4$—, —$(CH_2)_5$—, —$(CH_2)_2$—$N(R^{N''})$—$(CH_2)_2$—, and —$(CH_2)_2$—O—$(CH_2)_2$—, together with the S-atom these groups are attached to forming a 4-6 membered saturated monocyclic ring system optionally substituted with HO—, $H_3C-$, or $H_3C-O-$, wherein any cyclopropyl, cyclopentyl, cyclohexyl, piperidinyl, piperdinyl-$CH_2-$, phenyl, benzyl and pyridinyl groups mentioned under $R^{S'}$ are optionally substituted at a ring-carbon atom with OH—, $H_3C-$, or $H_3C-O-$, wherein the piperidinyl and piperdinyl-$CH_2-$ group mentioned under $R^{S'}$ is optionally substituted at the N-atom with $H_3C-$, and wherein $R^{N'}$ is selected from H, $H_3C-$ and $H_3C-C(=O)-$.

Y-G9:

In another embodiment the group Y is selected from the group Y-G9 consisting of

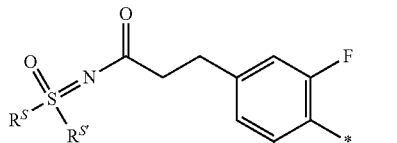

and

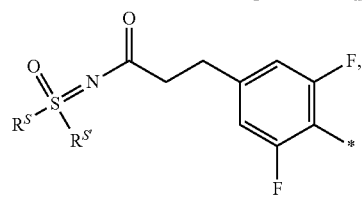

wherein $R^S$ is $H_3C-$ and $R^{S'}$ is independently selected from $H_3C-$, and cyclopropyl or $R^S$ and $R^{S'}$ linked together are selected from —$(CH_2)_3$ and —$(CH_2)_2$—O—$(CH_2)_2$—, together with the S-atom these groups are attached to forming a 4-6 membered saturated monocyclic ring system.

Y-G10:

In another embodiment the group Y is selected from the group Y-G10 consisting of

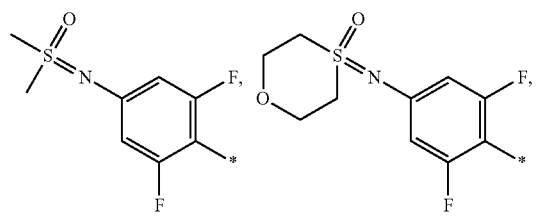 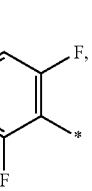

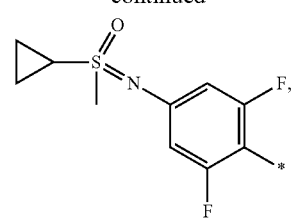

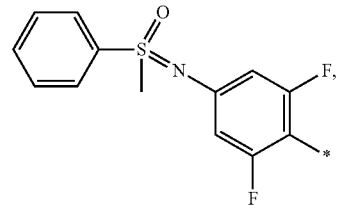

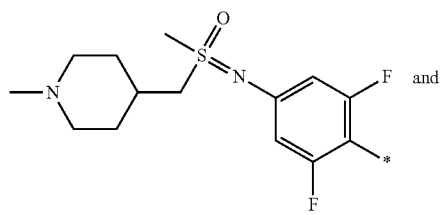 and

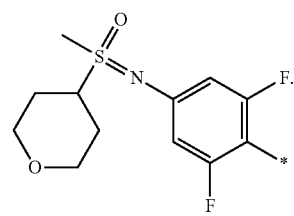

Y-G11:

In another embodiment the group Y is

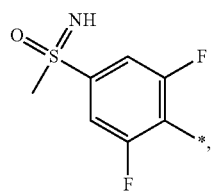

Y-G12:

In another embodiment the group Y is

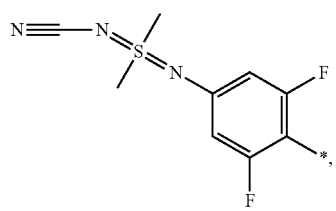

Y-G13:

In another embodiment the group Y is selected from the group Y-G13 consisting of

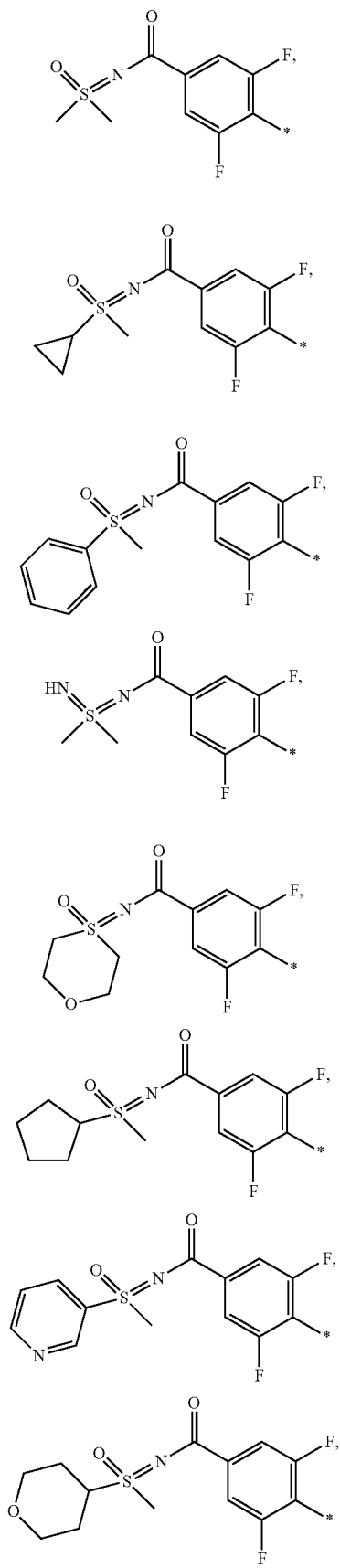
Y-G14:
In another embodiment the group Y is selected from the group Y-G14 consisting of
and
Y-G15:
In another embodiment the group Y is selected from the group Y-G15 consisting of

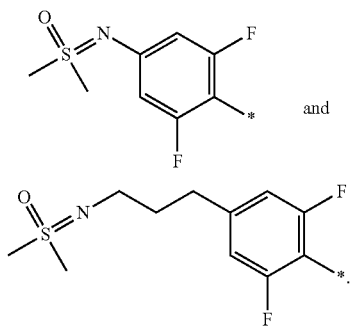

and

Examples of preferred subgeneric embodiments (E) according to the present invention are set forth in the following table 1, wherein each substituent group of each embodiment is defined according to the definitions set forth hereinbefore and wherein all other substituents of the formula I are defined according to the definitions set forth hereinbefore:

TABLE 1

| Embodiment | R¹- | X- | Y- |
|---|---|---|---|
| E-1 | R¹-G1 | X-G1 | Y-G1 |
| E-2 | R¹-G1 | X-G1 | Y-G2 |
| E-3 | R¹-G1 | X-G1 | Y-G3 |
| E-4 | R¹-G1 | X-G1 | Y-G4 |
| E-5 | R¹-G1 | X-G1 | Y-G5 |
| E-6 | R¹-G1 | X-G1 | Y-G6 |
| E-7 | R¹-G1 | X-G1 | Y-G7 |
| E-8 | R¹-G1 | X-G1 | Y-G8 |
| E-9 | R¹-G1 | X-G1 | Y-G9 |
| E-10 | R¹-G1 | X-G1 | Y-G10 |
| E-11 | R¹-G1 | X-G1 | Y-G11 |
| E-12 | R¹-G1 | X-G1 | Y-G12 |
| E-13 | R¹-G1 | X-G1 | Y-G13 |
| E-14 | R¹-G1 | X-G1 | Y-G14 |
| E-15 | R¹-G1 | X-G1 | Y-G15 |
| E-16 | R¹-G1 | X-G2 | Y-G1 |
| E-17 | R¹-G1 | X-G2 | Y-G2 |
| E-18 | R¹-G1 | X-G2 | Y-G3 |
| E-19 | R¹-G1 | X-G2 | Y-G4 |
| E-20 | R¹-G1 | X-G2 | Y-G5 |
| E-21 | R¹-G1 | X-G2 | Y-G6 |
| E-22 | R¹-G1 | X-G2 | Y-G7 |
| E-23 | R¹-G1 | X-G2 | Y-G8 |
| E-24 | R¹-G1 | X-G2 | Y-G9 |
| E-25 | R¹-G1 | X-G2 | Y-G10 |
| E-26 | R¹-G1 | X-G2 | Y-G11 |
| E-27 | R¹-G1 | X-G2 | Y-G12 |
| E-28 | R¹-G1 | X-G2 | Y-G13 |
| E-29 | R¹-G1 | X-G2 | Y-G14 |
| E-30 | R¹-G1 | X-G2 | Y-G15 |
| E-31 | R¹-G1 | X-G3 | Y-G1 |
| E-32 | R¹-G1 | X-G3 | Y-G2 |
| E-33 | R¹-G1 | X-G3 | Y-G3 |
| E-34 | R¹-G1 | X-G3 | Y-G4 |
| E-35 | R¹-G1 | X-G3 | Y-G5 |
| E-36 | R¹-G1 | X-G3 | Y-G6 |
| E-37 | R¹-G1 | X-G3 | Y-G7 |
| E-38 | R¹-G1 | X-G3 | Y-G8 |
| E-39 | R¹-G1 | X-G3 | Y-G9 |
| E-40 | R¹-G1 | X-G3 | Y-G10 |
| E-41 | R¹-G1 | X-G3 | Y-G11 |
| E-42 | R¹-G1 | X-G3 | Y-G12 |
| E-43 | R¹-G1 | X-G3 | Y-G13 |
| E-44 | R¹-G1 | X-G3 | Y-G14 |
| E-45 | R¹-G1 | X-G3 | Y-G15 |

A second set of embodiments E-1a to E-45a is characterized by general formula

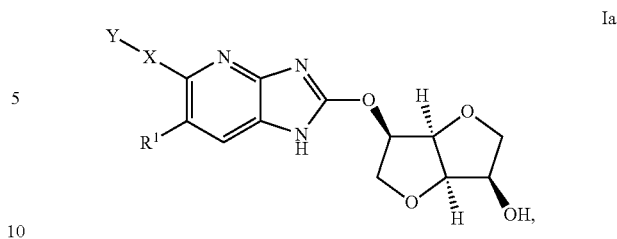

wherein $R^1$, X and Y are defined as shown in table 1 for embodiments E-1 to E45.

Exemplary to embodiment E-32a compounds of formula Ia are preferred, wherein
$R^1$ is selected from the group consisting of F and Cl;
X is —CH$_2$—O— attached via the O-atom to the imidazopyridine core;
Y is selected from the group Y-G2 consisting of monofluoro-phenyl and difluorophenyl,
which both are mandatorily substituted with a group selected from $R^S R^{S'}(O=)S=N-$, $R^S R^{S'}(O=)S=N-C_{1-3}$-alkyl-, $R^S R^{S'}(O=)S=N-C(=O)-$, $(R^N)N=S(=O)(R^S)-$, $(R^N)N=S(=O)(R^S)-CH_2-$, $R^S R^{S'}(R^{N'}-N=)S=N-C(=O)-$, $R^S R^{S'}(O=)S=N-C(=O)-C_{1-3}$-alkyl-, $R^S R^{S'}(O=)S=N-C(=O)-C_{2-3}$-alkenyl- and $R^S R^{S'}(R^{N'}-N=)S=N-$,
wherein $R^N$ is selected from H, NC— and H$_3$C—, and $R^{N'}$ is H or —CN,
wherein $R^S$ is selected from H$_3$C—, H$_5$C$_2$— and cyclopropyl, and $R^{S'}$ is independently selected from H$_3$C—, H$_5$C$_2$—, (H$_3$C)$_2$CH—, (H$_3$C)$_3$—, cyclopropyl, cyclopentyl, cyclohexyl, tetrahydropyranyl, piperidinyl, piperdinyl-CH$_2$—, HO—C$_{2-4}$-alkyl-, H$_3$C—O—C$_2$-alkyl-, phenyl, benzyl and pyridinyl, or $R^S$ and $R^{S'}$ linked together are selected from —(CH$_2$)$_3$—, —(CH$_2$)$_4$—, —(CH$_2$)$_5$—, —(CH$_2$)$_2$—N(R$^{N''}$)—(CH$_2$)$_2$ and —(CH$_2$)$_2$—O—(CH$_2$)$_2$—, together with the S-atom these groups are attached to forming a 4-6 membered saturated monocyclic ring system optionally substituted with F—, HO—, H$_3$C—, or H$_3$C—O—,
wherein any cyclopropyl, cyclopentyl, cyclohexyl, piperidinyl, piperdinyl-CH$_2$—, phenyl, benzyl and pyridinyl groups mentioned under $R^{S'}$ are optionally substituted at a ring-carbon atom with F, OH—, H$_3$C—, or H$_3$C—O—,
wherein the piperidinyl and piperdinyl-CH$_2$— group mentioned under $R^{S'}$ is optionally substituted at the N-atom with H$_3$C—, and
wherein $R^{N''}$ is selected from H, H$_3$C—, H$_5$C$_2$—, H$_3$C—C(=O)—, (H$_3$C)$_3$C—O—C(=O)— and cyclopropyl,
and the pharmaceutically acceptable salts thereof.

Further preferred embodiments are those of E-1 to E-45 as well as of E-1a to E-45a wherein $R^1$ is Cl.

Particularly preferred compounds, including their tautomers and stereoisomers, the salts thereof, or any solvates or hydrates thereof, are described in the experimental section hereinafter.

The compounds according to the invention and their intermediates may be obtained using methods of synthesis which are known to the one skilled in the art and described in the literature of organic synthesis. Preferably the compounds are obtained analogously to the methods of preparation explained more fully hereinafter, in particular as described in the experimental section. In some cases the sequence adopted in carrying out the reaction schemes may be varied. Variants of these reactions that are known to the skilled man but are not described in detail here may also be used. The general processes for preparing the compounds according to the invention will become apparent to the skilled man on studying the schemes that follow. Starting compounds are commercially available or may be prepared by methods that are described in the literature or herein, or may be prepared in an analogous or similar manner. Before the reaction is carried out any corresponding functional groups in the compounds may be protected using conventional protecting groups. These protecting groups may be cleaved again at a suitable stage within the reaction sequence using methods familiar to the skilled man.

The compounds of the invention I are preferably accessed from a precursor 1a or 1b that bears the protected imidazopyridine-nitrogen in position 3 or 1 (Scheme 1); $R^1$, X and Y have the meaning as defined hereinbefore and hereinafter. For the sake of convenience only the $N^3$ protected species (1a in Scheme 1) will be shown hereinafter, although by and large all transformations described below are also applicable to the $N^1$ protected series (1b in Scheme 1). Amino-acetal derivatives can be cleaved under acidic conditions such as HCl, $H_2SO_4$, $CF_3CO_2H$, $MeSO_3H$, $KHSO_4$, $HCO_2H$, $BF_3xOEt_2$ in a solvent such as dichloromethane, water, tetrahydrofuran, 1,4-dioxane or mixtures thereof at −10 to 100° C. In addition to cleavage under acidic conditions, amino-acetal derivatives bearing a $Si(CH_3)_3$ group can also be cleaved in the presence of tetrabutylammonium fluoride.

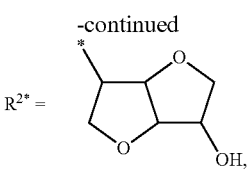

$PG^1$=$CH_2$—O—$C_{1-3}$-alkyl, wherein alkyl is optionally substituted with $Si(CH_3)_3$, $PG^2$=suitable protecting group for sulfoximines or sulfodiimines e.g. tert-butoxycarbonyl, 2-(trimethylsilyl)ethoxycarbonyl, acetyl, or 2,2,2-trifluoroacetyl, $PG^3$=silyl-containing protecting group like triethylsilyl (TES), triisopropylsilyl (TIPS) or t-butyldimethylsilyl (TBS or TBDMS).

The N atom of the sulfoximine or sulfodiimine moiety within Y might be protected with a suitable protecting group $PG^2$, e.g. a tert-butoxycarbonyl, 2-(trimethylsilyl)ethoxycarbonyl, acetyl, or 2,2,2-trifluoroacetyl group. The protecting group $PG^2$ is either removed together with $PG^1$ and $PG^3$ in one reaction step or in an additional deprotection step, depending on the nature of $PG^1$, $PG^2$ and $PG^3$. The tert.-butyloxy-carbonyl-protecting group as $PG^2$ can be cleaved under acidic conditions such as HCl, $H_2SO_4$, $CF_3CO_2H$, $MeSO_3H$, $KHSO_4$, $HCO_2H$, $BF_3xOEt_2$ in a solvent such as dichloromethane, water, tetrahydrofuran, 1,4-dioxane or mixtures thereof at −10 to 100° C. The trifluoroacetyl-protecting group as $PG^2$ can be cleaved under basic conditions such as $K_2CO_3$, NaOH, KOH, NaOMe, NaOEt, NaOtBu in a solvent such as water, methanol, tetrahydrofuran, 1,4-dioxane or mixtures thereof at −10 to 50° C. The 2-(trimethylsilyl)-ethoxycarbonyl-group as $PG^2$ can be cleaved under acidic conditions such as $CF_3CO_2H$ in a solvent such as dichloromethane at −10 to 100° C.

$PG^3$ might represent a silyl-containing protecting group like triethylsilyl (TES), triisopropylsilyl (TIPS) or t-butyldimethylsilyl (TBS or TBDMS). The protecting group $PG^3$ is either removed together with $PG^1$ and $PG^2$ in one reaction step or in an additional deprotection step, depending on the nature of $PG^1$, $PG^2$ and $PG^3$. Si-containing protecting groups can be cleaved under acidic conditions such as $CF_3CO_2H$ in a solvent such as dichloromethane at −10 to 100° C.

Scheme 1

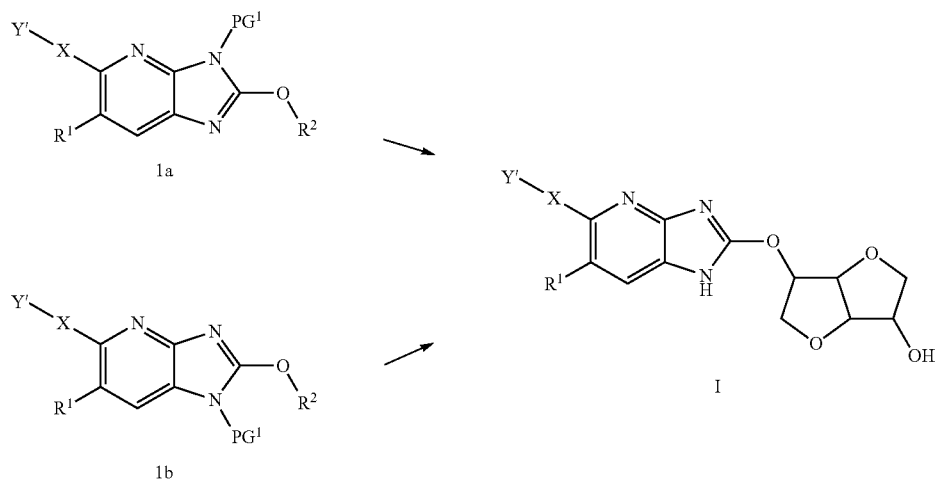

Y'=Y or Y-$PG^2$, $R^2$ is

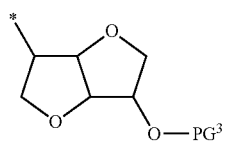

or

In addition to cleavage under acidic conditions, Si-containing protection groups can also be cleaved in the presence of tetrabutylammonium fluoride.

Compounds 1 can be prepared from imidazopyridine derivatives 2 and alcohol derivatives 3 (Scheme 2); R¹, X and Y' have the meaning defined hereinbefore and hereinafter.

Scheme 2

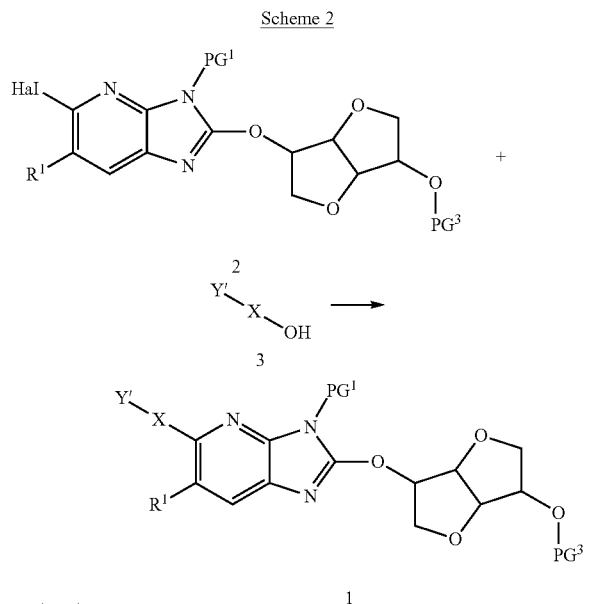

Hal=Cl, Br, I,
Y'=Y or Y-PG²,
PG¹=as defined in Scheme 1,
PG²=suitable protecting group for sulfoximines or sulfodiimines e.g. tert-butoxycarbonyl, 2-(trimethylsilyl)ethoxycarbonyl, acetyl, or 2,2,2-trifluoroacetyl,
PG³=as defined in Scheme 1.

The reaction is preferably conducted with a copper derived catalyst, e.g. copper-(I)-iodide in the presence of a ligand e.g. 1,10-phenanthroline and a base, e.g. cesium carbonate, in a solvent e.g. toluene or 1,4-dioxane at 40° C. to 120° C.

Compounds 1' bearing a sulfoximine or sulfodiimine linked via the nitrogen to an aryl or heteroaryl group Y'" can be prepared from halogen compounds 9 via direct coupling of the sulfoximine or sulfodiime of the general formula 21 (Scheme 3); R¹, R², X, Y, $R^{N'}$, $R^S$ and $R^{S'}$ have the meaning defined hereinbefore and hereinafter.

Scheme 3

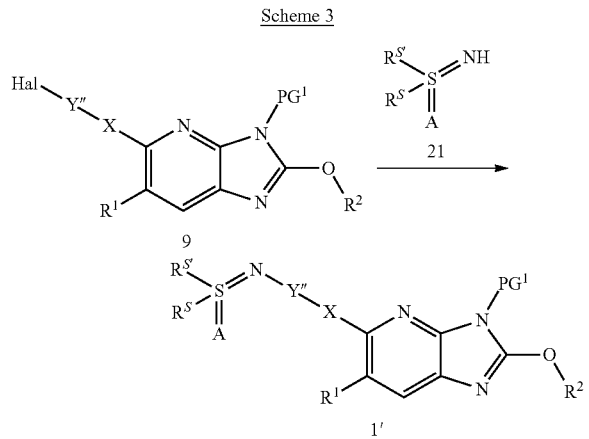

Hal=Cl, Br, I,
PG¹=as defined in Scheme 1,
A=O, $NR^{N'}$,
$(R^S)(R^{S'})S(=A)=N-Y'''$ denotes a substructure of Y.

The coupling reaction is preferably conducted with a palladium derived catalyst and a suitable ligand, e.g. palladium(II) acetate and 2-dicyclohexylphosphino-2',6'-di-isopropoxy-1,1'-biphenyl (RuPhos), tris(dibenzylideneacetone)dipalladium(0) and 2-(di-t-butylphosphino)biphenyl, or palladium(II) acetate and racemic 2,2'-bis-(diphenylphosphino)-1,1'-binaphthyl in the presence of a base, e.g. $Cs_2CO_3$ or sodium tert-butoxide in a suitable solvent such as 1,4-dioxane or toluene at 40° C. to 120° C.

Compounds 1" bearing a sulfoximine or a sulfodiimine linked via the nitrogen to a carbonyl on Y'" can be prepared via reaction of the corresponding carboxylic acid derivatives 10 with the sulfoximine or sulfodiimine of the general formula 21 (Scheme 4); R¹, R², X, Y, $R^{N'}$, $R^S$ and $R^{S'}$ have the meaning defined hereinbefore and hereinafter.

Scheme 4

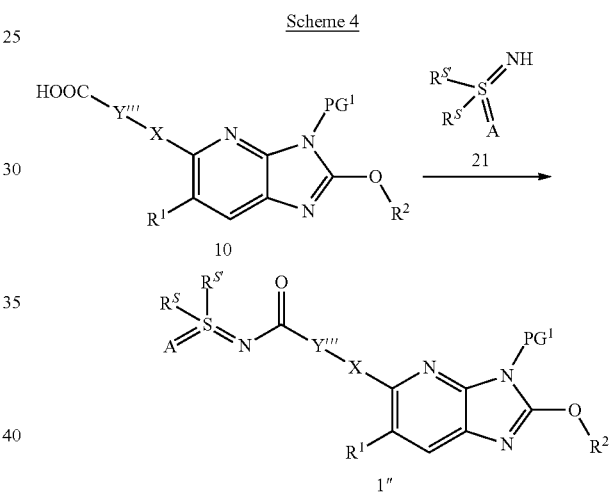

PG¹=as defined in Scheme 1,
A=O, $NR^N$,
$(R^S)(R^{S'})S(=A)=N-C(=O)-Y'''$ denotes a substructure of Y.

The reaction is preferably conducted with a coupling reagent, e.g. 1-[bis(dimethylamino)-methylene]-1H-1,2,3-triazolo[4,5-b]pyridinium-3-oxide hexafluorophosphate, (benzotriazo-1-yloxy)-tris(dimethylamino)-phosphonium hexafluorophosphate, (benzotriazol-1-yloxyl)-tris(pyrrolidino)-phosphonium hexafluorophosphate or 1-ethyl-(3-(3-dimethylamino)propyl)-carbodiimide hydrochloride in the presence of a base, e.g. N,N-diisopropylethylamine, triethylamine, pyridine or 4-(N,N-dimethylamino)pyridine in a suitable solvent, e.g. N,N-dimethylformamide or dichloromethane at 0 to 120° C.

Precursors 9 and 13 can be prepared by reaction of the corresponding alcohol derivatives 11 and 12 with intermediate 2 (Scheme 5) using essentially the same reaction conditions as described for Scheme 2 yielding compounds of the general formula 9 and 13 respectively; R¹, R², Y, and X have the meaning defined hereinbefore and hereinafter.

Scheme 5

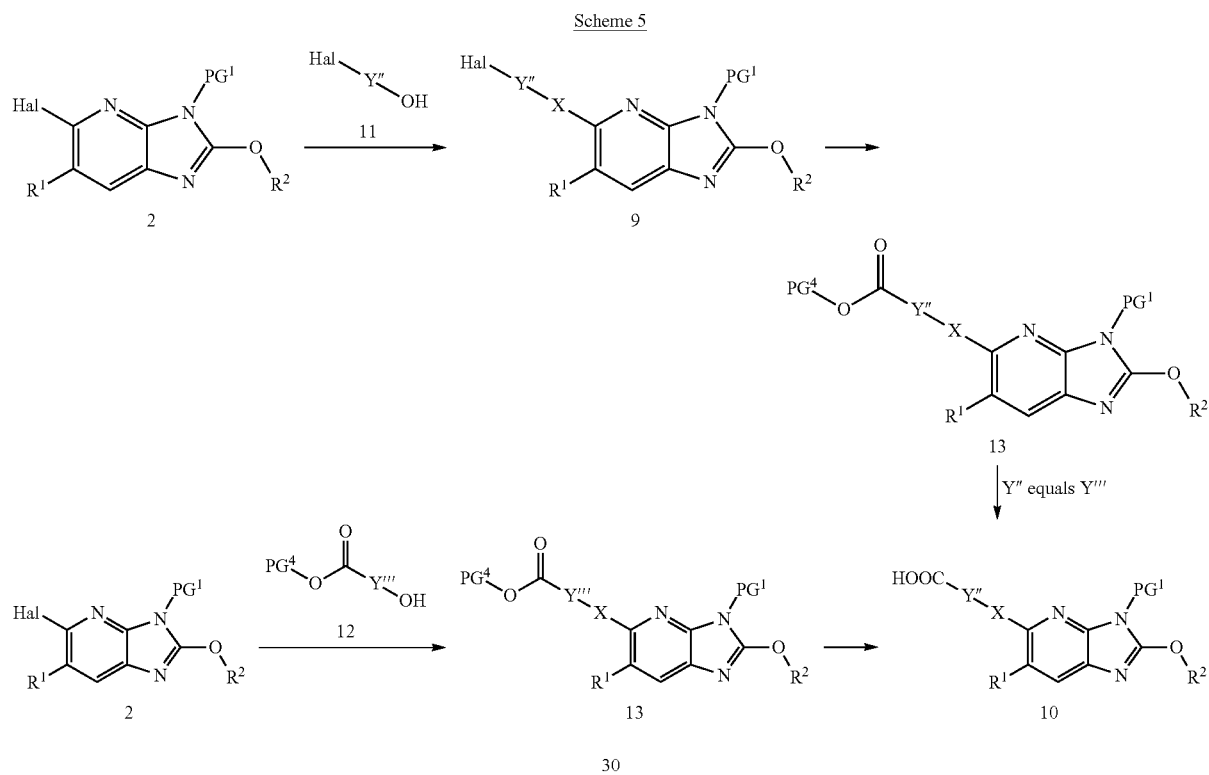

Hal=Cl, Br, I,
PG$^1$=as defined in Scheme 1,
PG$^4$=C$_{1-4}$ alkyl,
A=O, NR$^N$,
(R$^S$)(R$^{S'}$)S(=A)=N—Y″ denotes a substructure of Y,
(R$^S$)(R$^{S'}$)S(=A)=N—C(=O)—Y‴ denotes a substructure of Y,
R$^S$ and R$^{S'}$ have the meaning defined hereinbefore.

Derivatives of the general formula 9 can be converted into derivatives of the general formula 13 via carbonylation. The carbonylation is preferably performed under a carbonmonoxide atmosphere at elevated pressure in presence of a palladium derived catalyst e.g. palladium-(II)-acetate, a suitable ligand e.g. 1,1′-bis-(diphenylphosphino)-ferrocene, an appropriate base e.g. triethylamine in a suited solvent like methanol or ethanol at 20° C. to 100° C.

Cleavage of the acid protecting group PG$^4$ of compounds of the general formula 13 to release the acid functionality and to obtain compounds of the general formula 10 can be done under standard basic conditions such as LiOH, NaOH, KOH in a solvent such as water, methanol, tetrahydrofuran, 1,4-dioxane or mixtures thereof at −10 to 50° C.

Compounds 1, can alternatively be prepared from compounds of the general formula 14 (Scheme 6); R$^1$, R$^2$, R$^N$, R$^S$, X and Y have the meaning defined hereinbefore and hereinafter.

Scheme 6

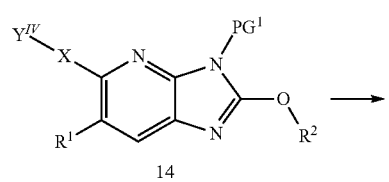

-continued

PG$^1$=as defined in Scheme 1,
Y$^{IV}$=(R$^S$)—S—Y″ wherein (R$^N$)=S(=O)(R$^S$)—Y″ denotes a substructure of Y.

As shown in scheme 6 the thioether moiety in Y$^{IV}$ in compounds of the general formula 14 can be transformed into a sulfoximine group by a two-step procedure. First step is the oxidation of the sulfur atom to a sulfoxide functionality under standard conditions such as meta-chloro-perbenzoic acid (MCPBA) in dichloromethane, sodium metaperiodate in methanol/water, or H$_2$O$_2$ in hexafluoro-isopropanol. Second step is the oxidation of the sulfoxide to the sulfoximine, which is preferentially performed with PhI (CH$_3$COO)$_2$ and CF$_3$C(O)NH$_2$ in the presence of MgO and a Rh-catalyst e.g. [Rh(CH$_3$COO)$_2$]$_2$, in dichloromethane or 1,2-dichloroethane at 0 to 60° C., which gives the trifluoracetyl-protected sulfoximine.

The trifluoroacetyl-protecting group can be cleaved under basic conditions such as K$_2$CO$_3$, NaOH, KOH, NaOMe, NaOEt, NaOtBu in a solvent such as water, methanol tetrahydrofuran, 1,4-dioxane or mixtures thereof at −10 to 50° C., to give the sulfoximine.

The protecting groups of compound 9 can be removed as described in scheme 1 to obtain compounds of the general formula 15 (scheme 7); PG$^1$, R$^1$, R$^2$, R$^{2*}$, R$^N$, R$^S$, R$^{S'}$, X, Y and Y″ have the meaning defined hereinbefore and hereinafter.

Scheme 7

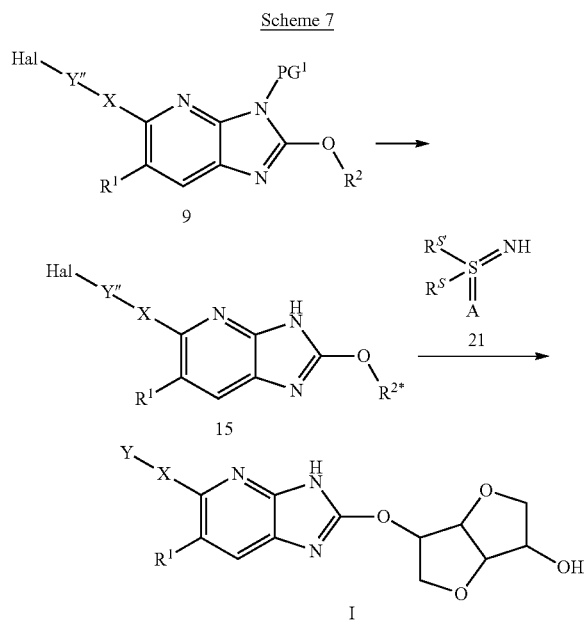

Hal=Cl, Br, I,
A=O, NR$^{N'}$,
(R$^S$)(R$^{S'}$)S(=A)=N—Y'' denotes a substructure of Y.

As further described in scheme 7 the coupling of the sulfoximine moiety or sulfodiimine moiety of the general formula 21 with compound 15 can be performed as described in scheme 3 to yield compounds of the general formula I.

The protecting groups of compound 10 can be removed as described in scheme 1 to obtain compounds of the general formula 16 (scheme 8); PG$^1$, R$^1$, R$^2$, R$^{2*}$, R$^{N'}$, R$^S$, R$^{S'}$, X, Y and Y''' have the meaning defined hereinbefore and hereinafter.

Scheme 8

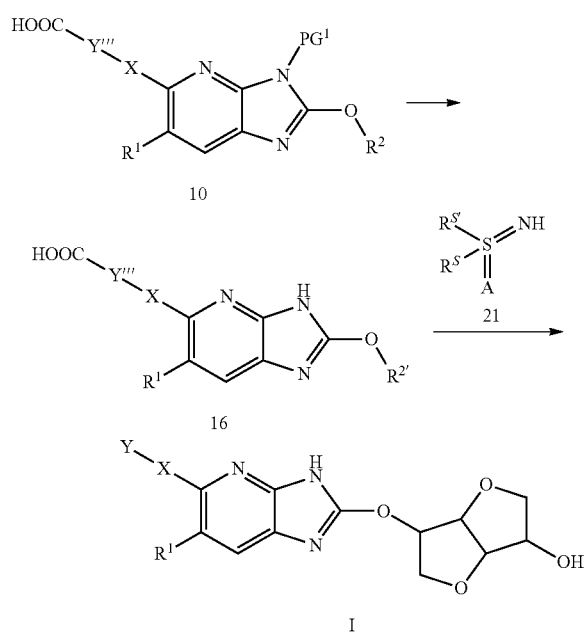

A=O, NR$^{N'}$,
(R$^S$)(R$^{S'}$)S(=A)=N—C(=O)—Y''' denotes a substructure of Y.

As further described in scheme 8 the coupling of the sulfoximine moiety or sulfondiimine moiety of the general formula 21 with compound 16 can be performed as described in scheme 4 to yield compounds of the general formula I.

Sulfoximines of the general formula 18, wherein R$^S$ and R$^{S'}$ have the meaning defined hereinbefore and hereinafter, may be prepared from the corresponding sulphoxides of the general formula 17, by reaction with o-mesitylenesulphonyl-hydroxylamine (MSH) in presence of a suitable solvent like dichlormethane.

Scheme 9

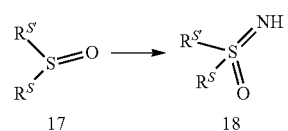

As shown in scheme 10 sulphoxides of the general formula 17, wherein R$^S$ and R$^{S'}$ have the meaning defined hereinbefore and hereinafter, may react with trifluoroacetamide in presence of PhI(OAc)$_2$, Rh$_2$(OAc)$_4$, and MgO in a suitable solvent like dichlormethane to form compounds of the general formula 19.

Scheme 10

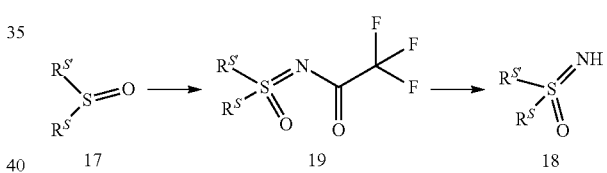

Sulfoximines of the general formula 18, wherein R$^S$ and R$^{S'}$ have the meaning defined hereinbefore and hereinafter, may be prepared by saponification of compounds of the general formula 19 (*Org. Lett.*, 2004, 6 (8), 1305-1307). Alternatively, other suitable protecting groups and iron as catalyst can be utilized (*Org. Lett.*, 2006, 8 (11), 2349-2352).

Sulfodiimines of the general formula 20, wherein R$^S$, R$^{S'}$ and R$^{N'}$ have the meaning defined hereinbefore and hereinafter, may be prepared according to literature procedures. For details see M. Haake in A. Senning: *The Chemistry of S,S-Diorgano-Sulfodiimides in Topics in Sulfur Chemistry*, Vol. 1, 185, Thieme Verlag, Stuttgart 1976 and references therein.

Scheme 11

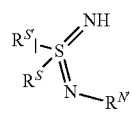

The synthetic routes presented may rely on the use of protecting groups. For example, potentially reactive groups present, such as hydroxy, carbonyl, carboxy, amino, alkylamino, or imino, may be protected during the reaction by conventional protecting groups which are cleaved again after the reaction. Suitable protecting groups for the respective functionalities and their removal are well known to the one skilled in the art and are described in the literature of organic synthesis.

The compounds of general formula I may be resolved into their enantiomers and/or diastereomers as mentioned below. Thus, for example, cis/trans mixtures may be resolved into their cis and trans isomers and racemic compounds may be separated into their enantiomers.

The cis/trans mixtures may be resolved, for example, by chromatography into the cis and trans isomers thereof. The compounds of general formula I which occur as racemates may be separated by methods known per se into their optical antipodes and diastereomeric mixtures of compounds of general formula I may be resolved into their diastereomers by taking advantage of their different physico-chemical properties using methods known per se, e.g. chromatography and/or fractional crystallization; if the compounds obtained thereafter are racemates, they may be resolved into the enantiomers as mentioned below.

The racemates are preferably resolved by column chromatography on chiral phases or by crystallization from an optically active solvent or by reacting with an optically active substance which forms salts or derivatives such as esters or amides with the racemic compound. Salts may be formed with enantiomerically pure acids for basic compounds and with enantiomerically pure bases for acidic compounds. Diastereomeric derivatives are formed with enantiomerically pure auxiliary compounds, e.g. acids, their activated derivatives, or alcohols. Separation of the diastereomeric mixture of salts or derivatives thus obtained may be achieved by taking advantage of their different physico-chemical properties, e.g. differences in solubility; the free antipodes may be released from the pure diastereomeric salts or derivatives by the action of suitable agents. Optically active acids commonly used for such a purpose as well as optically active alcohols applicable as auxiliary residues are known to those skilled in the art.

As mentioned above, the compounds of formula I may be converted into salts, particularly for pharmaceutical use into the pharmaceutically acceptable salts. As used herein, "pharmaceutically acceptable salts" refer to derivatives of the disclosed compounds wherein the parent compound is modified by making acid or base salts thereof.

The compounds according to the invention are advantageously also obtainable using the methods described in the examples that follow, which may also be combined for this purpose with methods known to the skilled man from the literature.

Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

The terms "compound(s) according to this invention", "compound(s) of formula (I)", "compound(s) of the invention" and the like denote the compounds of the formula (I) according to the present invention including their tautomers, stereoisomers and mixtures thereof and the salts thereof, in particular the pharmaceutically acceptable salts thereof, and the solvates and hydrates of such compounds, including the solvates and hydrates of such tautomers, stereoisomers and salts thereof.

The terms "treatment" and "treating" embrace both preventative, i.e. prophylactic, or therapeutic, i.e. curative and/or palliative, treatment. Thus the terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods of the present invention may be used for instance as therapeutic treatment over a period of time as well as for chronic therapy. In addition the terms "treatment" and "treating" comprise prophylactic treatment, i.e. a treatment of patients at risk to develop a condition mentioned hereinbefore, thus reducing said risk.

When this invention refers to patients requiring treatment, it relates primarily to treatment in mammals, in particular humans.

The term "therapeutically effective amount" means an amount of a compound of the present invention that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein.

The terms "modulated" or "modulating", or "modulate(s)", as used herein, unless otherwise indicated, refer to the activation of the AMP-activated protein kinase (AMPK) with one or more compounds of the present invention.

The terms "mediated" or "mediating" or "mediate", as used herein, unless otherwise indicated, refer to the (i) treatment, including prevention of the particular disease or condition, (ii) attenuation, amelioration, or elimination of one or more symptoms of the particular disease or condition, or (iii) prevention or delay of the onset of one or more symptoms of the particular disease or condition described herein.

The term "substituted" as used herein, means that any one or more hydrogens on the designated atom, radical or moiety is replaced with a selection from the indicated group, provided that the atom's normal valence is not exceeded, and that the substitution results in an acceptably stable compound.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

An asterisk may be used in sub-formulas to indicate the bond which is connected to the core molecule as defined.

The numeration of the atoms of a substituent starts with the atom which is closest to the core or to the group to which the substituent is attached.

For example, the term "3-carboxypropyl-group" represents the following substituent:

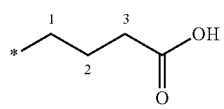

wherein the carboxy group is attached to the third carbon atom of the propyl group.

The terms "1-methylpropyl-", "2,2-dimethylpropyl-" or "cyclopropylmethyl-" group represent the following groups:

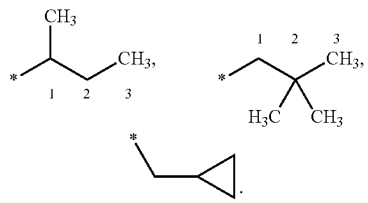

The asterisk may be used in sub-formulas to indicate the bond which is connected to the core molecule as defined.

Unless specifically indicated, throughout the specification and the appended claims, a given chemical formula or name shall encompass tautomers and all stereo, optical and geometrical isomers (e.g. enantiomers, diastereomers, E/Z isomers etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof.

Salts of other acids than those mentioned above which for example are useful for purifying or isolating the compounds of the present invention (e.g. trifluoro acetate salts) also comprise a part of the invention.

The term halogen generally denotes fluorine, chlorine, bromine and iodine.

The term "$C_{1-n}$-alkyl", wherein n is an integer from 1 to n, either alone or in combination with another radical denotes an acyclic, saturated, branched or linear hydrocarbon radical with 1 to n C atoms. For example the term $C_{1-4}$-alkyl embraces the radicals $H_3C—$, $H_3C—CH_2—$, $H_3C—CH_2—CH_2—$, $H_3C—CH(CH_3)—$, $H_3C—CH_2—CH_2—CH_2—$, $H_3C—CH_2—CH(CH_3)—$, $H_3C—CH(CH_3)—CH_2—$, and $H_3C—C(CH_3)_2—$.

Pharmacological Activity

The activity of the compounds of the invention may be demonstrated using the following in vitro AMPK activation assay:

AMPK α1β1γ1:

Recombinant human AMPK (containing subunits alpha1, beta1 and gamma1) was obtained from a baculovirus expression system. The 3 subunits were expressed together, affinity-purified via a GST-tag fused to the alpha 1 subunit and deep-frozen in storage buffer (50 mM Tris-HCl pH 8, 300 mM NaCl, 1 mM TCEP and 10% glycerol) at −80° C. until use.

The activity of the AMPK protein was determined using the ADP Glo® Luminescence Kinase test (Promega; V9103X). In this homogeneous test the amount of ADP formed by the kinase reaction is quantified by a luciferin-luciferase reaction using luminescence as read-out. The luminescence signal obtained correlates with the amount of ADP resulting from the kinase reaction and thus correlates with the activity of the protein kinase.

Method

The test compounds were dissolved in 100% DMSO at a concentration of 10 mM and in a first step diluted in DMSO to a concentration of 5 mM, followed by serial dilution steps in 100% DMSO. Dilution factor and number of dilution steps may vary. Typically 8 different concentrations by 1:5 dilutions were prepared, further dilutions of the substances were carried out with test buffer (20 mM Hepes (pH 7.0), 15 mM MgCl2, 0.025% BSA, 0.01% Brij 35) until a concentration was reached which was 5 times above the final test concentration. 2 µl aliquots of these dilutions were transferred into a 384-well Optiplate (Perkin Elmer, #6007290). Typically the start concentration for serial dilutions in the assay is 10 µM. Typically AMPK was diluted to 25 µg/ml in the test buffer and 4 µl of this dilution were used in the kinase test (final concentration of AMPK is 10 µg/ml in a total volume of 10 µl for the kinase reaction). Kinase concentrations may vary depending on activity of the preparation batches. After 10 minutes incubation at room temperature 4 µl of a mix containing 2.5 µM substrate (H-His-Met-Arg-Ser-Ala-Met-Ser-Gly-Leu-His-Leu-Val-Lys-Arg-Arg-OH Trifluoroacetate salt/HMRSAMSGLHLVKRR from Bachem, Cat. No. H5938) and 75 µM ATP in test buffer were added to each well and the incubation was continued for 60 minutes at room temperature.

Positive controls are the reaction mixtures that contain no test substance; negative controls (blanks) are reaction mixtures that contain no AMPK enzyme.

After 60 minutes, 10 µl ADP-Glo® solution (ADP-Glo Reagent #V912B Promega) (heated to room temperature) were added to each well and incubation was continued for 40. minutes. Then 20 µl Kinase detection mix (Detection Buffer #V913B Promega; Kinase Detection Substrate #V914B Promega) were added and incubated for additional 40 minutes at room temperature.

All incubations were done in sealed plates in the dark.

The plates were read with an Envision Luminescence Reader (Perkin-Elmer).

Data Evaluation and Calculation:

The output file of the reader is a csv file that contains the well number and measured RLU. For data evaluation and calculation, the measurement of the negative control was set as 0% control and the measurement of the positive control was set as 100% control. Based on this values the % value for the measurement of each substance concentration was calculated using Assay Explorer software (Accelrys). Activating compounds achieve % of control values above 100%. The $IC_{50}$ values were calculated from the % control values using Assay Explorer software. Calculation: [y=(a−d)/(1+ (x/c)^b)+d], a=low value, d=high value; x=conc M; c=IC50 M; b=hill; y=% ctrl. The maximal achievable activation of a compound in the tested concentration range is reported as percent of control max (PoCmax).

The compounds according to the invention typically have $EC_{50}$ values in the range from about 0.1 nM to about 10 µM, preferably less than 1 µM, more preferably less than 500 nM.

AMPK α1β2γ2:

The in vitro AMPK α1β2γ2 activation assay is carried out with recombinant human AMPK (containing subunits alpha1, beta2 and gamma2), in full analogy as described above for AMPK α1β1γ1.

AMPK α2β1γ1:

The in vitro AMPK α2β1γ1 activation assay is carried out with recombinant human AMPK (containing subunits alpha2, beta1 and gamma1), in full analogy as described above for AMPK α1β1γ1.

AMPK α2β2γ2:

The in vitro AMPK α2β2γ2 activation assay is carried out with recombinant human AMPK (containing subunits alpha2, beta2 and gamma2), in full analogy as described above for AMPK α1β1γ1.

In view of their ability to modulate the activity of the AMP-activated protein kinase (AMPK), in particular an agonistic activity, the compounds of general formula I according to the invention, including the corresponding salts thereof, are theoretically suitable for the treatment of all those diseases or conditions which may be affected or which are mediated by the activation of the AMP-activated protein kinase (AMPK).

Accordingly, the present invention relates to a compound of general formula I as a medicament.

Furthermore, the present invention relates to the use of a compound of general formula I or a pharmaceutical composition according to this invention for the treatment and/or prevention of diseases or conditions which are mediated by the activation of the AMP-activated protein kinase (AMPK) in a patient, preferably in a human.

In yet another aspect the present invention relates to a method for treating a disease or condition mediated by the activation of the AMP-activated protein kinase (AMPK) in a mammal that includes the step of administering to a patient, preferably a human, in need of such treatment a therapeutically effective amount of a compound or a pharmaceutical composition of the present invention.

Diseases and conditions mediated by agonists of the AMP-activated protein kinase (AMPK) embrace metabolic diseases or conditions. According to one aspect the compounds and pharmaceutical compositions of the present invention are particularly suitable for treating diabetes mellitus, in particular Type 2 diabetes, Type 1 diabetes, complications of diabetes (such as e.g. retinopathy, nephropathy or neuropathies, diabetic foot, ulcers or macroangiopathies), metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, oedema and hyperuricaemia.

The compounds and pharmaceutical compositions of the present invention are also suitable for preventing beta-cell degeneration such as e.g. apoptosis or necrosis of pancreatic beta cells. The compounds and pharmaceutical compositions of the present invention are also suitable for improving or restoring the functionality of pancreatic cells, and also for increasing the number and size of pancreatic beta cells.

Therefore according to another aspect the invention relates to compounds of formula I and pharmaceutical compositions according to the invention for use in preventing, delaying, slowing the progression of and/or treating metabolic diseases, particularly in improving the glycaemic control and/or beta cell function in the patient.

In another aspect the invention relates to compounds of formula I and pharmaceutical compositions according to the invention for use in preventing, delaying, slowing the progression of and/or treating type 2 diabetes, overweight, obesity, complications of diabetes and associated pathological conditions.

In addition the compounds and pharmaceutical compositions according to the invention are suitable for use in one or more of the following therapeutic processes:

for preventing, delaying, slowing the progression of or treating metabolic diseases, such as for example type 1 diabetes, type 2 diabetes, insufficient glucose tolerance, insulin resistance, hyperglycaemia, hyperlipidaemia, hypercholesterolaemia, dyslipidaemia, syndrome X, metabolic syndrome, obesity, high blood pressure, chronic systemic inflammation, retinopathy, neuropathy, nephropathy, atherosclerosis, endothelial dysfunction or bone-related diseases (such as osteoporosis, rheumatoid arthritis or osteoarthritis);

for improving glycaemic control and/or reducing fasting plasma glucose, postprandial plasma glucose and/or the glycosylated haemoglobin HbA1c;

for preventing, delaying, slowing or reversing the progression of disrupted glucose tolerance, insulin resistance and/or metabolic syndrome to type 2 diabetes;

for preventing, delaying, slowing the progression of or treating a condition or a disease selected from among the complications of diabetes, such as for example retinopathy, nephropathy or neuropathies, diabetic foot, ulcers or macroangiopathies;

for reducing weight or preventing weight gain or assisting weight loss;

for preventing or treating the degradation of pancreatic beta cells and/or improving and/or restoring the functionality of pancreatic beta cells and/or restoring the functionality of pancreatic insulin secretion;

for maintaining and/or improving insulin sensitivity and/or preventing or treating hyperinsulinaemia and/or insulin resistance.

In particular, the compounds and pharmaceutical compositions according to the invention are suitable for the treatment of obesity, diabetes (comprising type 1 and type 2 diabetes, preferably type 2 diabetes mellitus) and/or complications of diabetes (such as for example retinopathy, nephropathy or neuropathies, diabetic foot, ulcers or macroangiopathies).

The compounds according to the invention are most particularly suitable for treating type 2 diabetes mellitus.

The dose range of the compounds of general formula I applicable per day is usually from 0.001 to 10 mg per kg body weight, for example from 0.01 to 8 mg per kg body weight of the patient. Each dosage unit may conveniently contain from 0.1 to 1000 mg, for example 0.5 to 500 mg.

The actual therapeutically effective amount or therapeutic dosage will of course depend on factors known by those skilled in the art such as age and weight of the patient, route of administration and severity of disease. In any case the compound or composition will be administered at dosages and in a manner which allows a therapeutically effective amount to be delivered based upon patient's unique condition.

The compounds, compositions, including any combinations with one or more additional therapeutic agents, according to the invention may be administered by oral, transdermal, inhalative, parenteral or sublingual route. Of the possible methods of administration, oral or intravenous administration is preferred.

Pharmaceutical Compositions

Suitable preparations for administering the compounds of formula I, optionally in combination with one or more further therapeutic agents, will be apparent to those with ordinary skill in the art and include for example tablets, pills, capsules, suppositories, lozenges, troches, solutions, syrups, elixirs, sachets, injectables, inhalatives and powders etc. Oral formulations, particularly solid forms such as e.g. tablets or capsules are preferred. The content of the pharmaceutically active compound(s) is advantageously in the range from 0.1 to 90 wt.-%, for example from 1 to 70 wt.-% of the composition as a whole.

Suitable tablets may be obtained, for example, by mixing one or more compounds according to formula I with known excipients, for example inert diluents, carriers, disintegrants, adjuvants, surfactants, binders and/or lubricants. The tablets may also consist of several layers. The particular excipients, carriers and/or diluents that are suitable for the desired preparations will be familiar to the skilled man on the basis of his specialist knowledge. The preferred ones are those that are suitable for the particular formulation and method of administration that are desired. The preparations or formulations according to the invention may be prepared using methods known per se that are familiar to the skilled man, such as for example by mixing or combining at least one compound of formula I according to the invention, or a pharmaceutically acceptable salt of such a compound, and one or more excipients, carriers and/or diluents.

Combination Therapy

The compounds of the invention may further be combined with one or more, preferably one additional therapeutic agent. According to one embodiment the additional therapeutic agent is selected from the group of therapeutic agents useful in the treatment of diseases or conditions described hereinbefore, in particular associated with metabolic diseases or conditions such as for example diabetes mellitus, obesity, diabetic complications, hypertension, hyperlipidemia. Additional therapeutic agents which are suitable for such combinations include in particular those which for example potentiate the therapeutic effect of one or more active substances with respect to one of the indications mentioned and/or which allow the dosage of one or more active substances to be reduced.

Therefore a compound of the invention may be combined with one or more additional therapeutic agents selected from the group consisting of antidiabetic agents, agents for the treatment of overweight and/or obesity and agents for the treatment of high blood pressure, heart failure and/or atherosclerosis.

Antidiabetic agents are for example metformin, sulphonylureas, nateglinide, repaglinide, thiazolidinediones, PPAR-(alpha, gamma or alpha/gamma) agonists or modulators, alpha-glucosidase inhibitors, DPPIV inhibitors, SGLT2-inhibitors, insulin and insulin analogues, GLP-1 and GLP-1 analogues or amylin and amylin analogues, cycloset, 11β-HSD inhibitors. Other suitable combination partners are inhibitors of protein tyrosinephosphatase 1, substances that affect deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase, alpha2-antagonists, CCR-2 antagonists or glucokinase activators. One or more lipid lowering agents are also suitable as combination partners, such as for example HMG-CoA-reductase inhibitors, fibrates, nicotinic acid and the derivatives thereof, PPAR-(alpha, gamma or alpha/gamma) agonists or modulators, PCSK9 inhibitors, PPAR-delta agonists, ACAT inhibitors or cholesterol absorption inhibitors such as, bile acid-binding substances such as, inhibitors of ileac bile acid transport, MTP inhibitors, or HDL-raising compounds such as CETP inhibitors or ABC1 regulators.

Therapeutic agents for the treatment of overweight and/or obesity are for example antagonists of the cannabinoid1 receptor, MCH-1 receptor antagonists, MC4 receptor agonists, NPY5 or NPY2 antagonists, β3-agonists, leptin or leptin mimetics, agonists of the 5HT2c receptor.

Therapeutic agents for the treatment of high blood pressure, chronic heart failure and/or atherosclerosis are for example A-II antagonists or ACE inhibitors, ECE inhibitors, diuretics, βblockers, Ca-antagonists, centrally acting antihypertensives, antagonists of the alpha-2-adrenergic receptor, inhibitors of neutral endopeptidase, thrombocyte aggregation inhibitors and others or combinations thereof are suitable. Angiotensin II receptor antagonists are preferably used for the treatment or prevention of high blood pressure and complications of diabetes, often combined with a diuretic such as hydrochlorothiazide.

The dosage for the combination partners mentioned above is usually ⅕ of the lowest dose normally recommended up to 1/1 of the normally recommended dose.

Preferably, compounds of the present invention and/or pharmaceutical compositions comprising a compound of the present invention optionally in combination with one or more additional therapeutic agents are administered in conjunction with exercise and/or a diet.

Therefore, in another aspect, this invention relates to the use of a compound according to the invention in combination with one or more additional therapeutic agents described hereinbefore and hereinafter for the treatment of diseases or conditions which may be affected or which are mediated by the activation of the AMP-activated protein kinase (AMPK), in particular diseases or conditions as described hereinbefore and hereinafter.

In yet another aspect the present invention relates a method for treating a disease or condition mediated by the activation of the AMP-activated protein kinase (AMPK) in a patient that includes the step of administering to the patient, preferably a human, in need of such treatment a therapeutically effective amount of a compound of the present invention in combination with a therapeutically effective amount of one or more additional therapeutic agents described in hereinbefore and hereinafter, The use of the compound according to the invention in combination with the additional therapeutic agent may take place simultaneously or at staggered times.

The compound according to the invention and the one or more additional therapeutic agents may both be present together in one formulation, for example a tablet or capsule, or separately in two identical or different formulations, for example as a so-called kit-of-parts.

Consequently, in another aspect, this invention relates to a pharmaceutical composition which comprises a compound according to the invention and one or more additional therapeutic agents described hereinbefore and hereinafter, optionally together with one or more inert carriers and/or diluents.

Other features and advantages of the present invention will become apparent from the following more detailed Examples which illustrate, by way of example, the principles of the invention.

EXAMPLES

Preliminary Remarks:

As a rule, $^1$H-NMR and/or mass spectra have been obtained for the compounds prepared. The $R_f$ values are determined using Merck silica gel 60 $F_{254}$ plates and UV light at 254 nm.

The terms "ambient temperature" and "room temperature" are used interchangeably and designate a temperature of about 20° C.

List of Abbreviations aq. aqueous
$BH_3$*$Me_2$S borane dimethylsulfide complex
° C. degree Celsius
DA diode array
DBU diazabicyclo[5.4.0]undec-7-ene
DCC N,N'-dicyclohexylcarbodiimide
DCM dichloromethane
DIPEA diisopropylethylamine
DMAP 4-dimethylaminopyridine
DMF N,N-dimethylformamide
ESI-MS electrospray ionisation mass spectrometry
EtOAc ethyl acetate
eq equivalent
FC flash-chromatography, $SiO_2$ is used if no further details given
h hour
HCl hydrogenchloride
HATU [dimethylamino-(1,2,3-triazolo[4,5-b]pyridin-3-yloxy)-methylene]-dimethyl-ammonium hexafluorophosphate
HPLC high performance liquid chromatography
L liter
LiHMDS lithium Hexamethyldisilazide
m/z mass-to-charge ratio
MeOH methanol
min minute
mL milliliter
MS mass spectrum
n.d. not determined
$NH_4OH$ solution of $NH_3$ in water
Pd-PEPPSI-IPent™ dichloro[1,3-bis(2,6-Di-3-pentylphenyl)imidazol-2-ylidene](3-chloropyridyl)palladium(II)
psi pound per square inch
RT room temperature (about 20° C.)
SEM 2-(trimethylsilyl)ethoxymethyl
Sol solvent
TBTU [(benzotriazol-1-yloxy)-dimethylamino-methylene]-dimethyl-ammonium tetrafluoroborate
TEA triethyl amine
Teoc 2-trimethylsilylethyl carbamate
TF/TFA trifluoroacetic acid
TFAA trifluoroacetic acid anhydride
THF tetrahydrofuran
$t_R$ retention time in minutes Analytical HPLC parameters employed for characterization of products (TFA denotes trifluoroacetic acid and FA denotes formic acid):

| Method Name: method 1 | | | | |
|---|---|---|---|---|
| Column: Sunfire C18_3.0 × 30 mm, 2.5 μm | | | | |
| Column producer: Waters | | | | |
| Gradient/Solvent Time [min] | % Sol [$H_2O$ 0.1% TFA] | % Sol [Acetonitrile] | Flow [ml/min] | Temp [° C.] |
| 0.0 | 98.0 | 2.0 | 2.0 | 60.0 |
| 1.2 | 0.0 | 100.0 | 2.0 | 60.0 |
| 1.4 | 0.0 | 100.0 | 2.0 | 60.0 |

| Method Name: method 2 | | | | |
|---|---|---|---|---|
| Column: XBridge C18_3.0 × 30 mm, 2.5 μm | | | | |
| Column producer: Waters | | | | |
| Description: | | | | |
| Gradient/Solvent Time [min] | % Sol [$H_2O$ 0.1% $NH_4OH$] | % Sol [Acetonitrile] | Flow [ml/min] | Temp [° C.] |
| 0.0 | 98.0 | 2.0 | 2.0 | 60.0 |
| 1.2 | 0.0 | 100.0 | 2.0 | 60.0 |
| 1.4 | 0.0 | 100.0 | 2.0 | 60.0 |

| Method Name: method 3 | | | | |
|---|---|---|---|---|
| Column: Xbridge BEH C18, 2.1 × 30 mm, 1.7 μm | | | | |
| Column Supplier: Waters | | | | |
| Gradient/Solvent Time [min] | % Sol [$H_2O$, 0.1% TFA] | % Sol [Acetonitril] | Flow [ml/min] | Temp [° C.] |
| 0.0 | 99 | 1 | 1.6 | 60 |
| 0.02 | 99 | 1 | 1.6 | 60 |
| 1.00 | 0 | 100 | 1.6 | 60 |
| 1.10 | 0 | 100 | 1.6 | 60 |

| Methoden Name: method 4 | | | | |
|---|---|---|---|---|
| Column: XBridge C18, 4.6 × 30 mm, 3.5 μm | | | | |
| Column Supplier: Waters | | | | |
| Gradient/Solvent Time [min] | % Sol [$H_2O$, 0.1% NH3] | % Sol [ACN] | Flow [ml/min] | Temp [° C.] |
| 0.0 | 50 | 50 | 4 | 60 |
| 0.15 | 50 | 50 | 4 | 60 |
| 1.5 | 0 | 100 | 4 | 60 |
| 1.85 | 0 | 100 | 4 | 60 |

| Method Name: method 5 | | | | |
|---|---|---|---|---|
| Column: Stable Bond, 3 × 30 mm, 1.8 μm | | | | |
| Column Supplier: Agilent | | | | |
| Gradient/Solvent Time [min] | % Sol [$H_2O$, 0.1% TFA] | % Sol [Acetonitril] | Flow [ml/min] | Temp [° C.] |
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

| Method Name: method 6 |||||
| Column: Stable Bond, 3 × 30 mm, 1.8 μm |||||
| Column Supplier: Agilent |||||
| Gradient/Solvent Time [min] | % Sol [H₂O, 0.1% TFA] | % Sol [Acetonitril] | Flow [ml/min] | Temp [° C.] |
| --- | --- | --- | --- | --- |
| 0.00 | 50 | 50 | 2.2 | 60 |
| 0.20 | 50 | 50 | 2.2 | 60 |
| 1.20 | 0 | 100 | 2.2 | 60 |
| 1.25 | 0 | 100 | 3 | 60 |
| 1.40 | 0 | 100 | 3 | 60 |

| Method Name: method 7 |||||
| Column: Sunfire, 3 × 30 mm, 2.5 μm |||||
| Column Supplier: Waters |||||
| Gradient/Solvent Time [min] | % Sol [H₂O, 0.1% TFA] | % Sol [Acetonitril] | Flow [ml/min] | Temp [° C.] |
| --- | --- | --- | --- | --- |
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

The Examples that follow are intended to illustrate the present invention without restricting it:

Intermediate 1

2-{[(3R,3aR,6R,6aS)-6-[(tert-butyldimethylsilyl)oxy]-hexahydrofuro[3,2-b]furan-3-yl]oxy}-6-chloro-5-iodo-3-{[2-(trimethylsilyl)ethoxy]methyl}-3H-imidazo[4,5-b]pyridine

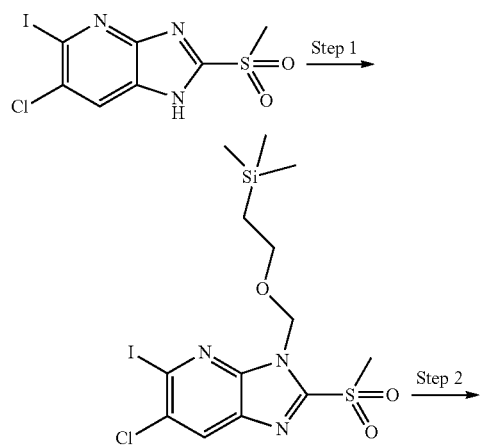

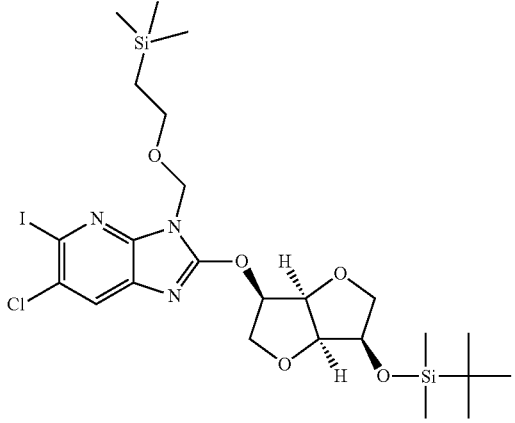

Step 1: 6-chloro-5-iodo-2-methanesulfonyl-3-{[2-(trimethylsilyl)ethoxy]methyl}-3H-imidazo[4,5-b]pyridine The synthesis of 6-chloro-5-iodo-2-methanesulfonyl-3-{[2-(trimethylsilyl)ethoxy]-methyl}-3H-imidazo-[4,5-b]pyridine is performed analogous to the described procedure in WO2014/031515.

Step 2: 2-{[(3R,3aR,6R,6aS)-6-[(tert-butyldimethylsilyl)oxy]-hexahydrofuro[3,2-]furan-3-yl]oxy}-6-chloro-5-iodo-3-{[2-(trimethylsilyl)ethoxy]methyl}-3H-imidazo[4,5-b]-pyridine 12.0 g (46.1 mmol) (3R,3aR,6R,6aS)-6-[(tert-butyldimethylsilyl)oxy]-hexahydrofuro-[3,2-b]furan-3-ol and 18.7 g (123.0 mmol) 1,8-diazabicyclo[5.4.0]undec-7-ene (DBU) are added to 15.0 g (30.7 mmol) 6-chloro-5-iodo-2-methanesulfonyl-3-{[2-(trimethylsilyl)ethoxy]methyl}-3H-imidazo[4,5-b]pyridine in 100 mL N,N-dimethylformamide (DMF) and stirred at RT for 2 h. The mixture is partitioned between water and ethylacetate and the organic phase is washed with brine and dried (MgSO₄). The solvents are evaporated in vacuo and the residue is chromatographed on silica gel (cyclohexane/ethyl acetate 80:20→0:100) to give the title compound. LC (method 7): $t_R$=1.29 min; Mass spectrum (ESI⁺): m/z=668 [M+H]⁺.

Intermediate 2

2-{[(3R,3aR,6R,6aS)-6-[(tert-butyldimethylsilyl)oxy]-hexahydrofuro[3,2-b]furan-3-yl]oxy}-5-[(4-bromo-2,6-difluorophenyl)methoxy]-6-chloro-3-{[2-(trimethylsilyl)ethoxy]-methyl}-3H-imidazo[4,5-b]pyridine

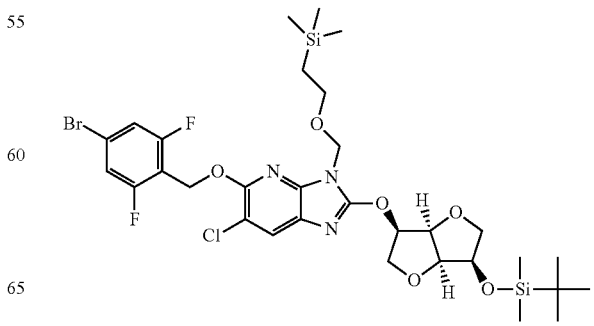

Under an argon atmosphere 1.0 g (4.49 mmol) (4-bromo-2,6-difluorophenyl)-methanol, 1.46 g (4.49 mmol) cesium carbonate, 0.08 g (0.45 mmol) 1,10-phenanthroline and 0.04 g (0.23 mmol) copper-(I)-iodide are added to 1.5 g (2.25 mmol) 2-{[(3R,3aR,6R,6aS)-6-[(tert-butyldimethylsilyl)oxy]-hexahydrofuro[3,2-]furan-3-yl]oxy}-6-chloro-5-iodo-3-{[2-(trimethylsilyl)ethoxy]methyl}-3H-imidazo[4,5-b]-pyridine in 15 mL toluene. The reaction mixture is stirred at 100° C. over night in a sealed tube. The reaction mixture is filtered and evaporated to dryness. The residue is chromatographed on silica gel (cyclohexane/ethyl acetate) to give the title compound. LC (method 4): $t_R$=1.54 min; Mass spectrum (ESI$^+$): m/z=762, 764 [M+H]$^+$.

Intermediate 3

(3R,3aR,6R,6aR)-6-({5-[(4-bromo-2,6-difluorophenyl)methoxy]-6-chloro-3H-imidazo-[4,5-b]pyridin-2-yl}oxy)-hexahydrofuro[3,2-b]furan-3-ol

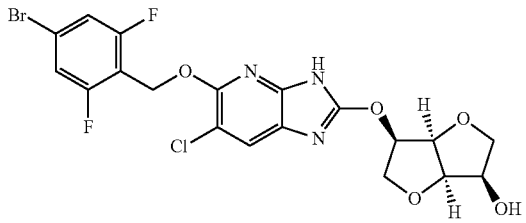 [SMILES: O[C@@H]1CO[C@H]2[C@@H]1OC[C@H]2Oc1nc2cc(Cl)c(OCc3c(F)cc(Br)cc3F)nc2[nH]1]

5 mL Trifluoracetic acid is added to 0.8 g (1.05 mmol) 2-{[(3R,3aR,6R,6aS)-6-[(tert-butyldimethylsilyl)oxy]-hexahydrofuro[3,2-b]furan-3-yl]oxy}-5-[(4-bromo-2,6-difluorophenyl)methoxy]-6-chloro-3-{[2-(trimethylsilyl)ethoxy]methyl}-3H-imidazo[4,5-b]-pyridine in 5 mL dichloromethane and the reaction mixture is stirred at room temperature overnight. The reaction mixture is concentrated under reduced pressure and the residue is purified by silica chromatography. LC (method 5): $t_R$=1.02 min; Mass spectrum (ESI$^+$): m/z=518, 520 [M+H]$^+$.

Intermediate 4

2-(trimethylsilyl)ethyl N-{[3,5-difluoro-4-(hydroxymethyl)phenyl](methyl)oxo-$\lambda^6$-sulfanylidene}carbamate Step 1: (2,6-difluoro-4-methanesulfinylphenyl)methanol 0.65 g (2.63 mmol) 3-Chloro-benzenecarboperoxoic acid are added to 0.50 g (2.63 mmol) [2,6-difluoro-4-(methylsulfanyl)phenyl]methanol in 12 mL dichloromethane. After 3 h of stirring at room temperature the reaction mixture is filtered over Alox. After washing Alox with DCM/MeOH (4:1) the filtrate is concentrated to dryness and used without further purification. LC (method 5): $t_R$=0.53 min; Mass spectrum (ESI$^+$): m/z=207 [M+H]$^+$.

Step 2: N-{[3,5-difluoro-4-(hydroxymethyl)phenyl](methyl)oxo-$\lambda^6$-sulfanylidene}-2,2,2-trifluoroacetamide To 0.54 g (2.62 mmol) (2,6-difluoro-4-methanesulfinylphenyl)methanol in 15 mL dichloromethane 0.59 g (5.24 mmol) 2,2,2-trifluoroacetamide, 0.43 g (10.47 mmol) magnesiumoxide, 1.27 g (3.93 mmol) iodosobenzene diacetate and subsequently 0.12 g (0.26 mmol) rhodium-II-acetate is added. The reaction mixture is stirred at RT overnight and filtered. The filtrate is evaporated to dryness and the residue is used without further purification. LC (method 5): $t_R$=0.84 min; Mass spectrum (ESI$^+$): m/z=310 [M+H]$^+$.

Step 3: [3,5-difluoro-4-(hydroxymethyl)phenyl](imino)methyl-$\lambda^6$-sulfanone 0.83 g (2.62 mmol) N-{[3,5-difluoro-4-(hydroxymethyl)phenyl](methyl)oxo-$\lambda^6$ sulfanylidene}-2,2,2-trifluoroacetamide and 0.43 g (3.14 mmol) potassium carbonate in 10 mL methanol are stirred at room temperature for 5 h. Dichloromethane is added to the reaction mixture and filtered with silica gel. The silica gel is washed with dichlormethane/methanol (1:1) and the filtrate is concentrated to dryness under reduced pressure. The residue is used without further purification. LC (method 5): $t_R$=0.26 min; Mass spectrum (ESI$^+$): m/z=222 [M+H]$^+$.

Step 4: 2-(trimethylsilyl)ethyl N-{[3,5-difluoro-4-(hydroxymethyl)phenyl](methyl)oxo-$\lambda^6$-sulfanylidene}carbamate 0.30 g (1.36 mmol) [3,5-difluoro-4-(hydroxymethyl)phenyl](imino)methyl-$\lambda^6$-sulfanone, 0.42 g (1.47 mmol) 2-(trimethylsilyl)ethyl-4-nitrophenylcarbonate and catalytic

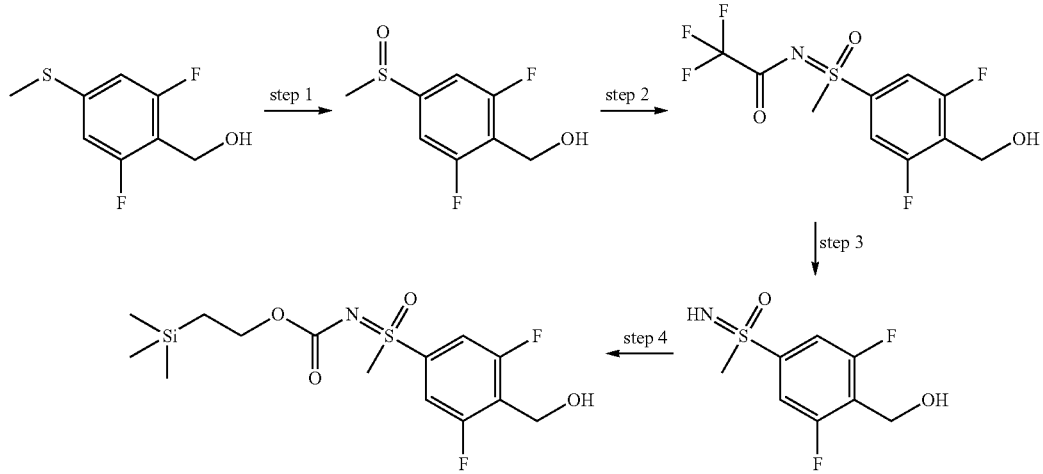

amount of DMAP in 10 mL tetrahydrofuran (THF) are stirred under reflux for 2 h. The reaction mixture is concentrated to dryness and the residue is purified by silica chromatography. The product containing fractions are combined and evaporated to dryness. LC (method 5): $t_R$=1.06 min; Mass spectrum (ESI$^+$): m/z=366 [M+H]$^+$.

Intermediate 5

2-(trimethylsilyl)ethyl N-[(4-{[(2-{[(3R,3aR,6R,6aS)-6-[(tert-butyldimethylsilyl)oxy]-hexahydrofuro[3,2-b]furan-3-yl]oxy}-6-chloro-3-{[2-(trimethylsilyl)ethoxy]methyl}-3H-imidazo[4,5-b]pyridin-5-yl)oxy]methyl}-3,5-difluorophenyl)(methyl)oxo-λ$^6$-sulfanylidene]carbamate mmol) cesium carbonate, 19 mg (0.11 mmol) 1,10-phenanthroline and 10 mg (0.05 mmol) copper-(I)-iodide are added to 0.35 g (0.52 mmol) 2-{[(3R,3aR,6R,6aS)-6-[(tert-butyldimethylsilyl)oxy]-hexahydrofuro[3,2-]furan-3-yl]oxy}-6-chloro-5-iodo-3-{[2-(trimethylsilyl)ethoxy]methyl}-3H-imidazo[4,5-b]pyridine in 4 mL toluene. The reaction mixture is stirred at 100° C. overnight in a sealed tube. The reaction mixture is filtered and evaporated to dryness. The residue is chromatographed on silica gel (cyclohexane/ethyl acetate) to give the title compound. LC (method 6): $t_R$=1.30 min Intermediate 6

{[(4-{[(2-{[(3R,3aR,6R,6aS)-6-[(tert-butyldimethylsilyl)oxy]-hexahydrofuro[3,2-b]furan-3-yl]oxy}-6-.

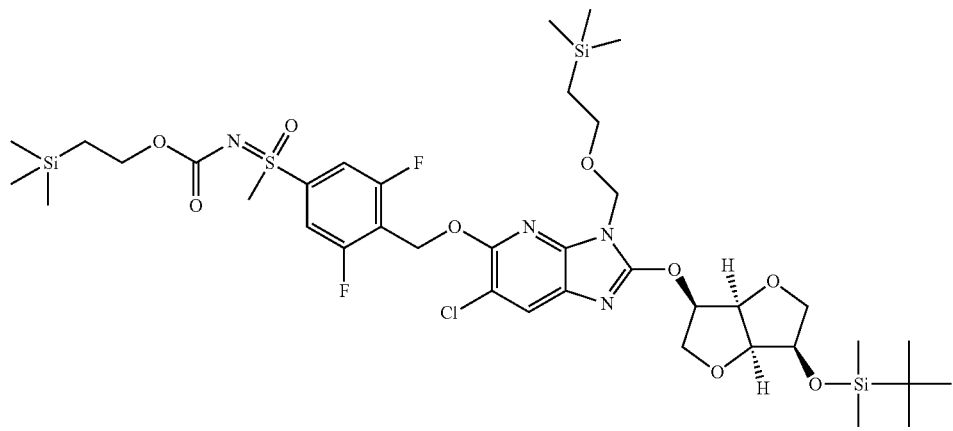 [SMILES: CC(C)(C)[Si](C)(C)O[C@@H]1CO[C@H]2[C@@H]1OC[C@H]2Oc1nc2cc(Cl)c(OCc3c(F)cc(S(C)(=O)=NC(=O)OCC[Si](C)(C)C)cc3F)nc2n1COCC[Si](C)(C)C]

Under an argon atmosphere 0.19 g (0.52 mmol) 2-(trimethylsilyl)ethyl N-{[3,5-difluoro-4-(hydroxymethyl)phenyl](methyl)oxo-λ$^6$-sulfanylidene}carbamate, 0.34 g (1.05 chloro-3-{[2-(trimethylsilyl)ethoxy]methyl}-3H-imidazo[4,5-b]pyridin-5-yl)oxy]methyl}-3,5-difluorophenyl)methyl]imino}dimethyl-λ$^6$-sulfanone

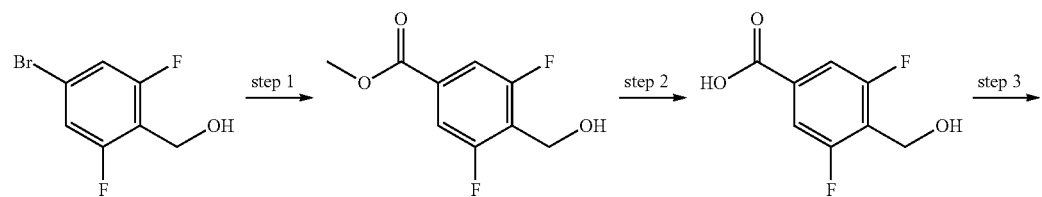

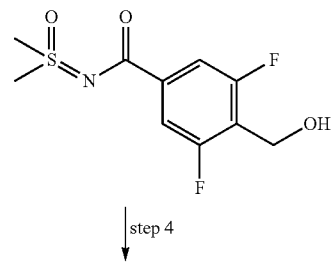

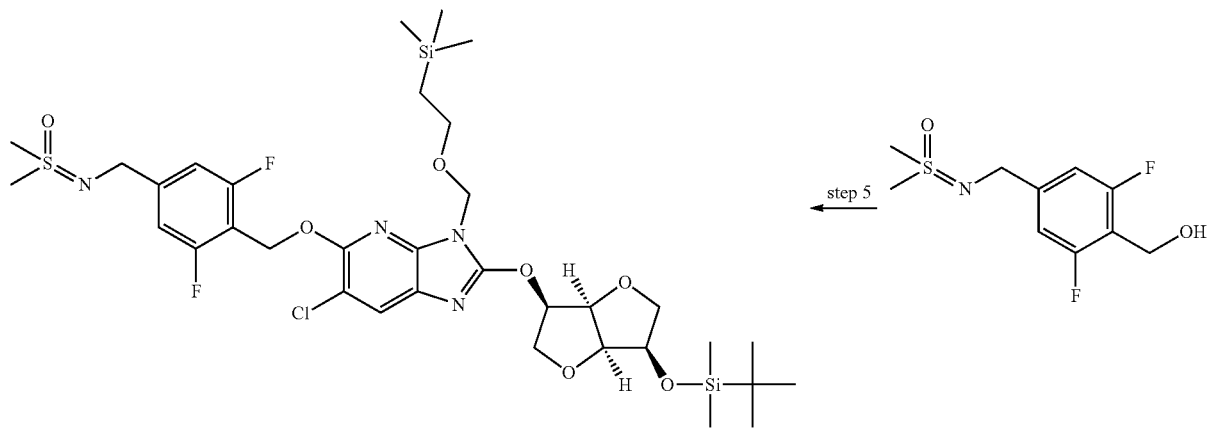

Step 1: methyl 3,5-difluoro-4-(hydroxymethyl)benzoate

In a carbonmonoxide atmosphere at 6 bar 1.0 g (4.48 mmol) (4-bromo-2,6-difluorophenyl)methanol, 0.25 g (0.45 mmol) 1,1'-bis-(diphenylphosphino)-ferrocen, 0.10 g (0.45 mmol) palladium-(II)-acetate and 1.26 mL (8.97 mmol) triethylamine in 20 mL methanol are heated at 80° C. for 4h. The reaction mixture is filtered and evaporated to dryness. The residue is used without further purification. LC (method 5): $t_R$=0.79 min; Mass spectrum (ESI$^+$): m/z=203 [M+H]$^+$.

Step 2: 3,5-difluoro-4-(hydroxymethyl)benzoic acid 1.00 g (4.95 mmol) methyl 3,5-difluoro-4-(hydroxymethyl)benzoate and 0.24 g (9.89 mmol) lithiumhydroxide in 10 mL tetrahydrofuran and 5 mL methanol are stirred overnight at room temperature. After addition of some water, the pH of the reaction mixture is adjusted with aqueous 1M HCl to weakly acidic. After extraction with dichloromethane the aqueous layer is concentrated under reduced pressure. The residue is used without further purification. LC (method 5): $t_R$=0.61 min; Mass spectrum (ESI$^+$): m/z=189 [M+H]$^+$.

Step 3: N-[dimethyl(oxo)-$\lambda^6$-sulfanylidene]-3,5-difluoro-4-(hydroxymethyl)benzamide 0.80 g (4.25 mmol) 3,5-difluoro-4-(hydroxymethyl)benzoic acid, 0.40 g (4.25 mmol) iminodimethyl-$\lambda^6$-sulfanone (dimethylsulfoximine), 2.96 mL (17.01 mmol) diisopropylethylamine and 1.78 g (4.68 mmol) HATU in 12 mL DMF are stirred at room temperature overnight. The reaction mixture is purified by preparative HPLC. LC (method 5): $t_R$=0.65 min; Mass spectrum (ESI$^+$): m/z=264 [M+H]$^+$.

Step 4: ({[3,5-difluoro-4-(hydroxymethyl)phenyl]methyl}imino)dimethyl-$\lambda^6$-sulfanone 0.65 g (2.47 mmol)N-[dimethyl(oxo)-$\lambda^6$-sulfanylidene]-3,5-difluoro-4-(hydroxymethyl)-benzamide and 0.50 mL borane dimethylsulfide complex in 10 mL tetrahydrofuran are stirred overnight at room temperature. Another 0.50 mL borane dimethylsulfide complex is added. The reaction mixture is stirred for 3 h at 40° C. The solvents are removed under reduced pressure and the residue is purified by silica chromatography. LC (method 5): $t_R$=0.51 min; Mass spectrum (ESI$^+$): m/z=250 [M+H]$^+$.

Step 5: {[(4-{[(2-{[(3R,3aR,6R,6aS)-6-[(tert-butyldimethylsilyl)oxy]-hexahydrofuro[3,2-b]furan-3-yl]oxy}-6-chloro-3-{[2-(trimethylsilyl)ethoxy]methyl}-3H-imidazo[4,5-b]pyridin-5-yl)oxy]methyl}-3,5-difluorophenyl)methyl]imino}dimethyl-$\lambda^6$-sulfanone Under an argon atmosphere 0.13 g (0.52 mmol) ({[3,5-difluoro-4-(hydroxymethyl)phenyl]methyl}imino)dimethyl-$\lambda^6$-sulfanone, 0.34 g (1.05 mmol) cesium carbonate, 19 mg (0.11 mmol) 1,10-phenanthroline and 10 mg (0.05 mmol) copper-(I)-iodide are added to 0.35 g (0.52 mmol) 2-{[(3R,3aR,6R,6aS)-6-[(tert-butyldimethylsilyl)oxy]-hexahydrofuro[3,2-]furan-3-yl]oxy}-6-chloro-5-iodo-3-{[2-(trimethylsilyl)ethoxy]methyl}-3H-imidazo[4,5-b]pyridine in 5 mL dioxane. The reaction mixture is stirred overnight at 100° C. in a sealed tube. The reaction mixture is filtered and evaporated to dryness. The residue is chromatographed on silica gel to give the title compound. LC (method 5): $t_R$=1.28 min; Mass spectrum (ESI$^+$): m/z=790 [M+H]$^+$.

Intermediate 7

4-{[(2-{[(3R,3aR,6R,6aS)-6-[(tert-butyldimethylsilyl)oxy]-hexahydrofuro[3,2-b]furan-3-yl]oxy}-6-chloro-3-{[2-(trimethylsilyl)ethoxy]methyl}-3H-imidazo[4,5-b]pyridin-5-yl)oxy]-methyl}-3,5-difluorobenzoic acid

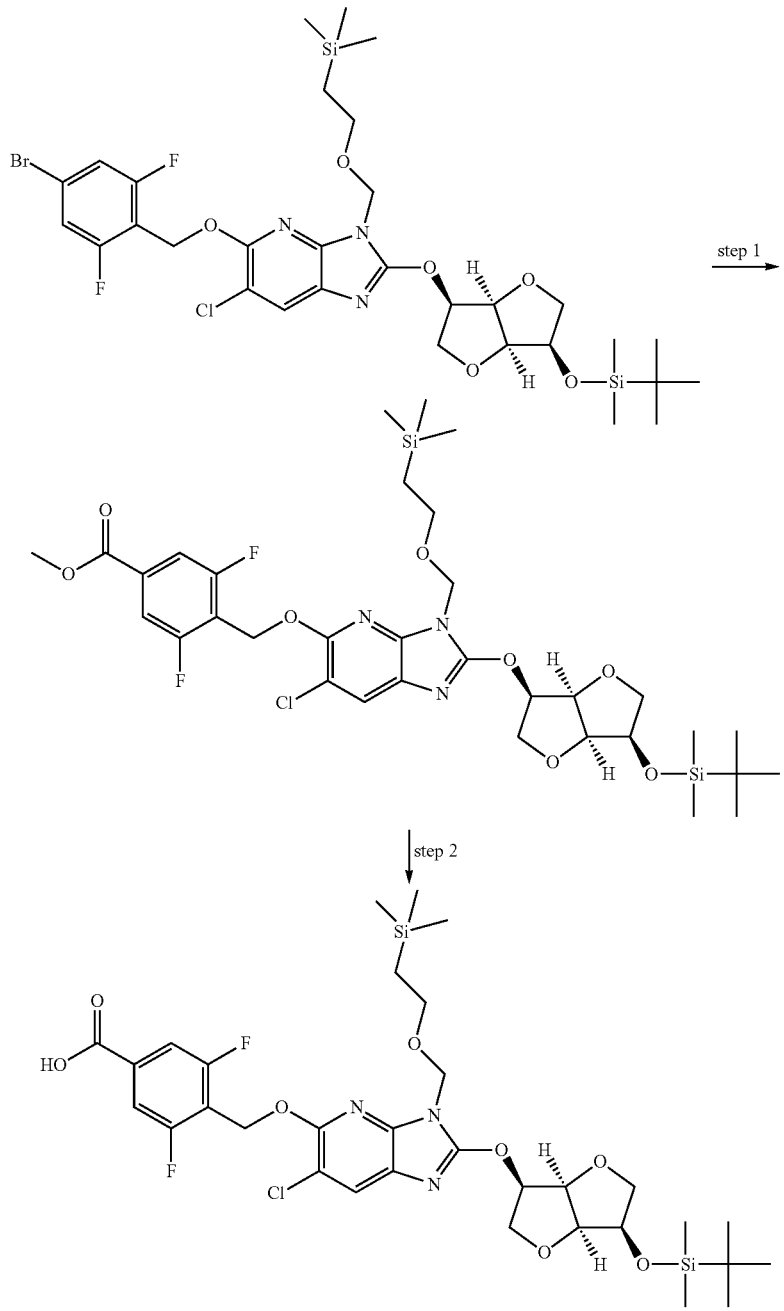

Step 1: methyl 4-{[(2-{[(3R,3aR,6R,6aS)-6-[(tert-butyldimethylsilyl)oxy]-hexahydrofuro[3,2-b]furan-3-yl]oxy}-6-chloro-3-{[2-(trimethylsilyl)ethoxy]methyl}-3H-imidazo[4,5-b]pyridin-5-yl)oxy]methyl}-3,5-difluorobenzoate In a carbonmonoxide atmosphere at 6 bar 1.77 g (2.32 mmol) 2-{[(3R,3aR,6R,6aS)-6-[(tert-butyldimethylsilyl)oxy]-hexahydrofuro[3,2-b]furan-3-yl]oxy}-5-[(4-bromo-2,6-difluorophenyl)methoxy]-6-chloro-3-{[2-(trimethylsilyl)ethoxy]methyl}-3H-imidazo[4,5-b]pyridine, 0.13 g (0.23 mmol) 1,1'-bis-(diphenylphosphino)-ferrocen, 0.05 g (0.23 mmol) palladium-(II)-acetate and 0.65 mL triethylamine in 32 mL methanol are heated at 80° C. for 4 h. The reaction mixture is filtered and evaporated to dryness. The residue is used without further purification. LC (method 6): $t_R$=1.29 min; Mass spectrum (ESI$^+$): m/z=743 [M+H]$^+$.

Step 2: 4-{[(2-{[(3R,3aR,6R,6aS)-6-[(tert-butyldimethylsilyl)oxy]-hexahydrofuro[3,2-b]furan-3-yl]oxy}-6-chloro-3-{[2-(trimethylsilyl)ethoxy]methyl}-3H-imidazo[4,5-b]pyridin-5-yl)oxy]methyl}-3,5-difluorobenzoic acid 1.7 g (2.29 mmol) methyl 4-{[(2-{[(3R,3aR,6R,6aS)-6-[(tert-butyldimethylsilyl)oxy]-hexahydrofuro[3,2-b]furan-3-yl]oxy}-6-chloro-3-{[2-(trimethylsilyl)ethoxy]methyl}-3H-imidazo[4,5-b]pyridin-5-yl)oxy]methyl}-3,5-difluorobenzoate and 0.2 g (8.35 mmol) lithium hydroxide in 20 mL tetrahydrofuran and methanol are stirred at room temperature overnight. The pH of the reaction mixture is adjusted to weakly acidic with aqueous 1M HCl. The precipitate is collected and dried. LC (method 6): $t_R$=1.14 min; Mass spectrum (ESI$^+$): m/z=729 [M+H]$^+$.

Intermediate 8

4-{[(2-{[(3R,3aR,6R,6aS)-6-[(tert-butyldimethylsilyl)oxy]-hexahydrofuro[3,2-b]furan-3-yl]oxy}-6-chloro-3-{[2-(trimethylsilyl)ethoxy]methyl}-3H-imidazo[4,5-b]pyridin-5-yl)oxy]-methyl}-N-[dimethyl(oxo)-λ$^6$-sulfanylidene]-3,5-difluorobenzamide

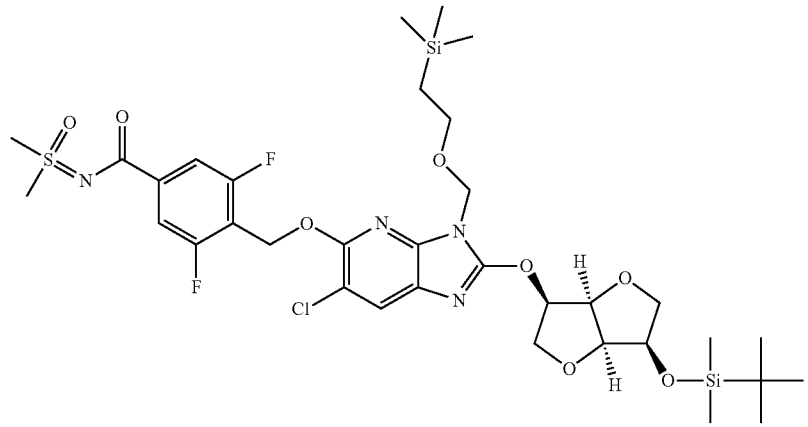 [SMILES: CC(C)(C)[Si](C)(C)O[C@@H]1CO[C@H]2[C@@H]1OC[C@H]2Oc1nc2cc(Cl)c(OCc3c(F)cc(C(=O)N=S(C)(C)=O)cc3F)nc2n1COCC[Si](C)(C)C]

0.70 g (0.96 mmol) 4-{[(2-{[(3R,3aR,6R,6aS)-6-[(tert-butyldimethylsilyl)oxy]-hexahydrofuro[3,2-b]furan-3-yl]oxy}-6-chloro-3-{[2-(trimethylsilyl)ethoxy]methyl}-3H-imidazo[4,5-b]pyridin-5-yl)oxy]methyl}-3,5-difluorobenzoic acid, 0.09 g (0.96 mmol) iminodimethyl-λ$^6$-sulfanone, 0.40 g (1.06 mmol) HATU and 0.67 mL (3.84 mmol) DIPEA in 10 mL DMF are stirred at room temperature overnight. Water and dichloromethane are added to the reaction mixture. The organic layer is separated and dried. The solvent is removed under reduced pressure. LC (method 5): $t_R$=1.34 min; Mass spectrum (ESI$^+$): m/z=803 [M+H]$^+$.

General Procedure 1 (P1) for Intermediates Shown in Table 1:

0.10 g (0.14 mmol) 4-{[(2-{[(3R,3aR,6R,6aS)-6-[(tert-butyldimethylsilyl)oxy]-hexahydrofuro[3,2-b]furan-3-yl]oxy}-6-chloro-3-{[2-(trimethylsilyl)ethoxy]methyl}-3H-imidazo[4,5-b]pyridin-5-yl)oxy]methyl}-3,5-difluorobenzoic acid, 0.14 mmol of the corresponding sulfoximines or sulfodiimines, 0.06 g (1.51 mmol) HATU and 0.10 mL (0.55 mmol) DIPEA in 2 mL DMF are stirred at room temperature for 2 h. Water and dichloromethane is added. The organic layer is separated, dried and evaporated to dryness. The residue is used without further purification.

The following intermediates in table 1 (intermediate number given in column #) are prepared according to P1.

TABLE 1

| # | structure | name | ESI-MS m/z [M + H$^+$] | HPLC R$_t$ [min], [Method] |
|---|---|---|---|---|
| 9 | 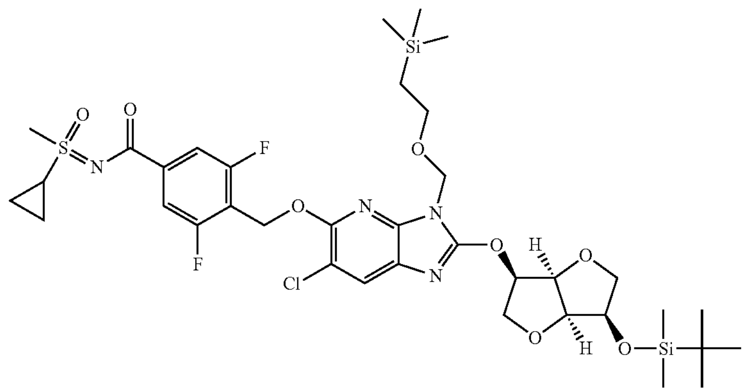 [SMILES: CC(C)(C)[Si](C)(C)O[C@@H]1CO[C@H]2[C@@H]1OC[C@H]2Oc1nc2cc(Cl)c(OCc3c(F)cc(C(=O)N=S(C)(=O)C4CC4)cc3F)nc2n1COCC[Si](C)(C)C] | 4-{[(2-{[(3R,3aR,6R,6aS)-6-[(tert-butyl-dimethylsilyl)-oxy]-hexahydrofuro[3,2-b]furan-3-yl]oxy}-6-chloro-3-{[2-(trimethylsilyl)-ethoxy]methyl}-3H-imidazo[4,5-b]pyridin-5-yl)oxy]methyl}-N-[cyclopropyl(methyl)oxo-λ$^6$-sulfanylidene]-3,5-difluorobenzamide | no peak | 1.36, [5] |

TABLE 1-continued

| # | structure | name | ESI-MS m/z [M + H+] | HPLC R_t [min], [Method] |
|---|---|---|---|---|
| 10 | 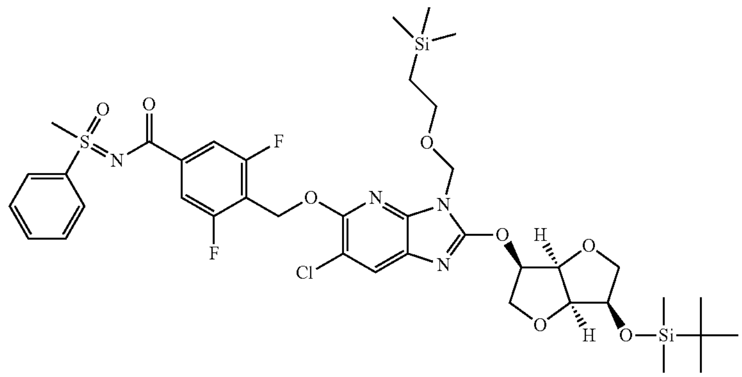 [SMILES: CC(C)(C)[Si](C)(C)O[C@@H]1CO[C@H]2[C@@H]1OC[C@H]2Oc1nc2cc(Cl)c(OCc3c(F)cc(C(=O)N=S(C)(=O)c4ccccc4)cc3F)nc2n1COCC[Si](C)(C)C] | 4-{[(2-{[(3R,3aR,6R,6aS)-6-[(tert-butyl-dimethylsilyl)oxy]-hexahydrofuro[3,2-b]furan-3-yl]oxy}-6-chloro-3-{[2-(trimethylsilyl)ethoxy]methyl}-3H-imidazo[4,5-b]pyridin-5-yl)oxy]methyl}-3,5-difluoro-N-[methyl(oxo)phenyl-λ⁶-sulfanylidene]benzamide | no peak | 1.37, [5] |
| 11 | 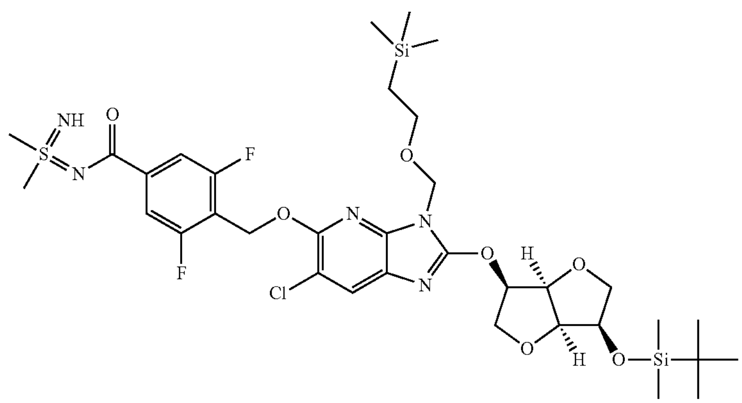 [SMILES: CC(C)(C)[Si](C)(C)O[C@@H]1CO[C@H]2[C@@H]1OC[C@H]2Oc1nc2cc(Cl)c(OCc3c(F)cc(C(=O)N=S(C)(C)=N)cc3F)nc2n1COCC[Si](C)(C)C] | 4-{[(2-{[(3R,3aR,6R,6aS)-6-[(tert-butyl-dimethylsilyl)oxy]-hexahydrofuro[3,2-b]furan-3-yl]oxy}-6-chloro-3-{[3-(trimethylsilyl)ethoxy]methyl}-3H-imidazo[4,5-b]pyridin-5-yl)oxy]methyl}-3,5-difluoro-N-(iminodimethyl-λ⁶-sulfanylidene)benzamide | no peak | 1.32, [5] |

Intermediate 12

4-{[(2-{[(3R,3aR,6R,6aR)-6-hydroxy-hexahydrofuro[3,2-b]furan-3-yl]oxy}-6-chloro-3H-imidazo[4,5-b]pyridin-5-yl)oxy]methyl}-3,5-difluorobenzoic acid

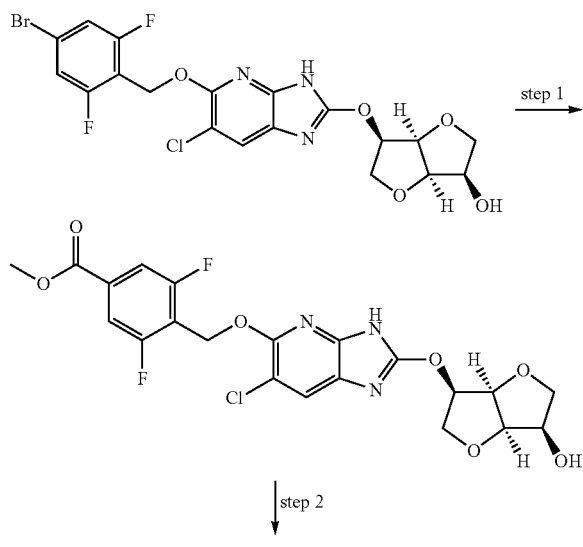

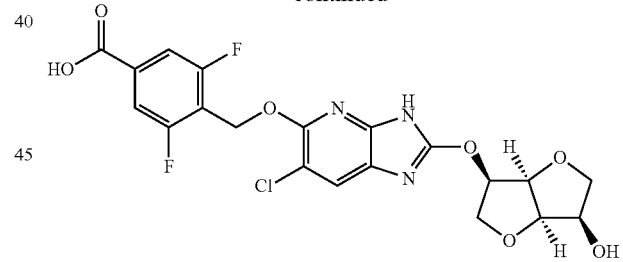

Step 1: methyl 4-{[(2-{[(3R,3aR,6R,6aR)-6-hydroxy-hexahydrofuro[3,2-b]furan-3-yl]oxy}-6-chloro-3H-imidazo[4,5-b]pyridin-5-yl)oxy]methyl}-3,5-difluorobenzoate In a carbon monoxide atmosphere at 6 bar 0.1 g (0.19 mmol) (3R,3aR,6R,6aR)-6-({5-[(4-bromo-2,6-difluorophenyl)methoxy]-6-chloro-3H-imidazo[4,5-b]pyridin-2-yl}oxy)-hexahydrofuro[3,2-b]furan-3-ol, 0.01 g (0.02 mmol) 1,1'-bis-(diphenylphosphino)-ferrocene, 0.005 g (0.02 mmol) palladium-(II)-acetate and 0.05 mL (0.39 mmol) triethylamine in 3 mL methanol are heated at 80° C. for 4h. The reaction mixture is filtered and evaporated to dryness. The residue is used without further purification. LC (method 5): $t_R$=0.96 min; Mass spectrum (ESI⁺): m/z=498 [M+H]⁺.

Step 2: 4-{[(2-{[(3R,3aR,6R,6aR)-6-hydroxy-hexahydrofuro[3,2-b]furan-3-yl]oxy}-6-chloro-3H-imidazo[4,5-b]pyridin-5-yl)oxy]methyl}-3,5-difluorobenzoic acid 0.1 g (0.19 mmol) methyl 4-{[(2-{[(3R,3aR,6R,6aR)-6-hydroxy-hexahydrofuro[3,2-b]furan-3-yl]oxy}-6-chloro-3H-imidazo[4,5-b]pyridin-5-yl)oxy]methyl}-3,5-difluorobenzoate and 0.02 g (0.77 mmol) lithium hydroxide in 2 mL tetrahydrofuran and 1 mL methanol are stirred at room temperature overnight. The pH of the reaction mixture is adjusted to weakly acidic with aqueous 1M HCl. Dichloromethane is added and the layers are separated. The organic layer is dried and evaporated to dryness. The residue is purified by silica chromatography. LC (method 5): $t_R$=0.85 min; Mass spectrum (ESI$^+$): m/z=484 [M+H]$^+$.

Intermediate 13

(2E)-3-(4-{[(2-{[(3R,3aR,6R,6aR)-6-hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)oxy]methyl}-3,5-difluorophenyl)prop-2-enoic acid

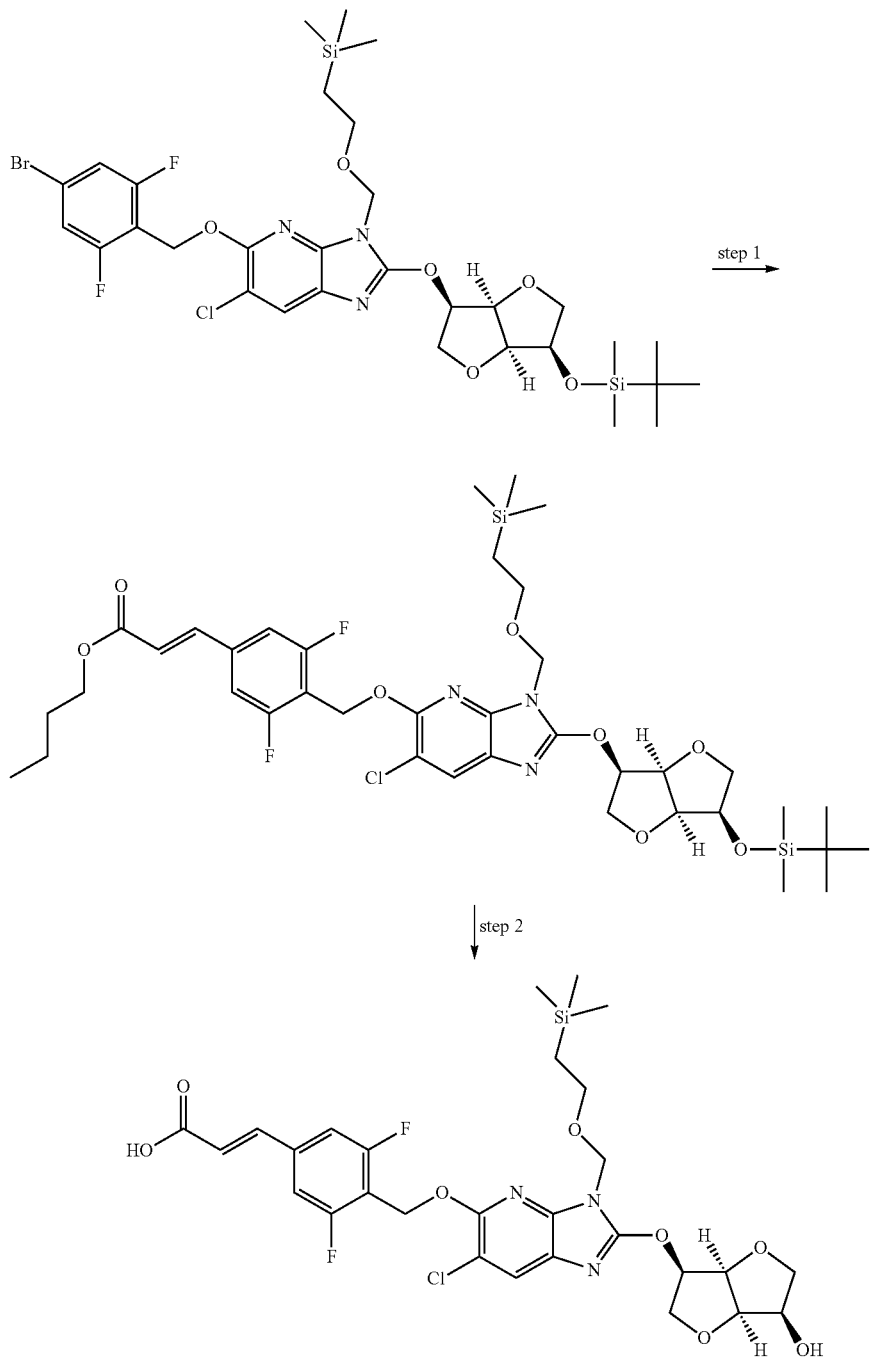

Step 1: butyl (2E)-3-(4-{[(2-{[(3R,3aR,6R,6aS)-6-[(tert-butyldimethylsilyl)oxy]-hexahydrofuro[3,2-b]furan-3-yl]oxy}-6-chloro-3-{[2-(trimethylsilyl)ethoxy]methyl}-3H-imidazo-[4,5-b]pyridin-5-yl)oxy]methyl}-3,5-difluorophenyl)prop-2-enoate Under an argon atmosphere 0.50 g (0.66 mmol) 2-{[(3R,3aR,6R,6aS)-6-[(tert-butyl-dimethylsilyl)oxy]-hexahydrofuro[3,2-b]furan-3-yl]oxy}-5-[(4-bromo-2,6-difluoro-phenyl)methoxy]-6-chloro-3-{[2-(trimethylsilyl)ethoxy]methyl}-3H-imidazo[4,5-b]-pyridine, 0.13 g (0.98 mmol) butyl prop-2-enoate, 3.7 mg 1,4-diazabicyclo-(2.2.2) octane (DABCO), 3.0 mg palladium-(II)-acetate and 90.5 mg (0.65 mmol) potassium carbonate in 5 mL DMF are stirred for 1.5 h at 150° C. After cooling to room temperature water is added and the reaction mixture is extracted with dichloromethane. The combined organic layers are dried and evaporated to dryness. The residue is purified by silica-chromatography. LC (method 3): $t_R$=0.56 min; Mass spectrum (ESI$^+$): m/z=810.5 [M+H]$^+$.

Step 2: (2E)-3-(4-{[(2-{[(3R,3aR,6R,6aR)-6-hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)oxy]methyl}-3,5-difluorophenyl)prop-2-enoic acid 70 mg (0.086 mmol) butyl (2E)-3-(4-{[(2-{[(3R,3aR,6R,6aS)-6-[(tert-butyl-dimethyl-silyl)oxy]-hexahydrofuro[3,2-b]furan-3-yl]oxy}-6-chloro-3-{[2-(trimethyl-silyl)-ethoxy]-methyl}-3H-imidazo[4,5-b]pyridin-5-yl)oxy]methyl}-3,5-difluorophenyl)-prop-2-enoate and 31.0 mg (1.30 mmol) lithium hydroxide in 4 mL tetrahydrofuran, 4 mL methanol and 4 mL water are stirred overnight at room temperature. Afterwards the pH of the reaction mixture is adjusted to weakly acidic with aqueous 4 N HCl. The aqueous layer is extracted several times with dichloromethane. The combined organic layers are dried and evaporated to dryness. The residue is used without further purification. LC (method 3): $t_R$=0.71 min; Mass spectrum (ESI$^+$): m/z=640.3 [M+H]$^+$.

Intermediate 14

(2E)-3-(4-{[(2-{[(3R,3aR,6R,6aR)-6-hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)oxy]methyl}-3,5-difluorophenyl)-N-[dimethyl(oxo)-λ$^6$-sulfanylidene]prop-2-enamide

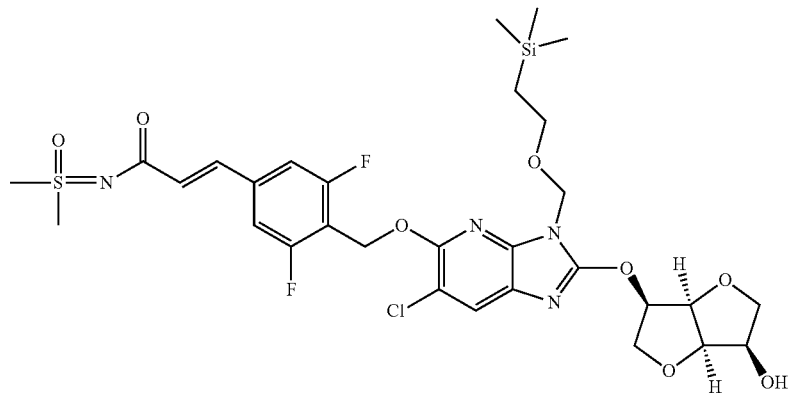 [SMILES: C[Si](C)(C)CCOCn1c(O[C@@H]2CO[C@H]3[C@@H]2OC[C@H]3O)nc2cc(Cl)c(OCc3c(F)cc(/C=C/C(=O)N=S(C)(C)=O)cc3F)nc21]

43 mg (0.067 mmol) (2E)-3-(4-{[(2-{[(3R,3aR,6R,6aR)-6-hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)oxy]methyl}-3,5-difluorophenyl)prop-2-enoic acid, 28 mg (0.074 mmol) HATU and 29 µL (0.168 mmol) DIPEA in 2 mL DMF are stirred for 30 min at room temperature. 8 mg (0.081 mmol) iminodimethyl-λ$^6$-sulfanone (dimethylsulfoximine) is added and the reaction mixture is stirred at room temperature overnight. Water and dichloromethane are added. The organic layer is dried and evaporated to dryness. The residue is purified with preparative HPLC. LC (method 3): $t_R$=0.69 min; Mass spectrum (ESI$^+$): m/z=715.3 [M+H.

Intermediate 15

3-(4-{[(2-{[(3R,3aR,6R,6aR)-6-hydroxy-hexahydro-furo[3,2-b]furan-3-yl]oxy}-6-chloro-3-{[2-(trimethylsilyl)ethoxy]methyl}-3H-imidazo[4,5-b]pyridin-5-yl)oxy]methyl}-3,5-difluorophenyl)propanoic acid

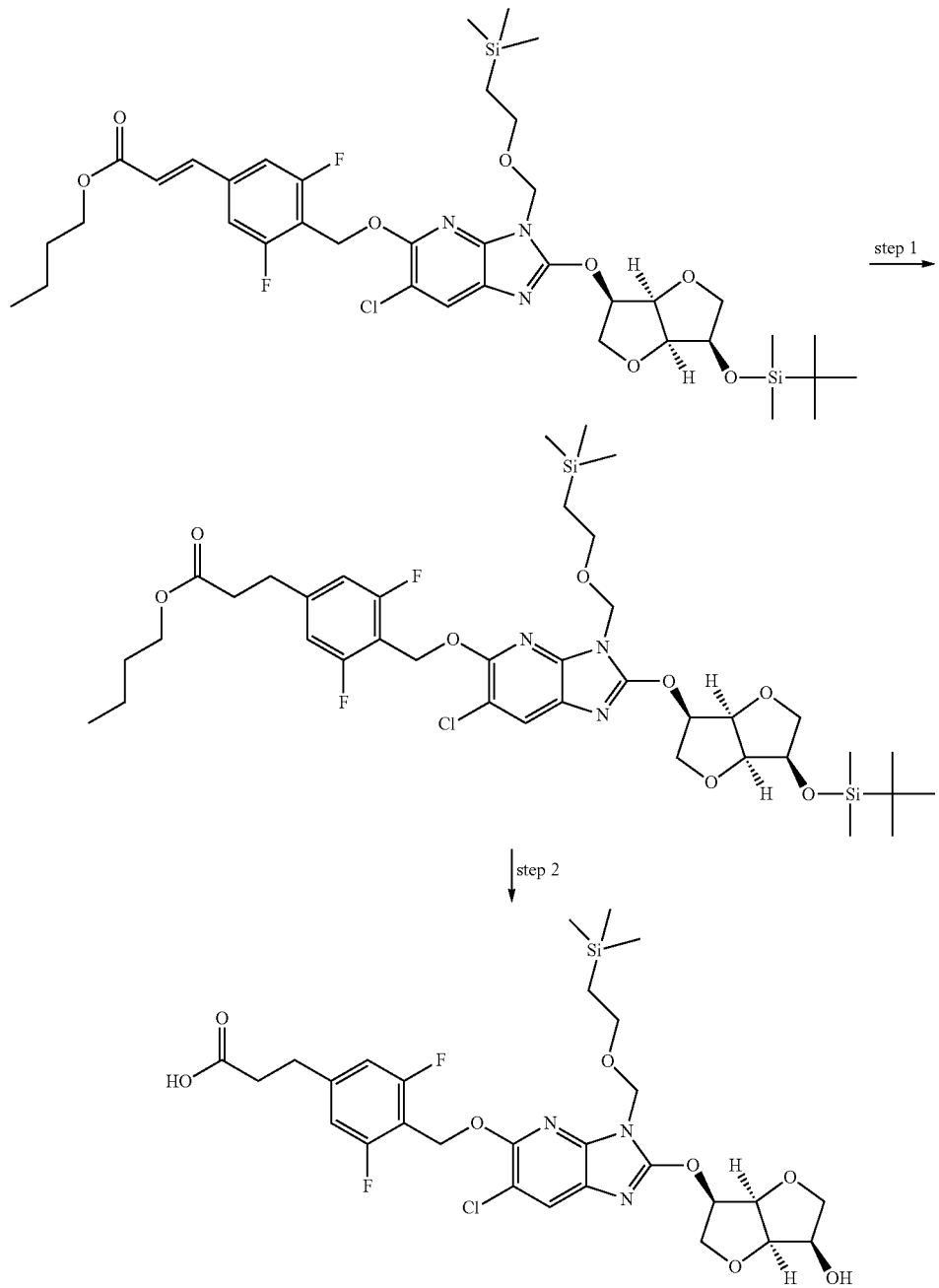

Step 1: butyl 3-(4-{[(2-{[(3R,3aR,6R,6aS)-6-[(tert-butyldimethylsilyl)oxy]-hexahydrofuro[3,2-b]furan-3-yl]oxy}-6-chloro-3-{[2-(trimethylsilyl)ethoxy]methyl}-3H-imidazo[4,5-]pyridin-5-yl)oxy]methyl}-3,5-difluorophenyl)propanoate Under a 3 bar hydrogen atmosphere 0.30 g (0.37 mmol) butyl (2E)-3-(4-{[(2-{[(3R,3aR,6R,6aS)-6-[(tert-butyldimethylsilyl)oxy]-hexahydrofuro[3,2-b]furan-3-yl]-oxy}-6-chloro-3-{[2-(trimethylsilyl)ethoxy]methyl}-3H-imidazo[4,5-b]pyridin-5-yl)oxy]-methyl}-3,5-difluorophenyl)prop-2-enoate and 0.05 g palladium on carbon (10%) in 50 mL methanol are stirred at room temperature. The reaction mixture is filtered and evaporated to dryness. The residue is used without further purification. LC (method 3): $t_R$=0.55 min; Mass spectrum (ESI$^+$): m/z=812.8 [M+H]$^+$.

Step 2: 3-(4-{[(2-{[(3R,3aR,6R,6aR)-6-hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)oxy]methyl}-3,5-difluorophenyl)propanoic acid 0.29 g (0.35 mmol) butyl 3-(4-{[(2-{[(3R,3aR,6R,6aS)-6-[(tert-butyldimethylsilyl)oxy]-hexahydrofuro[3,2-b]furan-3-yl]oxy}-6-chloro-3-{[2-(trimethylsilyl-)ethoxy]methyl}-3H-imidazo[4,5-]pyridin-5-yl)oxy]methyl}-3,5-difluoro-phenyl)propanoate and 0.13 mg (5.32 mmol) lithium hydroxide in 20 mL tetrahydrofuran (THF), 20 mL methanol (MeOH) and 20 mL water are stirred at RT overnight. Afterwards water is added and the reaction mixture is extracted with dichloromethane. The organic layer is separated, dried and evaporated to dryness. The residue is used without further purification. LC (method 3): $t_R$=0.7 min; Mass spectrum (ESI$^+$): m/z=642.3 [M+H]$^+$.

Intermediate 16

3-(4-{[(2-{[(3R,3aR,6R,6aR)-6-hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)oxy]methyl}-3,5-difluorophenyl)-N-[dimethyl(oxo)-$\lambda^6$-sulfanylidene]propanamide din-5-yl)oxy]methyl}-3,5-difluorophenyl)propanoic acid, 182 mg (0.48 mmol) HATU and 190 µL (1.10 mmol) DIPEA in 14 mL DMF are stirred for 30 min at room temperature. 49 mg (0.52 mmol) iminodimethyl-$\lambda^6$-sulfanone (dimethylsulfoximine) is added and the reaction mixture is stirred at room temperature overnight. Water and dichloromethane are added. The organic layer is separated, dried and evaporated to dryness. The residue is purified with preparative HPLC. LC (method 3): $t_R$=0.69 min; Mass spectrum (ESI$^+$): m/z=717.3 [M+H].

Intermediate 17

{[3-(4-{[(2-{[(3R,3aR,6R,6aR)-6-hydroxy-hexahydrofuro[3,2-b]furan-3-yl]oxy}-6-chloro-3-{[2-(trimethylsilyl)ethoxy]methyl}-3H-imidazo[4,5-b]pyridin-5-yl)oxy]methyl}-3,5-difluorophenyl)propyl]imino}dimethyl-$\lambda^6$-sulfanone

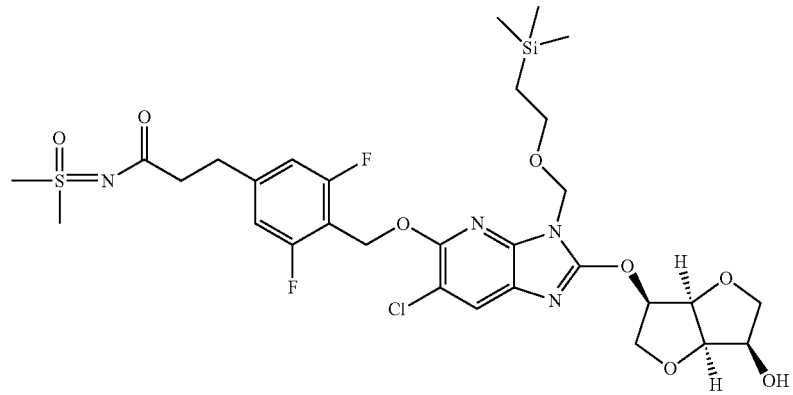 [SMILES: C[Si](C)(C)CCOCn1c(O[C@@H]2CO[C@H]3[C@@H]2OC[C@H]3O)nc2cc(Cl)c(OCc3c(F)cc(CCC(=O)N=S(C)(C)=O)cc3F)nc21]

280 mg (0.44 mmol) 3-(4-{[(2-{[(3R,3aR,6R,6aR)-6-hydroxy-hexahydrofuro[3,2-b]furan-3-yl]oxy}-6-chloro-3-{[2-(trimethylsilyl)ethoxy]methyl}-3H-imidazo[4,5-b]pyri-

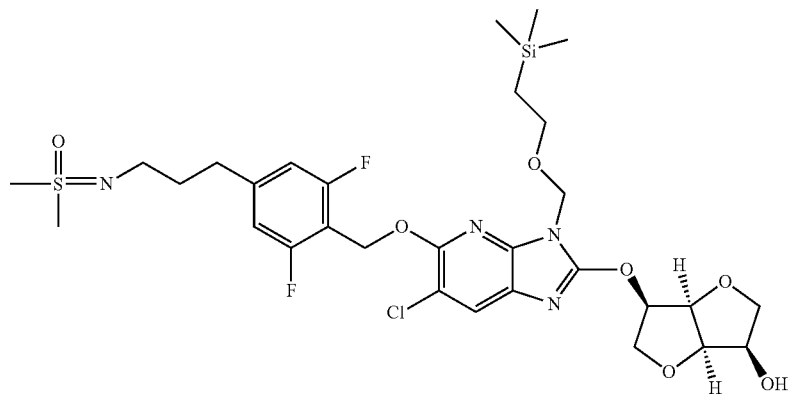 [SMILES: C[Si](C)(C)CCOCn1c(O[C@@H]2CO[C@H]3[C@@H]2OC[C@H]3O)nc2cc(Cl)c(OCc3c(F)cc(CCCN=S(C)(C)=O)cc3F)nc21]

At 0° C. 10 equivalents BH$_3$*Me$_2$S are added to 80 mg (0.11 mmol) 3-(4-{[(2-{[(3R,3aR,6R,6aR)-6-hydroxy-hexahydrofuro[3,2-b]furan-3-yl]oxy}-6-chloro-3-{[2-(tri-methylsilyl)ethoxy]methyl}-3H-imidazo[4,5-b]pyridin-5-yl)oxy]methyl}-3,5-difluorophenyl)-N-[dimethyl(oxo)-λ$^6$-sulfanylidene]propanamide in 2 mL tetrahydrofuran and stirred for 2 h. Additional 10 equivalents BH$_3$*Me$_2$S are added and the reaction mixture is stirred for 3 h at 0° C. Additional 10 equivalents BH$_3$*Me$_2$S are added and the reaction mixture is stirred for 45 min at 8° C. At 0° C. 10 mL of an aqueous 1N HCl solution is added dropwise and the reaction mixture is stirred for 30 min at RT. The aqueous layer is extracted several times with dichloromethane. The combined organic layers are dried, evaporated to dryness and purified by preparative HPLC. LC (method 3): $t_R$=0.62 min; Mass spectrum (ESI$^+$): m/z=703 [M+H].

Intermediate 18

Cyclopentyl(imino)methyl-λ$^6$-sulfanone

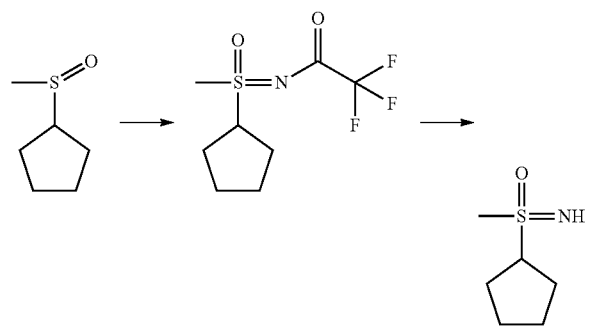

Sulfoximines are synthesized according to literature procedures (*Org. Lett.*, 2004, 6 (8), 1305-1307 or WO2008/141843).

Step 1: Methanesulfinylcyclopentane

At 0° C. 294 g (1.38 mol) sodium metaperiodate is added stepwise to 120 g (1.03 mol) methanesulfinylcyclopentane in 2 L methanol and 2 L water and stirred for 30 min. After additional stirring for 16 h at room temperature the solid is removed and washed with methanol. The filtrate is concentrated under reduced pressure. Sodium chloride is added and diluted with dichlormethane. The suspension is filtered, washed with dichlormethane, dried and concentrated to dryness. The compound is used without further purification.

Step 2: N-[cyclopentyl(methyl)oxo-λ$^6$-sulfanylidene]-2,2,2-trifluoroacetamide

Under an argon atmosphere 13 g (0.03 mol) rhodium-(II) acetate (dimer) is added to 90 g (0.68 mol) methanesulfinylcyclopentane, 154 g (1.36 mol) 2,2,2-trifluoroacetamide, 109 g (2.71 mol) magnesium oxide and 329 g (1.02 mol) iodosobenzene diacetate in 1 L dichlormethane and stirred for 24 h at room temperature. The reaction mixture is filtered through Celite and washed with dichlormethane. The filtrated is reduced to dryness and the residue is purified by silica chromatography.

Step 3: Cyclopentyl(imino)methyl-λ$^6$-sulfanone 19.8 g (0.14 mol) potassium carbonate is added to 35 g (0.14 mol) N-[cyclopentyl(methyl)oxo-λ$^6$-sulfanylidene]-2,2,2-trifluoroacetamide in 500 mL methanol and stirred for 2 h at room temperature. The reaction mixture is filtered through Celite and washed with methanol. The filtrate is concentrated to dryness and the residue is purified by silica chromatography. LC (method 5): $t_R$=0.18 min; Mass spectrum (ESI$^+$): m/z=148 [M+H].

Intermediate 19

Imino(methyl)pyridin-3-yl-λ$^6$-sulfanone

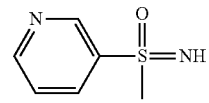

5.0 mL sulfuric acid is added to a cooled solution of 1.00 g (7.08 mmol) 3-methanesulfinylpyridine and 0.92 g (14.15 mmol) in 20 mL dichloromethane. The reaction mixture is stirred at 45° C. for 24 h. After addition of ice water, the layers are separated and the aqueous layer is adjusted to pH 9 with sodium hydroxide solution (35%). Water is removed and the residue is stirred with ethanol at 55° C. for 30 min. After filtration the filtrate is concentrated to dryness and the residue is stirred in dichloromethane. After filtration the solvent is removed and the residue purified by silica chromatography. LC (method 5): $t_R$=0.12 min; Mass spectrum (ESI$^+$): m/z=157 [M+H].

Intermediate 20

(Dicyclopropylimino-λ$^6$-sulfanyl)one

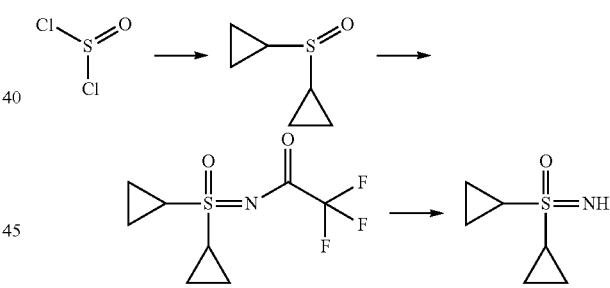

Step 1: (Cyclopropanesulfinyl)cyclopropane 0.41 mol thionyl chloride is added to a stirred solution of 0.21 mmol cyclopropylmagnesium bromide at 0° C. The reaction mixture is stirred for 1 h, diluted with ethyl acetate and washed with water. After extracting with 10% methanol in DCM the combined organic layers are dried and concentrated under reduced pressure. The residue is used without further purification.

Step 2: (N-[dicyclopropyl(oxo)-λ$^6$-sulfanylidene]-2,2,2-trifluoroacetamide

Under an argon atmosphere 1.53 g (3.46 mmol) rhodium-(II) acetate (dimer) is added to 18.0 g (0.14 mol) cyclopropanesulfinyl)cyclopropane, 31.2 g (0.28 mol) 2,2,2-trifluoroacetamide, 22.3 g (0.55 mol) magnesium oxide and 66.8 g (0.21 mol) iodosobenzene diacetate in 0.4 L dichlormethane and stirred for 15 h at room temperature. The reaction mixture is filtered through Celite and washed with dichlormethane. The filtrated is concentrated to dryness and the residue is purified by silica chromatography.

Step 3: (Dicyclopropylimino-λ⁶-sulfanyl)one 12.5 g (0.09 mol) potassium carbonate is added to 11.0 g (0.05 mol)N-[dicyclopropyl(oxo)-λ⁶-sulfanylidene]-2,2,2-trifluoroacetamide in 110 mL methanol and stirred for 2 h at room temperature. The reaction mixture is filtered through Celite and washed with methanol. The filtrate is concentrated to dryness and the residue is purified by silica chromatography. LC (method 5): $t_R$=0.20 min; Mass spectrum (ESI⁺): m/z=146 [M+H].

Example 1

[(4-{[(2-{[(3R,3aR,6R,6aR)-6-hydroxy-hexahydrofuro[3,2-b]furan-3-yl]oxy}-6-chloro-3H-imidazo[4,5-b]pyridin-5-yl)oxy]methyl}-3,5-difluorophenyl)imino]dimethyl-λ⁶-sulfanone

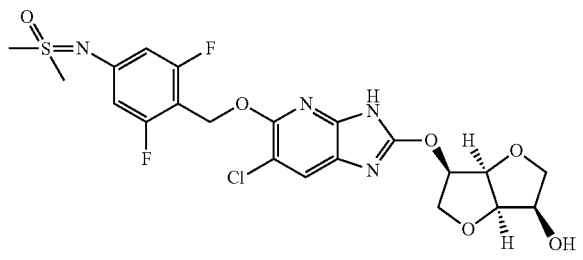 [SMILES: CS(C)(=O)=Nc1cc(F)c(COc2nc3[nH]c(O[C@@H]4CO[C@H]5[C@@H]4OC[C@H]5O)nc3cc2Cl)c(F)c1]

Under an argon atmosphere 5.4 mg (0.006 mmol) tris(dibenzylidene-acetone)-dipalladium (0) catalyst is added to degassed 40.0 mg (0.08 mmol) (3R,3aR,6R,6aR)-6-({5-[(4-bromo-2-fluorophenyl)methoxy]-6-chloro-1H-imidazo[4,5-b]pyridin-2-yl}oxy)-hexahydrofuro[3,2-b]furan-3-ol, 10.8 mg (0.12 mmol) iminodimethyl-λ⁶-sulfanone (dimethylsulfoximine), 4.6 mg (0.02 mmol) 2-(di-tert-butylphosphino)-biphenyl, 18.5 mg (0.19 mmol) sodium tert.-butoxide in 2 mL dioxane. The reaction mixture is stirred 3 h at 80° C. The precipitate is collected, dissolved in DMF and purified by preparative HPLC. The product containing fractions are combined and evaporated to dryness. LC (method 5): $t_R$=0.84 min; Mass spectrum (ESI⁺): m/z=531 [M+H]⁺.

General Procedure 2 (P2) for Examples Shown in Table 2:

Under an argon atmosphere 5.37 mg (0.006 mmol) tris(dibenzylidene-acetone)-dipalladium (0) catalyst are added to degassed 40.0 mg (0.08 mmol) (3R,3aR,6R,6aR)-6-({5-[(4-bromo-2-fluorophenyl)methoxy]-6-chloro-1H-imidazo[4,5-b]pyridin-2-yl}oxy)-hexahydrofuro[3,2-b]furan-3-ol, 0.12 mmol sulfoximine or sulfodiimine, 4.6 mg (0.02 mmol) 2-(di-tert-butylphosphino)-biphenyl, 18.5 mg (0.19 mmol) sodium tert.-butoxide in 2 mL dioxane. The reaction mixture is stirred 3 h at 80° C. The precipitate is collected, dissolved in DMF and purified by preparative HPLC. The product containing fractions are combined and evaporated to dryness. The following examples in table 2 (example number given in column #) are prepared according to P2.

TABLE 2

| # | structure | name | ESI-MS m/z [M + H⁺] | HPLC $R_t$ [min], [Method] |
|---|---|---|---|---|
| 2 | 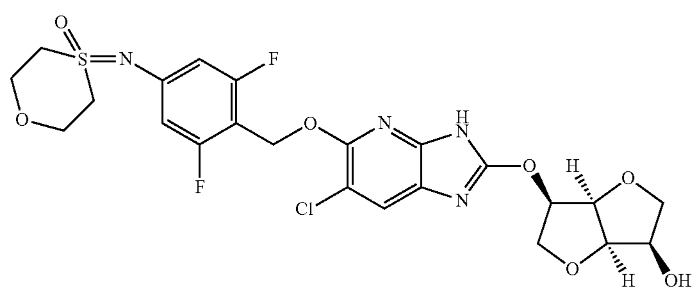 [SMILES: O=S1(=Nc2cc(F)c(COc3nc4[nH]c(O[C@@H]5CO[C@H]6[C@@H]5OC[C@H]6O)nc4cc3Cl)c(F)c2)CCOCC1] | 4-[(4-{[(2-{[(3R,3aR,6R,6aR)-6-hydroxy-hexahydrofuro[3,2-b]furan-3-yl]oxy}-6-chloro-3H-imidazo[4,5-b]pyridin-5-yl)oxy]methyl}-3,5-difluorophenyl)imino]-1,4λ⁶-oxathian-4-one | 573 | 0.88, [5] |
| 3 | 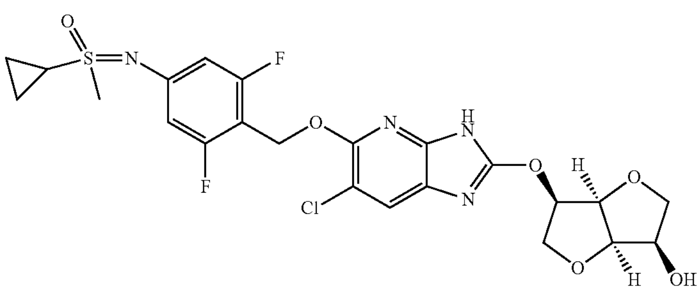 [SMILES: CS(=O)(=Nc1cc(F)c(COc2nc3[nH]c(O[C@@H]4CO[C@H]5[C@@H]4OC[C@H]5O)nc3cc2Cl)c(F)c1)C1CC1] | (3R,3aR,6R,6aR)-6-({6-chloro-5-[(4-{[cyclopropyl(methyl)oxo-λ⁶-sulfanylidene)amino}-2,6-difluorophenyl)methoxy]-3H-imidazo[4,5-b]pyridin-2-yl}oxy)-hexahydrofuran[3,2-b]furan-3-ol | 557 | 0.90, [5] |

TABLE 2-continued

| # | structure | name | ESI-MS m/z [M + H+] | HPLC R$_t$ [min], [Method] |
|---|---|---|---|---|
| 4 | 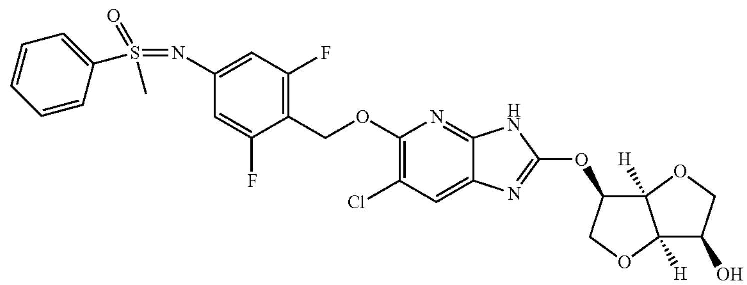 [SMILES: CS(=O)(=Nc1cc(F)c(COc2nc3[nH]c(O[C@@H]4CO[C@H]5[C@@H]4OC[C@H]5O)nc3cc2Cl)c(F)c1)c1ccccc1] | (3R,3aR,6R,6aR)-6-({6-chloro-5-[(2,6-difluoro-4-{[methyl(oxo)phenyl-λ⁶-sulfanylidene]amino}phenyl)-methoxy]-3H-imidazo[4,5-b]pyridin-2-yl}oxy)-hexahydrofuro[3,2-b]furan-3-ol | 593 | 0.95, [5] |

Example 5

(4-{[(2-{[(3R,3aR,6R,6aR)-6-hydroxy-hexahydrofuro[3,2-b]furan-3-yl]oxy}-6-chloro-3H-imidazo[4,5-b]pyridin-5-yl)oxy]methyl}-3,5-difluorophenyl)(imino)methyl-λ⁶-sulfanone

Example 6

(3R,3aR,6R,6aR)-6-({6-chloro-5-[(4-{[(cyanoimino)dimethyl-λ⁶-sulfanylidene]amino}-2,6-difluorophenyl)methoxy]-3H-imidazo[4,5-b]pyridin-2-yl}oxy)-hexahydrofuro[3,2-b]furan-3-ol

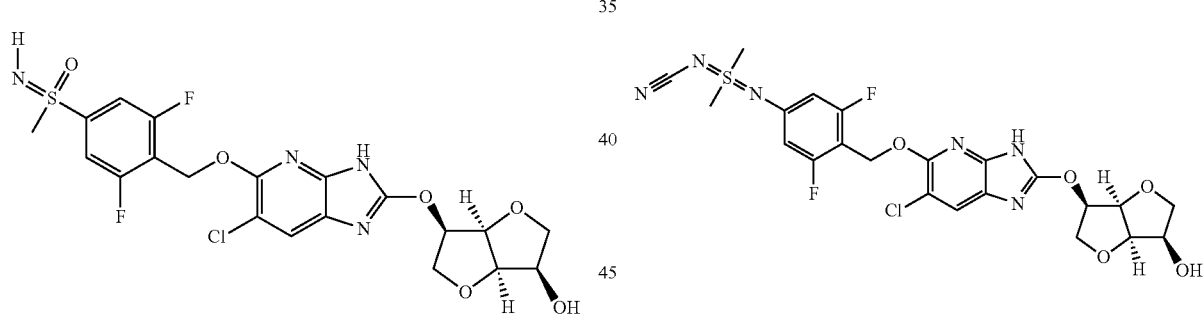

0.27 g (0.30 mmol) 2-(trimethylsilyl)ethyl N-[(4-{[(2-{[(3R,3aR,6R,6aS)-6-[(tert-butyldimethylsilyl)oxy]-hexahydrofuro[3,2-b]furan-3-yl]oxy}-6-chloro-1-{[2-(trimethylsilyl)-ethoxy]methyl}-1H-imidazo[4,5-b]pyridin-5-yl)oxy]methyl}-3,5-difluoro-phenyl)-(methyl)oxo-λ⁶-sulfanylidene]carbamate in 2 mL dichloromethane (DCM) and 2 mL trifluoroacetic acid (TFA) are stirred at room temperature for 3 h. The reaction mixture is evaporated to dryness and the residue is purified by silica chromatography. The product containing fractions are combined and evaporated to dryness. The residue is washed with diisopropylether and dried. LC (method 5): t$_R$=0.75 min; Mass spectrum (ESI⁺): m/z=517 [M+H]⁺.

Under an argon atmosphere 8.1 mg (0.01 mmol) tris(dibenzylidene-acetone)-dipalladium (0) catalyst is added to degassed 60.0 mg (0.12 mmol) (3R,3aR,6R,6aR)-6-({5-[(4-bromo-2,6-difluorophenyl)methoxy]-6-chloro-3H-imidazo[4,5-b]pyridin-2-yl}-oxy)-hexahydrofuro[3,2-b]furan-3-ol, 20.3 mg (0.17 mmol) cyano(iminodimethyl-λ⁶-sulfanylidene)amine, 6.9 (0.02 mmol) 2-(di-tert-butylphosphino)-biphenyl, 27.8 mg (0.29 mmol) sodium tert.-butoxide in 2 mL dioxane. The reaction mixture is stirred 3 h at 80° C. The precipitate is collected, dissolved in DMF and purified by preparative HPLC. The product containing fractions are combined and evaporated to dryness. LC (method 5): t$_R$=0.83 min; Mass spectrum (ESI⁺): m/z=555 [M+H]⁺.

Example 7

4-{[(2-{[(3R,3aR,6R,6aR)-6-hydroxy-hexahydrofuro[3,2-b]furan-3-yl]oxy}-6-chloro-3H-imidazo[4,5-b]pyridin-5-yl)oxy]methyl}-N-[dimethyl(oxo)-λ⁶-sulfanylidene]-3,5-difluorobenzamide

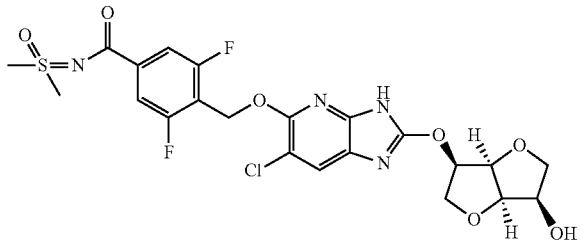 [SMILES: CS(C)(=O)=NC(=O)c1cc(F)c(COc2nc3[nH]c(O[C@@H]4CO[C@H]5[C@@H]4OC[C@H]5O)nc3cc2Cl)c(F)c1]

35 mg (0.04 mmol) 4-{[(2-{[(3R,3aR,6R,6aS)-6-[(tert-butyldimethylsilyl)oxy]-hexahydrofuro[3,2-b]furan-3-yl]oxy}-6-chloro-3-{[2-(trimethylsilyl)ethoxy]methyl}-3H-imidazo[4,5-b]pyridin-5-yl)oxy]methyl}-N-[dimethyl(oxo)-λ⁶-sulfanylidene]-3,5-difluorobenzamide in 1 mL dichloromethane and 1 mL trifluoracetic acid are stirred overnight at room temperature. The solvents are removed and the residue is purified by preparative HPLC. LC (method 5): $t_R$=0.86 min; Mass spectrum (ESI⁺): m/z=559 [M+H]⁺.

General Procedure 3 (P3) for Examples Shown in Table 3:

0.12 mmol of the corresponding precursor from table 1 in 1 mL dichloromethane and 1 mL trifluoroacetic acid are stirred over night at room temperature. The reaction mixture is purified by preparative HPLC. The product containing fractions are combined and evaporated to dryness.

The following examples in table 3 (example number given in column #) are prepared according to P3.

TABLE 3

| # | structure | name | ESI-MS m/z [M + H⁺] | HPLC $R_t$ [min], [Method] |
|---|---|---|---|---|
| 8 | 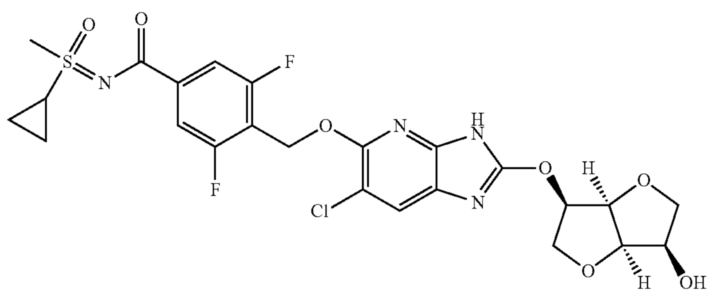 [SMILES: CS(=O)(=NC(=O)c1cc(F)c(COc2nc3[nH]c(O[C@@H]4CO[C@H]5[C@@H]4OC[C@H]5O)nc3cc2Cl)c(F)c1)C1CC1] | 4-{[(2-{[(3R,3aR,6R,6aR)-6-hydroxy-hexahydrofuro[3,2-b]furan-3-yl]oxy}-6-chloro-3H-imidazo[4,5-b]pyridin-5-yl)oxy]-methyl}-N-[cyclopropyl-(methyl)oxo-λ⁶-sulfanylidene]-3,5-difluorobenzamide | 585 | 0.90, [5] |
| 9 | 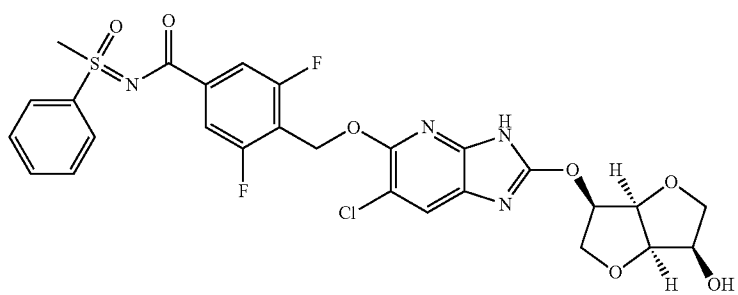 [SMILES: CS(=O)(=NC(=O)c1cc(F)c(COc2nc3[nH]c(O[C@@H]4CO[C@H]5[C@@H]4OC[C@H]5O)nc3cc2Cl)c(F)c1)c1ccccc1] | 4-{[(2-{[(3R,3aR,6R,6aR)-6-hydroxy-hexahydrofuro[3,2-b]furan-3-yl]oxy}-6-chloro-3H-imidazo[4,5-b]pyridin-5-yl)oxy]-methyl}-3,5-difluoro-N-[methyl-(oxo)phenyl-λ⁶-sulfanylidene]-benzamide | 621 | 0.96, [5] |
| 10 | 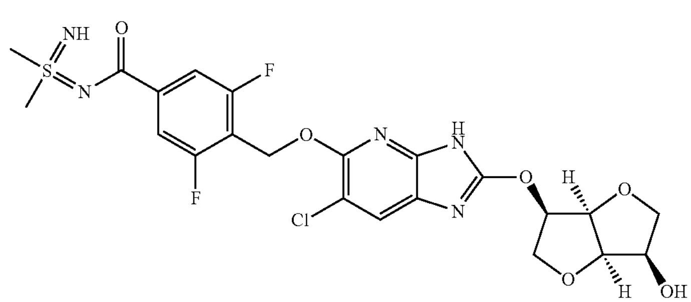 [SMILES: CS(C)(=N)=NC(=O)c1cc(F)c(COc2nc3[nH]c(O[C@@H]4CO[C@H]5[C@@H]4OC[C@H]5O)nc3cc2Cl)c(F)c1] | 4-{[(2-{[(3R,3aR,6R,6aR)-6-hydroxy-hexahydrofuro[3,2-b]furan-3-yl]oxy}-6-chloro-3H-imidazo[4,5-b]pyridin-5-yl)oxy]-methyl}-3,5-difluoro-N-(iminodimethyl-λ⁶-sulfanylidene)-benzamide | 558 | 0.80, [5] |

General Procedure 4 (P4) for Examples Shown in Table 4:

16.9 mg (0.035 mmol) 4-{[(2-{[(3R,3aR,6R,6aR)-6-hydroxy-hexahydrofuro[3,2-b]-furan-3-yl]oxy}-6-chloro-1H-imidazo[4,5-b]pyridin-5-yl)oxy]methyl}-3,5-difluoro-benzoic acid, 0.035 mmol of the corresponding sulfoximine, 15.0 mg (0.039 mmol) HATU and 50.0 µL (0.291 mmol) DIPEA in 1 mL DMF are stirred at room temperature for 1 h. The reaction mixture is purified by preparative HPLC. The product containing fractions are combined and evaporated to dryness.

The following examples in table 4 (example number given in column #) are prepared according to P4.

TABLE 4

| # | structure | name | ESI-MS m/z [M + H]+ | HPLC R$_t$ [min], [Method] |
|---|---|---|---|---|
| 11 | 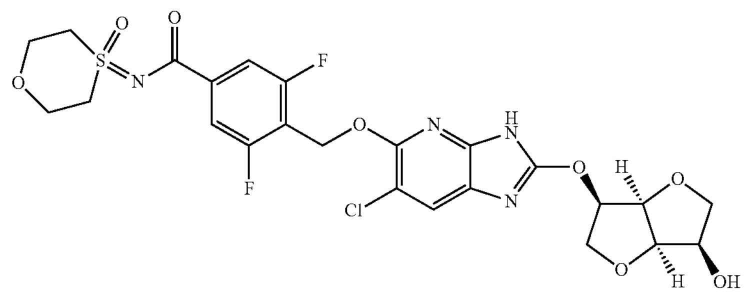 [SMILES: O=C(N=S1(=O)CCOCC1)c1cc(F)c(COc2nc3[nH]c(O[C@@H]4CO[C@H]5[C@@H]4OC[C@H]5O)nc3cc2Cl)c(F)c1] | 4-{[(2-{[(3R,3aR,6R,6aR)-6-hydroxy-hexahydro-furo[3,2-b]furan-3-yl]oxy}-6-chloro-3H-imidazo-[4,6-b]pyridin-5-yl)oxy]methyl}-3,5-difluoro-N-(4-oxo-1,4λ$^6$-oxa-thian-4-ylidene)-benzamide | 601 | 0.65, [1] |
| 12 | 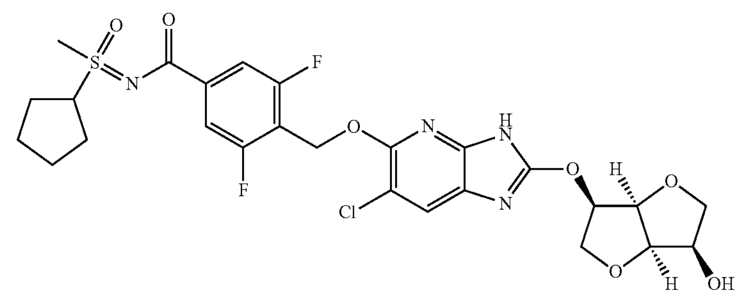 [SMILES: CS(=O)(=NC(=O)c1cc(F)c(COc2nc3[nH]c(O[C@@H]4CO[C@H]5[C@@H]4OC[C@H]5O)nc3cc2Cl)c(F)c1)C1CCCC1] | 4-{[(2-{[(3R,3aR,6R,6aR)-6-hydroxy-hexahydro-furo[3,2-b]furan-3-yl]oxy}-6-chloro-3H-imidazo-[4,5-b]pyridin-5-yl)oxy]methyl}-N-[cyclopentyl-(methyl)oxo-λ$^6$-sulfanylidene]-3,5-difluorobenzamide | 613 | 0.75, [1] |
| 13 | 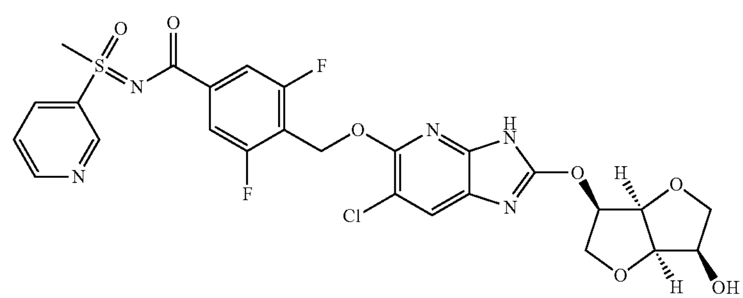 [SMILES: CS(=O)(=NC(=O)c1cc(F)c(COc2nc3[nH]c(O[C@@H]4CO[C@H]5[C@@H]4OC[C@H]5O)nc3cc2Cl)c(F)c1)c1cccnc1] | 4-{[(2-{[(3R,3aR,6R,6aR)-6-hydroxy-hexahydro-furo[3,2-b]furan-3-yl]oxy}-6-chloro-3H-imidazo-[4,5-b]pyridin-5-yl)oxy]-methyl}-3,5-difluoro-N-[methyl-(oxo)-pyridin-3-yl-λ$^6$-sulfanylidene]-benzamide | 622 | 0.46, [2] |
| 14 | 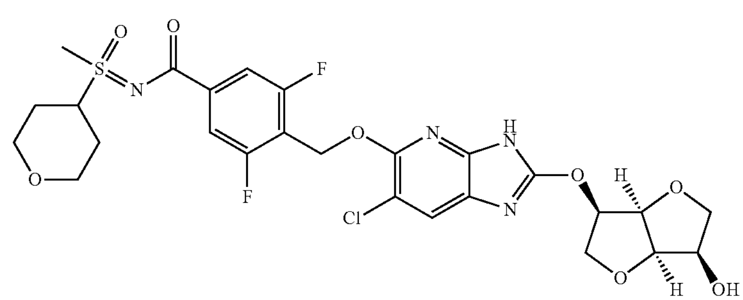 [SMILES: CS(=O)(=NC(=O)c1cc(F)c(COc2nc3[nH]c(O[C@@H]4CO[C@H]5[C@@H]4OC[C@H]5O)nc3cc2Cl)c(F)c1)C1CCOCC1] | 4-{[(2-{[(3R,3aR,6R,6aR)-6-hydroxy-hexahydro-furo[3,2-b]furan-3-yl]oxy}-6-chloro-3H-imidazo[4,5-b]pyridin-5-yl)oxy]-methyl}-3,5-difluoro-N-[methyl-(oxan-4-yl)oxo-λ$^6$-sulfanylidene]-benzamide | 629 | 0.46, [2] |

TABLE 4-continued

| # | structure | name | ESI-MS m/z [M + H+] | HPLC $R_t$ [min], [Method] |
|---|---|---|---|---|
| 15 | 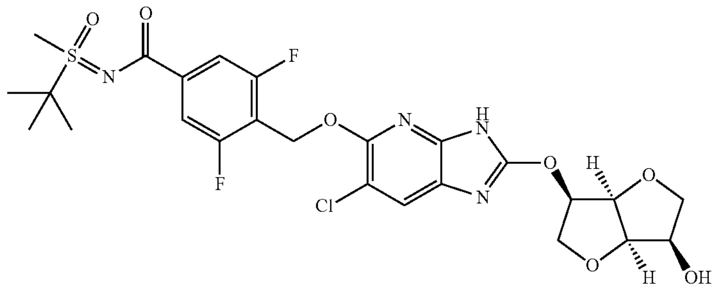 [SMILES: CC(C)(C)S(C)(=O)=NC(=O)c1cc(F)c(COc2nc3[nH]c(O[C@@H]4CO[C@H]5[C@@H]4OC[C@H]5O)nc3cc2Cl)c(F)c1] | 4-{[(2-{[(3R,3aR, 6R,6aR)-6-hydroxy-hexahydrofuran [3,2-b]furan-3-yl]oxy}-6-chloro-3H-imidazo-[4,5-b] pyridin-5-yl)oxy]-methyl}-N-[tert-butyl (methyl)-oxo-λ⁶-sulfanylidene]-3,5-difluorobenzamide | 601 | 0.51, [2] |

Example 16

3-(4-{[(2-{[(3R,3aR,6R,6aR)-6-hydroxy-hexahydro-furo[3,2-b]furan-3-yl]oxy}-6-chloro-3H-imidazo[4,5-b]pyridin-5-yl)oxy]methyl}-3,5-difluorophenyl)-N-[dimethyl(oxo)-λ⁶-sulfanylidene]propanamide

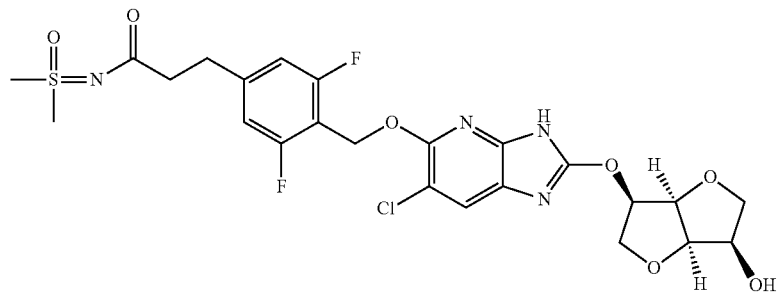 [SMILES: CS(C)(=O)=NC(=O)CCc1cc(F)c(COc2nc3[nH]c(O[C@@H]4CO[C@H]5[C@@H]4OC[C@H]5O)nc3cc2Cl)c(F)c1]

35 mg (0.049 mmol) 3-(4-{[(2-{[(3R,3aR,6R,6aR)-6-hydroxy-hexahydrofuro[3,2-b]furan-3-yl]oxy}-6-chloro-3-{[2-(trimethylsilyl)ethoxy]methyl}-3H-imidazo[4,5-b]-pyridin-5-yl)oxy]methyl}-3,5-difluorophenyl)-N-[di methyl (oxo)-λ⁶-sulfanylidene]-propanamide in 0.8 mL dichloromethane and 0.8 mL trifluoroacetic acid are stirred at 35° C. for 2 h. The solvent is removed with a nitrogen flow and 2 mL acetonitrile is added. After addition of 0.5 mL aqueous ammoniumhydroxide solution the purification is done by preparative HPLC. LC (method 3): $t_R$=0.49 min; Mass spectrum (ESI⁺): m/z=587 [M+H]⁺.

Example 17

(2E)-3-(4-{[(2-{[(3R,3aR,6R,6aR)-6-hydroxy-hexahydrofuro[3,2-b]furan-3-yl]oxy}-6-chloro-3H-imidazo[4,5-b]pyridin-5-yl)oxy]methyl}-3,5-difluorophenyl)-N-dimethyl(oxo)-λ⁶-sulfanylidene]prop-2-enamide

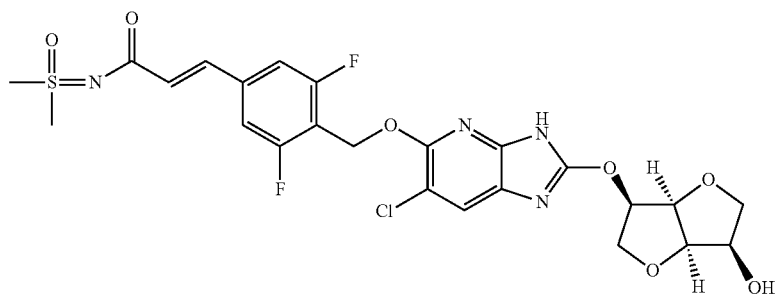 [SMILES: CS(C)(=O)=NC(=O)/C=C/c1cc(F)c(COc2nc3[nH]c(O[C@@H]4CO[C@H]5[C@@H]4OC[C@H]5O)nc3cc2Cl)c(F)c1]

20 mg (0.028 mmol) (2E)-3-(4-{[(2-{[(3R,3aR,6R,6aR)-6-hydroxy-hexahydrofuro[3,2-b]furan-3-yl]oxy}-6-chloro-3-{[2-(trimethylsilyl)ethoxy]methyl}-3H-imidazo[4,5-b]-pyridin-5-yl)oxy]methyl}-3,5-difluorophenyl)-N-[di methyl (oxo)-λ⁶-sulfanylidene]-prop-2-enamide in 3 mL dichloromethane and 400 μL trifluoroacetic acid are stirred at 50° C. for 2.5 h. The reaction mixture is diluted with DMF/acetonitrile and purified by preparative HPLC. LC (method 3): $t_R$=0.52 min; Mass spectrum (ESI⁺): m/z=585 [M+H]⁺.

Example 18

{[3-(4-{[(2-{[(3R,3aR,6R,6aR)-6-hydroxy-hexahydrofuro[3,2-b]furan-3-yl]oxy}-6-chloro-3H-imidazo[4,5-b]pyridin-5-yl)oxy]methyl}-3,5-difluorophenyl)-propyl]imino}-dimethyl-λ⁶-sulfanone

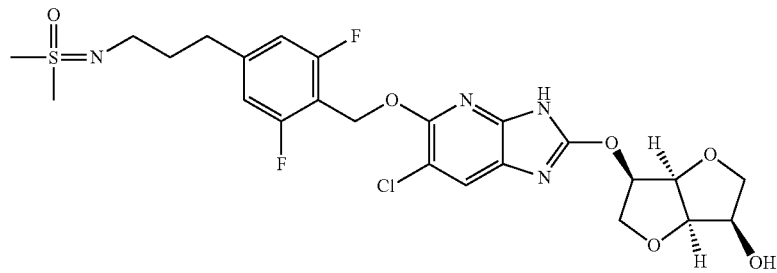 [SMILES: CS(C)(=O)=NCCCc1cc(F)c(COc2nc3[nH]c(O[C@@H]4CO[C@H]5[C@@H]4OC[C@H]5O)nc3cc2Cl)c(F)c1]

0.8 mL trifluoracetic acid is added to 35 mg (0.05 mmol) {[3-(4-{[(2-{[(3R,3aR,6R,6aR)-6-hydroxy-hexahydrofuro[3,2-b]furan-3-yl]oxy}-6-chloro-3-{[2-(tri-methylsilyl)ethoxy]methyl}-3H-imidazo[4,5-b]pyridin-5-yl)oxy]methyl}-3,5-difluorophenyl)propyl]imino}dimethyl-λ⁶-sulfanone in 0.8 mL dichloromethane and stirred at room temperature for 2 h. The solvent is removed and 2 mL acetonitrile and 0.2 mL aqueous NH₄OH are added to the residue. The compound is purified by preparative HPLC. LC (method 3): $t_R$=0.44 min; Mass spectrum (ESI⁺): m/z=573 [M+H]⁺.

General Procedure 5 (P5) for Examples Shown in Table 5:

60.0 mg (0.12 mmol) 4-{[(2-{[(3R,3aR,6R,6aR)-6-hydroxy-hexahydrofuro[3,2-b]-furan-3-yl]oxy}-6-chloro-1H-imidazo[4,5-b]pyridin-5-yl)oxy]methyl}-3,5-difluoro-benzoic acid, 0.12 mmol of the corresponding sulfoximine, 52.0 mg (0.14 mmol) HATU and 86.0 μL (0.50 mmol) DIPEA in 2 mL DMF are stirred at room temperature for 2 h. Water is added to the reaction mixture and extracted with dichloromethane. The combined organic layers are dried and evaporated to dryness. If required the residue is purified by preparative HPLC. The product containing fractions are combined and evaporated to dryness.

The following examples in table 5 (example number given in column #) are prepared according to P5.

TABLE 5

| # | structure | name | ESI-MS m/z [M + H⁺] | HPLC $R_t$ [min], [Method] |
|---|---|---|---|---|
| 19 | 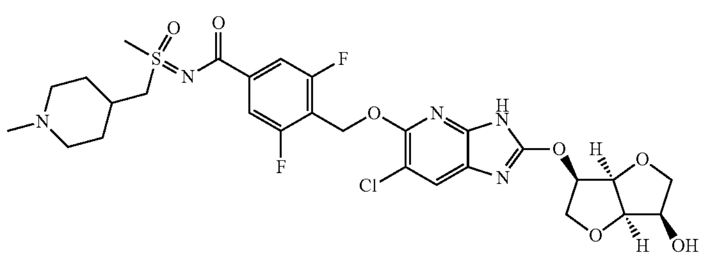 [SMILES: CN1CCC(CS(C)(=O)=NC(=O)c2cc(F)c(COc3nc4[nH]c(O[C@@H]5CO[C@H]6[C@@H]5OC[C@H]6O)nc4cc3Cl)c(F)c2)CC1] | 4-{[(2-{[(3R,3aR,6R,6aR)-6-hydroxy-hexahydro-furo[3,2-b]furan-3-yl]oxy}-6-chloro-3H-imidazo[4,5-b]pyridin-5-yl)oxy]-methyl}-3,5-difluoro-N-{methyl[(1-methyl-piperidin-4-yl)methyl]oxo-λ⁶-sulfanylidene}benzamide | 657 | 0.8, [5] |
| 20 | 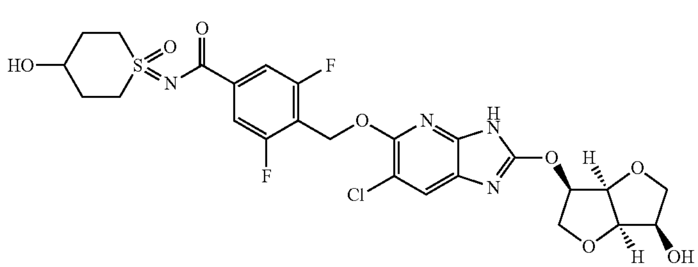 [SMILES: O=C(N=S1(=O)CCC(O)CC1)c1cc(F)c(COc2nc3[nH]c(O[C@@H]4CO[C@H]5[C@@H]4OC[C@H]5O)nc3cc2Cl)c(F)c1] | 4-{[(2-{[(3R,3aR,6R,6aR)-6-hydroxy-hexahydro-furo[3,2-b]furan-3-yl]oxy}-6-chloro-3H-imidazo[4,5-b]pyridin-5-yl)oxy]-methyl}-3,5-difluoro-N-(4-hydroxy-1-oxo-1-λ⁶-thian-1-ylidene)benzamide | 616 | 0.85, [5] |

Example 22

{[(4-{[(2-{[(3R,3aR,6R,6aR)-6-hydroxy-hexahydro-furo[3,2-b]furan-3-yl]oxy}-6-chloro-3H-imidazo[4,5-b]pyridin-5-yl)oxy]methyl}-3,5-difluorophenyl)methyl]imino}dimethyl-λ⁶-sulfanone

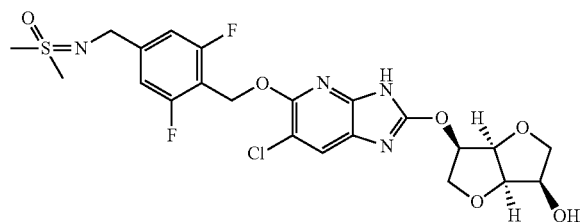 [SMILES: CS(C)(=O)=NCc1cc(F)c(COc2nc3[nH]c(O[C@@H]4CO[C@H]5[C@@H]4OC[C@H]5O)nc3cc2Cl)c(F)c1]

1.0 mL trifluoroacetic acid is added to 40 mg (0.051 mmol) {[(4-{[(2-{[(3R,3aR,6R,6aS)-6-[(tert-butyldimethyl-silyl)oxy]-hexahydrofuro[3,2-b]furan-3-yl]-oxy}-6-chloro-1-{[2-(trimethylsilyl)ethoxy]methyl}-1H-imidazo[4,5-b]pyridin-5-yl)oxy]-methyl}-3,5-difluoro-phenyl)-methyl]imino}dimethyl-λ⁶-sulfanone in 1.0 mL dichloromethane and stirred at room temperature for 3 h. The reactions mixture is concentrated under reduced pressure and the residue is purified by silica chromatography. LC (method 1): $t_R$=0.51 min; Mass spectrum (ESI⁺): m/z=545 [M+H]⁺.

Example 23

(3R,3aR,6R,6aR)-6-({6-chloro-5-[(2,6-difluoro-4-{[methyl(oxan-4-yl)oxo-λ⁶-sulfanylidene]amino}phenyl)methoxy]-3H-imidazo[4,5-b]pyridin-2-yl}oxy)-hexahydrofuro[3,2-b]furan-3-ol

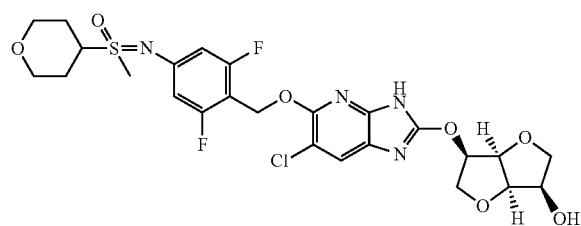 [SMILES: CS(=O)(=Nc1cc(F)c(COc2nc3[nH]c(O[C@@H]4CO[C@H]5[C@@H]4OC[C@H]5O)nc3cc2Cl)c(F)c1)C1CCOCC1]

Under an argon atmosphere 8.1 mg (0.01 mmol) tris(dibenzylidene-acetone)-dipalladium (0) catalyst is added to degassed 60.0 mg (0.12 mmol) (3R,3aR,6R,6aR)-6-({5-[(4-bromo-2,6-difluorophenyl)methoxy]-6-chloro-3H-imidazo[4,5-b]pyridin-2-yl}-oxy)-hexahydrofuro[3,2-b]furan-3-ol, 28.3 mg (0.17 mmol) imino(methyl)oxan-4-yl-λ⁶-sulfanone, 6.9 (0.02 mmol) 2-(di-tert-butylphosphino)-biphenyl, 27.8 mg (0.29 mmol) sodium tert.-butoxide in 2 mL dioxane. The reaction mixture is stirred 3 h at 80° C. The precipitate is collected, dissolved in DMF and purified by preparative HPLC. The product containing fractions are combined and evaporated to dryness. LC (method 5): $t_R$=0.89 min; Mass spectrum (ESI⁺): m/z=601 [M+H]⁺.

Example 24

[(4-{[(2-{[(3R,3aR,6R,6aR)-6-hydroxy-hexahydro-furo[3,2-b]furan-3-yl]oxy}-6-chloro-3H-imidazo[4,5-b]pyridin-5-yl)oxy]methyl}-3,5-difluorophenyl)imino](methyl)[(1-methylpiperidin-4-yl)methyl]-λ⁶-sulfanone

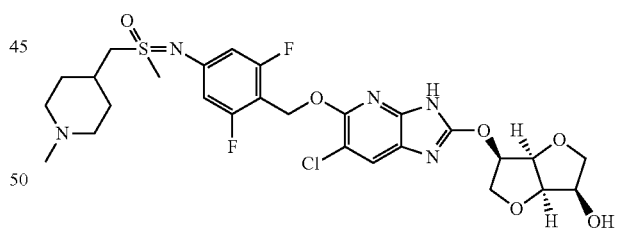

Under an argon atmosphere 8.1 mg (0.01 mmol) tris(dibenzylidene-acetone)-dipalladium (0) catalyst is added to degassed 60.0 mg (0.12 mmol) (3R,3aR,6R,6aR)-6-({5-[(4-bromo-2,6-difluorophenyl)methoxy]-6-chloro-3H-imidazo[4,5-b]pyridin-2-yl}-oxy)-hexahydrofuro[3,2-b]furan-3-ol, 33.0 mg (0.17 mmol) imino(methyl)[(1-methyl-piperidin-4-yl)methyl]-λ⁶-sulfanone, 6.9 (0.02 mmol) 2-(di-tert-butyl-phosphino)-biphenyl, 27.8 mg (0.29 mmol) sodium tert.-butoxide in 2 mL dioxane. The reaction mixture is stirred 3 h at 80° C. The precipitate is collected, dissolved in DMF and purified by preparative HPLC. The product containing fractions are combined and evaporated to dryness. LC (method 5): $t_R$=0.79 min; Mass spectrum (ESI⁺): m/z=628 [M+H]⁺.

The invention claimed is:
1. A compound of formula

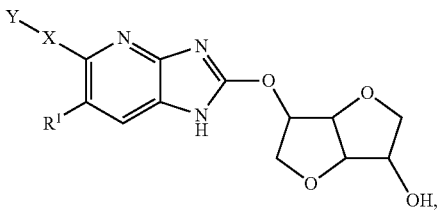

wherein
$R^1$ is selected from the group consisting of F and Cl;
X is selected from the group consisting of a divalent straight-chained or branched —$C_{1-3}$-alkyl-O— linker attached via the O-atom to the imidazopyridine core and
a trivalent linker selected from

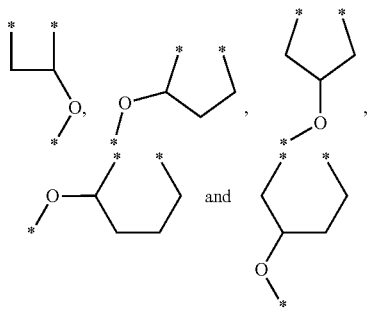

attached via the O-atom to the imidazopyridine core and attached via the remaining two binding positions to vicinal carbon atoms of group Y; and Y is phenyl,
optionally substituted with 1 to 2 groups independently selected from F, Cl, NC—, $H_3C$—, $F_3C$—, and $H_3C$—O—,
but mandatorily substituted with a group selected from $R^S R^{S'}(O=)S=N$—, $R^S R^{S'}(O=)S=N-C_{1-3}$-alkyl-, $R^S R^{S'}(O=)S=N-C(=O)$—, $(R^N)N=S(=O)(R^S)$—, $(R^N)N=S(=O)(R^S)-CH_2$—, $R^S R^{S'}(R^{N'}-N=)S=N-C(=O)$—, $R^S R^{S'}(O=)S=N-C(=O)-C_{1-3}$-alkyl-, $R^S R^{S'}(O=)S=N-C(=O)-C_{2-3}$-alkenyl-, and $R^S R^{S'}(R^{N'}-N=)S=N$—,
wherein $R^N$ is selected from H, NC— and $C_{1-4}$-alkyl, and $R^{N'}$ is selected from H and NC—,
wherein $R^S$ is selected from $H_3C$—, $H_5C_2$— and cyclopropyl, and $R^{S'}$ is independently selected from $C_{1-4}$-alkyl- and $C_{3-6}$-cycloalkyl, from an aryl group selected from phenyl and benzyl, and from the heteroaryl group pyridinyl,
wherein any alkyl and cycloalkyl group mentioned hereinbefore under $R^N$, $R^S$ and $R^{S'}$ is optionally substituted with F, $(C_{1-3}$-alkyl$)_2N$—, $(C_{1-3}$-alkyl)HN—, $H_2N$—, NC—, HO—, $H_3C$—, and $H_3C$—O—,
wherein any aryl and heteroaryl group mentioned hereinbefore under $R^{S'}$ is optionally substituted with 1 to 3 groups independently selected from halogen, NC—, HO—, $C_{1-3}$-alkyl, and $C_{1-3}$-alkyl-O—,
wherein in any definition mentioned hereinbefore and if not specified otherwise, any alkyl group or sub-group may be straight-chained or branched,
or a salt thereof.

2. A pharmaceutically acceptable salt of a compound according to claim 1.

3. A pharmaceutical composition comprising one or more compounds according to claim 1 or one or more pharmaceutically acceptable salts thereof, optionally together with one or more inert carriers and/or diluents.

* * * * *